US006511975B1

(12) United States Patent
Nishi et al.

(10) Patent No.: US 6,511,975 B1
(45) Date of Patent: Jan. 28, 2003

(54) SPIROPIPERIDINE DERIVATIVES

(75) Inventors: Takahide Nishi, Tokyo (JP); Takeshi Yamaguchi, Ushiku (JP); Yukiko Iio, Tokyo (JP); Toshiyasu Takemoto, Tokyo (JP); Katsuyoshi Nakajima, Tokyo (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 09/616,092

(22) Filed: Jul. 13, 2000

Related U.S. Application Data

(63) Continuation-in-part of application No. PCT/JP99/00226, filed on Jan. 22, 1999.

(30) Foreign Application Priority Data

Jan. 23, 1998 (JP) ............................................ 10-11112
May 15, 1998 (JP) .......................................... 10-132959

(51) Int. Cl.$^7$ .................... C07D 413/06; C07D 413/14; C07D 417/06; A61K 31/435; A61P 11/06

(52) U.S. Cl. ............................... 514/232.2; 514/235.5; 544/70

(58) Field of Search ......................... 544/70; 514/235.5, 514/232.2, 235.02

(56) References Cited

U.S. PATENT DOCUMENTS 6,159,967 A 12/2000 Nishi et al.

FOREIGN PATENT DOCUMENTS

| | | |
|---|---|---|
| EP | 776893 | 6/1997 |
| EP | 987269 | 3/2000 |
| JP | 11043435 | 2/1999 |
| WO | WO 94/17045 A1 | 8/1994 |
| WO | WO 98/54191 | 12/1998 |

OTHER PUBLICATIONS

Andersson Ecp. Physiol. 84 (1999) 195–213 (Medline abstract only).*
Barnes Respiration Physiology 123 (2001) 145–154.*
Evangelista Curr. Pharm. Des. 7 (2001) 19–30 (Medline abstract only).*
Holzer Digestion 59 (1998) 269–282 (Medline abstract only).*
Joos et al Allergy 55 (2000) 321–327 (Medline abstract only).*
Lecci et al Neuropeptides 34 (2000) 303–313 (Medline abstract only).*
U.S. patent application Ser. No. 09/533,061, Nishi et al.
U.S. patent application Ser. No. 09/586,728, Nishi et al.

* cited by examiner

*Primary Examiner*—Mukund J. Shah
*Assistant Examiner*—Thomas C. McKenzie
(74) *Attorney, Agent, or Firm*—Frishauf, Holtz, Goodman & Chick, P.C.

(57) ABSTRACT

A compound of the formula (I)

(I)

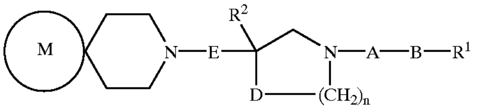

or

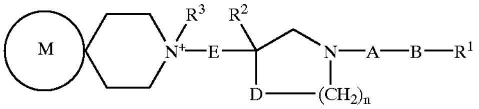

wherein $R^1$ and $R^2$ is a substituted or unsubstituted aryl group, or a substituted or unsubstituted heteroaryl group. A is $CH_2$, CO or $SO_2$. B is a single bond, alkylene or alkenylene. D is O or S. E is alkylene or alkenylene.

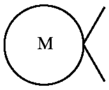

represents

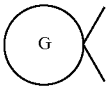

or

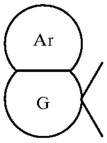

wherein G is a substituted or unsubstituted cycloalkene ring, or a substituted cycloalkane ring. Ar is a substituted or unsubstituted aryl ring, or a substituted or unsubstituted heteroaryl ring. $R^3$ is alkyl. n is 1–3. The invention includes a pharmacologically acceptable salt, ester or other derivative of a compound of the formula (I). The invention also provides pharmaceutical compositions and methods of treating specified diseases utilizing a compound of formula (I).

33 Claims, No Drawings

SPIROPIPERIDINE DERIVATIVES

This application is a continuation-in-part of International Application PCT/JP99/00226 filed Jan. 22, 1999.

FIELD OF THE INVENTION

The present invention relates to novel spiropiperidine derivatives which exhibit antagonistic action against tachykinin receptors ($NK_1$, $NK_2$ and $NK_3$).

BACKGROUND OF THE INVENTION

It is already known that $NK_1$ receptors, $NK_2$ receptors and $NK_3$ receptors act as tachykinin receptors. A number of compounds are known to exhibit antagonistic action against one of these receptors. Recently, compounds which block as many subtypes as possible among these three subtypes have attracted a great deal of attention for use in methods of preventing or treating diseases induced by tachykinin. Compounds exhibiting antagonistic action against both $NK_1$ and $NK_2$ receptors are under investigation.

As a compound having antagonistic activities against both $NK_1$ and $NK_2$ receptors, for example, Compound A shown below is disclosed in EP-776893. However, it is not reported that this compound exhibits an antagonistic activity against $NK_3$ receptor.

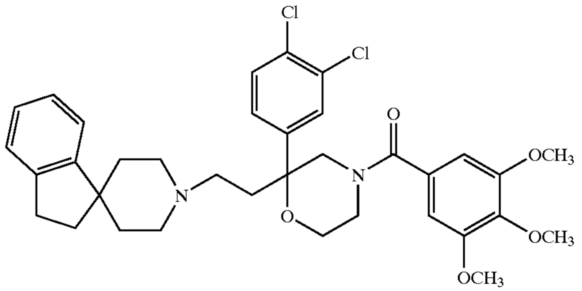

Compound A
(EP-776893
Compound No.2-2012)

DISCLOSURE OF THE INVENTION

The present invention relates to:

(1) a compound represented by the formula (I), or a pharmacologically acceptable salt, ester or other derivative thereof (I)

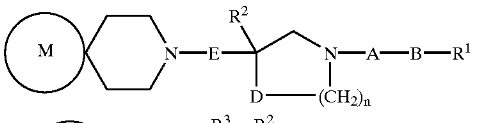

or

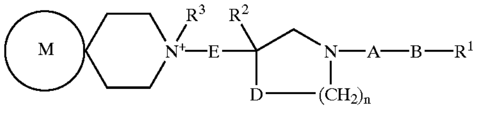

{wherein, $R^1$ and $R^2$ are the same or different and each represents an aryl group, a heteroaryl group, an aryl group substituted with 1 to 3 groups selected from Substituent Group A or a heteroaryl group substituted with 1 to 3 groups selected from Substituent Group A, A represents a methylene group, a carbonyl group or a sulfonyl group, B represents a single bond, a $C_{1-4}$ alkylene group or a $C_{2-4}$ alkenylene group, D represents an oxygen atom or a sulfur atom, E represents a $C_{1-4}$ alkyene or a $C_{2-4}$ alkenylene group,

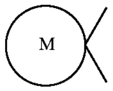

represents

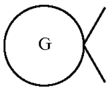

or

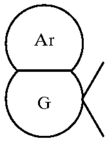

[wherein,

G represents a $C_{5-8}$ cycloalkene ring, a $C_{5-9}$ cycloalkane ring substituted with 1 or 2 groups selected from Substituent Group B or a cycloalkene ring substituted with 1 or 2 groups selected from Substituent Group B, Ar represents an aryl ring, a heteroaryl ring, an aryl ring substituted with 1 to 3 groups selected from Substituent Group A or a heteroaryl ring substituted with 1 to 3 groups selected from Substituent Group A], $R^3$ represents a lower alkyl group, and n represents an integer from 1 to 3;

with the proviso that G does not include a group substituted with only an oxo group or a group substituted with only a lower alkanesulfonyl group},

[Substituent Group A]

halogen atoms, lower alkyl groups, halogeno-lower alkyl groups, lower alkoxy groups, lower alkoxycarbonyl groups, carboxyl groups, hydroxyl groups, lower aliphatic acyl groups, lower aliphatic acylamino groups, amino groups and cyano groups;

[Substituent Group B]

oxo groups, hydroxyl groups, carboxyl groups and thiol groups.

Among these, preferred compounds are:

(2) compounds wherein $R^1$ represents an aryl group, a heteroaryl group or an aryl group substituted with 1 to 3 groups selected from Substituent Group A, (3) compounds wherein $R^1$ represents an aryl group or an aryl group substituted with 1 to 3 groups selected from Substituent Group $A^1$ defined below, (4) compounds wherein $R^2$ represents an aryl group or an aryl group substituted with 1 to 3 groups selected from Substituent Group A, (5) compounds wherein $R^2$ represents an aryl group substituted with at least one group selected from Substituent Group A, (6) compounds wherein A represents a carbonyl group, (7) compounds wherein B represents a single bond, (8) compounds wherein D represents an oxygen atom, (9) compounds wherein E represents a $C_{1-4}$ alkylene group,

(10) compounds wherein E represents a $C_{2-3}$ alkylene group,

(11) compounds wherein

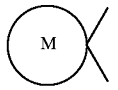

represents

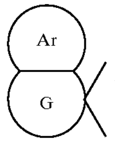

,

(12) compounds wherein G represents a cyclopentane or cyclopentene ring which is substituted with one or two groups selected from Substituent Group B,

(13) compounds wherein G represents a cyclopentane or cyclopentene ring which is substituted with a hydroxy group,

(14) compounds wherein n represents 1 or 2, and

(15) compounds wherein n represents 2;

and pharmacologically acceptable salts, esters or other derivatives thereof.

[Substituent Group $A^1$]

lower alkyl groups, halogeno-lower alkyl groups and lower alkoxy groups.

Of the above-described compounds, compounds which comprise a combination of factors selected from eight groups consisting of (2) and (3); (4) and (5); (6); (7); (8); (9) and (10); (11) to (13); and (14) and (15) are also preferred.

(16) The more preferred compounds are:

1-{2-[(2R)-(3,4-dichlorophenyl)-4-(3,4,5-trimethoxybenzoyl)morpholin-2-yl]ethyl}spiro[(2-hydroxy)indane-1,4'-piperidine], 1-{2-[(2R)-(3,4-dichlorophenyl)-4-(3,4,5-trimethoxybenzoyl)morpholin-2-yl]ethyl}spiro[(3-hydroxy)indane-1,4'-piperidine], 1-{2-[(2R)-(3,4-dichlorophenyl)-4-(3,4,5-trimethoxybenzoyl)morpholin-2-yl]ethyl}spiro[1H-indene-1,4'-piperidine], 1-{2-[(2R)-(3,4-dichlorophenyl)-4-(3,5-dimethoxybenzoyl)morpholin-2-yl]ethyl}spiro[(2-hydroxy)indane-1,4'-piperidine], 1-{2-[(2R)-(3,4-dichlorophenyl)-4-(3,5-dimethoxybenzoyl)morpholin-2-yl]ethyl}spiro[(3-hydroxy)indane-1,4'-piperidine], and 1-{2-[(2R)-(3,4-dichlorophenyl)-4-(3,5-dimethoxybenzoyl)morpholin-2-yl]ethyl}spiro[(1H-indene-1,4'-piperidine], and pharmacologically acceptable salts, esters and other derivatives thereof.

(17) The most preferred compounds are:

1-{2-[(2R)-(3,4-dichlorophenyl)-4-(3,4,5-trimethoxybenzoyl)morpholin-2-yl]ethyl}spiro[(2-hydroxy)indane-1,4'-piperidine] and 1-{2-[(2R)-(3,4-dichlorophenyl)-4-(3,4,5-trimethoxybenzoyl)morpholin-2-yl]ethyl}spiro[(3-hydroxy)indane-1,4'-piperidine], and pharmacologically acceptable salts, esters and other derivatives thereof.

A novel medicine of the present invention comprises as an effective ingredient a compound selected from any one of the compounds described above in (1) to (17), or a pharmacologically acceptable salt, ester or other derivative thereof, and it can be used particularly as a preventive agent or remedy for asthma and/or bronchitis, rhinitis, allergy and urinary incontinence.

In the formula (I), examples of the "aryl group" in the definitions of $R^1$ and $R^2$, the "aryl group" of the "aryl group substituted with 1 to 3 groups selected from Substituent Group A" in the definitions of $R^1$ and $R^2$, and the "aryl group" of the "aryl group which may be substituted with a group selected from Substituent Group A" in the definition of "Substituent Group B", include $C_{5-14}$ aromatic hydrocarbon groups such as phenyl, indenyl, naphthyl, phenanthrenyl and anthracenyl groups, of which phenyl groups are preferred.

Incidentally, the above-described "aryl group" may form a fused ring with a $C_{3-10}$ cycloalkyl group and examples of such a group include 5-indanyl groups.

The "heteroaryl group" in the definitions of $R^1$ and $R^2$, and the "heteroaryl group" of the "heteroaryl group substituted with 1 to 3 groups selected from Substituent Group A" in the definitions of $R^1$ and $R^2$, mean a 5- to 7-membered aromatic heterocyclic group containing 1 to 3 sulfur atoms, oxygen atoms and/or nitrogen atoms. Examples include furyl, thienyl, pyrrolyl, pyrazolyl, imidazolyl, oxazolyl, isoxazolyl, thiazolyl, isothiazolyl, 1,2,3-oxadiazolyl, triazolyl, tetrazolyl, thiadiazolyl, pyridyl, pyridazinyl, pyrimidinyl and pyrazinyl groups. Among these, 5- to 7-membered aromatic heterocyclic groups each of which contain at least one nitrogen atom and may further contain an oxygen atom or sulfur atom are preferred. Examples include pyrrolyl, pyrazolyl, imidazolyl, oxazolyl, isoxazolyl, thiazolyl, isothiazolyl, 1,2,3-oxadiazolyl, triazolyl, tetrazolyl, thiadiazolyl, pyridyl, pyridazinyl, pyrimidinyl and pyrazinyl groups, of which pyridyl, imidazolyl, oxazolyl, pyrazinyl and thiazolyl groups are more preferred.

Incidentally, the above-described "heteroaryl group" may form a fused ring with another cyclic group. Examples of such a group include indolyl, benzofuryl, benzothienyl, benzoxazolyl, benzoimidazolyl, isoquinolyl, quinolyl and quinoxalyl groups.

Examples of the "lower alkyl group" in the definition of $R^3$, [Substituent Group A] and [Substituent Group $A^1$] and the "lower alkyl group" of the "lower alkyl group which may be substituted with a group selected from Substituent Group A" in the definition of [Substituent Group B], include $C_{1-6}$ straight or branched chain alkyl groups such as the methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl groups, of which $C_{1-4}$ straight or branched chain alkyl groups are preferred.

Examples of the "$C_{1-4}$ alkylene group" in the definitions of B and E include $C_{1-4}$ straight or branched chain alkylene groups such as methylene, methylmethylene, ethylene, propylene, trimethylene, tetramethylene, 1-methyltrimethylene, 2-methyltrimethylene and 3-methyltrimethylene groups.

With reference to B, $C_{1-3}$ straight or branched chain alkylene groups are preferred.

With reference to E, $C_{1-3}$ straight or branched chain alkylene groups are preferred, of which the ethylene and trimethylene groups are more preferred, and ethylene groups are most preferred.

Examples of the "$C_{2-4}$ alkenylene group" in the definitions of B and E include $C_{2-4}$ straight or branched chain alkenylene groups such as ethenylene, 2-propenylene, 1-methyl-2-propenylene, 2-methyl-2-propenylene, 2-ethyl-2-propenylene and 2-butenylene groups, of which ethenylene, 2-propenylene and 3-butenylene groups are preferred, and ethenylene and 2-propenylene groups are more preferred.

Examples of the "$C_{5-8}$ cycloalkene ring", and the "$C_{5-8}$ cycloalkene ring" of the "$C_{5-8}$ cycloalkene ring substituted with 1 or 2 groups selected from Substituent Group B" in the definition of G, include cyclopentene, cyclohexene, cycloheptene and cyclooctene rings, of which the "$C_{5-6}$ cycloalkene ring" is preferred, and cyclopentene rings are more preferred.

Examples of the "$C_{5-8}$ cycloalkane ring" of the "$C_{5-8}$ cycloalkane ring substituted with 1 or 2 groups selected from Substituent Group B" represented by G include cyclopentane, cyclohexane, cycloheptane and cyclooctane rings, of which the "$C_{5-6}$ cycloalkane ring" is preferred, and cyclopentane rings are more preferred.

Examples of the "aryl ring", and the "aryl ring" of the "aryl ring substituted with 1 to 3 groups selected from Substituent Group A" in the definition of Ar, include $C_{6-14}$ aromatic hydrocarbon rings such as benzene, indene, naphthalene, phenanthrene and anthracenyl rings, of which benzene rings are preferred.

The "heteroaryl ring", and the "heteroaryl ring" of the "heteroaryl ring substituted with 1 to 3 groups selected from Substituent Group A", each in the definition of Ar, means a 5- to 7-memered aromatic heterocyclic ring containing 1 to 3 sulfur atoms, oxygen atoms or/and nitrogen atoms. Examples include such as furan, thiophene, pyrrole, azepine, pyrazole, imidazole, oxazole, isoxazole, thiazole, isothiazole, 1,2,3-oxadiazole, triazole, tetrazole, thiadiazole, pyran, pyridine, pyridazine, pyrimidine and pyrazine rings. Among these, 5- to 7-membered aromatic heterocyclic rings which contains at least one nitrogen atom and which may also contain an oxygen atom or a sulfur atom are preferred and examples include such as pyrrole, azepine, pyrazole, imidazole, oxazole, isoxazole, thiazole, isothiazole, 1,2,3-oxadiazole, triazole, tetrazole, thiadiazole, pyridine, pyridazine, pyrimidine and pyrazine rings, of which pyridine, imidazole, oxazole, pyrazine and thiazole rings are more preferred.

Accordingly, examples of the group represented by the following formula:

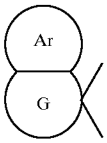

include 2-hydroxyindan-1,1-diyl (particularly, 2S-hydroxyindan-1,1-diyl), 3-hydroxyindan-1,1-diyl, 2,3-dihydroxyindan-1,1-diyl and inden-1,1-diyl.

The "halogen atoms" in the definition of [Substituent Group A] include fluorine, chlorine, bromine and iodine atoms, of which the fluorine and chlorine atoms are preferred.

The "halogeno-lower alkyl groups" in the definition of [Substituent Group A] and [Substituent Group $A^1$] mean the groups wherein a "halogen atom", described above is attached to a "lower alkyl group". Examples include trifluoromethyl, trichloromethyl, difluoromethyl, dichloromethyl, dibromomethyl, fluoromethyl, 2,2,2-trichloroethyl, 2,2,2-trifluoroethyl, 2-bromoethyl, 2-chloroethyl, 2-fluoroethyl and 2,2-dibromoethyl groups, of which trifluoromethyl, 2-bromoethyl, 2-chloroethyl and 2-fluoroethyl groups are preferred.

The "lower alkoxy groups" in the definitions of [Substituent Group A] and [Substituent Group $A^1$], and the "lower alkoxy groups" of the "lower alkoxycarbonyl group" in the definition of [Substituent Group A] mean the group wherein a "lower alkyl group", described above, is attached to an oxygen atom. Examples include $C_{1-6}$ straight or branched chain alkoxy groups such as methoxy, ethoxy, n-propoxy, isopropoxy, n-butoxy, isobutoxy, s-butoxy, tert-butoxy, n-pentoxy, isopentoxy, 2-methylbutoxy, neopentoxy, n-hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy and 2,3-dimethylbutoxy groups, of which $C_{1-4}$ straight or branched chain alkoxy groups are preferred.

The "lower aliphatic acyl groups" and the "lower aliphatic acyl groups" of the "lower aliphatic acylamino groups" in the definition of [Substituent Group A] means $C_{2-7}$ aliphatic acyl groups. Examples include formyl, acetyl, propionyl, butyryl, isobutyryl, pentanoyl, pivaloyl, valeryl and isovaleryl groups, of which acetyl and propionyl groups are preferred.

$R^1$ is, preferably, an aryl group, a heteroaryl group or an aryl group substituted with 1 to 3 groups selected from Substituent Group A; more preferably, is an aryl group or an aryl group substituted with 1 to 3 groups selected from Substituent Group $A^1$; still more preferably, is an aryl group substituted with 1 to 3 groups selected from Substituent Group $A^1$; and, most preferably, is an aryl group substituted with 1 to 3 lower alkoxy groups.

$R^2$ is, preferably, an aryl group substituted with 1 to 3 groups selected from Substituent Group A; more preferably, is an aryl group substituted with 1 to 3 groups selected from Substituent Group A; still more preferably, is an aryl group substituted with 1 to 3 halogen atoms; and, most preferably, is a phenyl group substituted with 1 to 3 halogen atoms.

The following formula preferably represents a group wherein the carbon atom next to the carbon atom which constitutes the spiro bond between the group G and the piperidine ring, and the carbon atom next to the former carbon atom constitute a part of the cyclic group Ar and also a part of the cyclic group G.

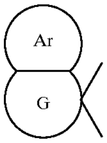

The compounds (I) of the present invention can form and can be used in the form of a "pharmacologically acceptable salt" (referred to herein as "salt").

Preferred examples of the salt comprising the compounds (I) of the invention and an acid include inorganic acid salts such as hydrohalic acid salts (e.g. hydrofluoride, hydrochloride, hydrobromide, hydroiodide, etc.), nitrate, perchlorate, sulfate, phosphate and the like; organic acid salts such as lower alkanesulfonate (e.g. methanesulfonate, trifluoromethanesulfonate, ethanesulfonate, etc.), arylsulfonate (e.g. benzenesulfonate, p-toluenesulfonate, etc.), acetic acid, malic acid, fumarate, succinate, citrate, tartrate, oxalate, maleate and the like; and amino acid salts such as glycine salts, lysine salts, arginine salts, ornithine salts, glutamate, asparate and the like; of which the hydrohalic acid salts and organic acid salts are more preferred, the hydrohalic acid salts are still more preferred and the hydrochloride is most preferred.

Preferred examples of the salt composed of the invention compound (I) and a base, on the other hand, include metal salts, for example, salts of an alkali metal such as sodium salts, potassium salts and lithium salts, salts of an alkaline earth metal such as calcium salts and magnesium salts, aluminum salts and iron salts; amine salts, for example, inorganic salts such as ammonium salts and organic salts such as t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzylphenethylamine salts, piperazine salts, tetramethylammonium salts and tris(hydroxymethyl)aminomethane salts; aminoacid salts such as glycine salts, lysine salts, arginine salts, omithine salts, glutamic acid salts and aspartic acid salts.

Since the compounds (I) of the invention can be converted into the corresponding quaternary amine by modifying the nitrogen atom of the piperidino group in the molecule with the group $R^3$, salts between such a cation-containing compound and an anion (there is no particular limitation on the anion provided that it serves as an anion, but examples include halogen ions such as a chloride ion and an iodide ion) are also embraced in the present invention.

Additionally, the compounds (I) of the present invention absorb water and have adsorbed water added thereto or become a hydrate, when they are allowed to stand in the air. Such hydrates are also embraced in the present invention.

The "ester or other derivative thereof" means a compound wherein a functional group (e.g. a hydroxy group, carboxy group or amino group) is modified with a protecting group or the like and which can be converted into a compound (I) of the present invention after it has been administer ed to a living body. It can be determined whether a compound is such a derivative by administering it to an experimental animal, such as a rat or mouse, by intravenous injection, examining the body fluid of the animal after administration and detecting the original compound or a pharmaceutically acceptable salt thereof.

Since the compound (I) of the present invention can be converted into the corresponding ester, the "ester" thereof means such a pharmaceutically acceptable ester. Examples of the ester include "esters of a hydroxyl group" and "esters of a carboxy group", an ester whose ester residue is a "conventional protecting group" or a "protecting group which can be cleaved in vivo by a biological method such as hydrolysis".

The "conventional protecting group" means a protecting group which can be cleaved by a chemical method such as hydrogenolysis, hydrolysis, electrolysis or photolysis.

Preferred examples of the "conventional protecting group" for the "ester of a hydroxyl group" include the above-described "lower aliphatic acyl groups"; the above-described "aromatic acyl groups"; "tetrahydropyranyl or tetrahydrothiopyranyl groups" such as tetrahydropyran-2-yl, 3-bromotetrahydropyran-2-yl, 4-methoxytetrahydropyran-4-yl, tetrahydrothiopyran-2-yl and 4-methoxytetrahydrothiopyran-4-yl groups; "tetrahydrofuranyl or tetrahydrothiofuranyl groups" such as tetrahydrofuran-2-yl and tetrahydrothiofuran-2-yl groups; "silyl groups", for example, tri(lower alkyl)silyl groups such as trimethylsilyl, triethylsilyl, isopropyldimethylsilyl, t-butyldimethylsilyl, methyldiisopropylsilyl, methyl-di-t-butylsilyl and triisopropylsilyl groups and tri(lower alkyl) silyl groups substituted with 1 or 2 aryl groups such as diphenylmethylsilyl, diphenylbutylsilyl, diphenylisopropylsilyl and phenyldiisopropylsilyl groups; "alkoxymethyl groups", for example, lower alkoxymethyl groups such as methoxymethyl, 1,1-dimethyl-1-methoxymethyl, ethoxymethyl, propoxymethyl, isopropoxymethyl, butoxymethyl and tert-butoxymethyl groups, lower alkoxymethyl groups substituted with lower alkoxy groups such as 2-methoxyethoxymethyl groups and (halogeno lower alkoxy)methyl groups such as 2,2,2-trichloroethoxymethyl and bis(2-chloroethoxy)methyl groups; "substituted ethyl groups", for example, ethyl groups substituted with a lower alkoxy group such as 1-ethoxyethyl and 1-(isopropoxy)ethyl groups and halogenated ethyl groups such as 2,2,2-trichloroethyl groups; "aralkyl groups", for example, lower alkyl groups substituted with 1 to 3 aryl groups such as benzyl, α-naphthylmethyl, β-naphthylmethyl, diphenylmethyl, triphenylmethyl, α-naphthyldiphenylmethyl and 9-anthrylmethyl groups and lower alkyl groups each substituted with 1 to 3 aryl groups having an aryl substituted with a lower alkyl, halogeno(lower alkyl), lower alkoxy, nitro, halogen or cyano group such as 4-methylbenzyl 2,4,6-trimethylbenzyl, 3,4,5-trimethylbenzyl, 3,5-di(trifluoromethyl)benzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl groups; and the above-described "lower alkoxycarbonyl groups".

Preferred examples of the "conventional protecting group" for the "ester of a carboxyl group" include the above-described "lower alkyl groups"; lower alkenyl groups such as ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl and 5-hexenyl; lower alkynyl groups such as ethynyl, 2-propynyl, 1-methyl-2-propynyl, 2-butynyl, 1-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl and 5-hexynyl groups; the above-described "halogeno-lower alkyl groups"; hydroxy"lower alkyl groups" such as 2-hydroxyethyl, 2,3-dihydroxypropyl, 3-hydroxypropyl, 3,4-dihydroxybutyl and 4-hydroxybutyl groups; "lower aliphatic acyl"-"lower alkyl groups" such as acetylmethyl groups; the above-described "aralkyl groups"; and the above-described "silyl groups".

The "protecting group which can be cleaved in vivo by a biological method such as hydrolysis" means a protecting group which is cleaved in vivo by a biological method such as hydrolysis and forms a free acid or salt thereof. It can be determined whether a compound is such an ester by administering it to an experimental animal, such as a rat or mouse, by intravenous injection, examining the body fluid of the animal after administration and detecting the original compound or a pharmaceutically acceptable salt thereof.

Preferred examples of the "protecting group which can be cleaved in vivo by a biological method such as hydrolysis" for the "ester of a hydroxyl group" include 1-(acyloxy) "lower alkyl groups", for example, 1-("lower aliphatic acyl"oxy)"lower alkyl groups" such as formyloxymethyl, acetoxymethyl, dimethylaminoacetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxvpropyl, 1-acetoxybutyl, 1-propionyloxybutyl, 1-butyryloxybutyl, 1-pivaloyloxvbutyl, 1-acetoxypentyl, 1-propionyloxypentyl, 1-butyryloxypentyl, 1-pivaloyloxypentyl and 1-pivaloyloxyhexyl groups, 1-("cycloalkyl"carbonyloxy)"lower alkyl groups" such as cyclopentylcarbonyloxymethyl, cyclohexylcarbonyloxymethyl, 1-cyclopentylcarbonyloxyethyl, 1-cyclohexylcarbonyloxyethyl, 1-cyclopentylcarbonyloxypropyl, 1-cyclohexylcarbonyloxypropyl, 1-cyclopentylcarbonyloxybutyl and 1-cyclohexyl-carbonyloxybutyl groups, and 1-("aromatic acyl"oxy)"lower alkyl groups" such as benzoyloxymethyl groups; (lower alkoxycarbonyloxy)alkyl groups such as methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, pentyloxycarbonyloxymethyl, hexyloxycarbonyloxymethyl, cyclohexyloxycarbonyloxymethyl, cyclohexyloxycarbonyloxy(cyclohexyl)methyl, 1-(methoxycarbonyloxy)ethyl, 1-(ethoxycarbonyloxy)ethyl, 1-(propoxycarbonyloxy)ethyl, 1-(isopropoxycarbonyloxy)ethyl, 1-(butoxycarbonyloxy)ethyl, 1-(isobutoxycarbonyloxy)ethyl, 1-(tert-butoxycarbonyloxy)ethyl, 1-(pentyloxycarbonyloxy)ethyl, 1-(hexyloxycarbonyloxy)ethyl, 1-(cyclopentyloxycarbonyloxy)ethyl, 1-(cyclopentyloxycarbonyloxy)propyl, 1-(cyclohexyloxycarbonyloxy)propyl, 1-(cyclopentyloxycarbonyloxy)butyl, 1-(cyclohexyloxycarbonyloxy)butyl, 1-(cyclohexyloxycarbonyloxy)ethyl, 1-(ethoxycarbonyloxy)propyl, 2-(methoxycarbonyloxy)ethyl, 2-(ethoxycarbonyloxy)ethyl, 2-(propoxycarbonyloxy)ethyl, 2-(isopropoxycarbonyloxy)ethyl, 2-(butoxycarbonyloxy)ethyl, 2-(isobutoxycarbonyloxy)ethyl, 2-(pentyloxycarbonyloxy)ethyl, 2-(hexyloxycarbonyloxy)ethyl, 1-methoxycarbonyloxy)propyl, 1-(ethoxycarbonyloxy)propyl, 1-(propoxycarbonyloxy)propyl, 1-(isopropoxycarbonyloxy)propyl, 1-(butoxycarbonyloxy)propyl, 1-(isobutoxycarbonyloxy)propyl, 1-(pentyloxycarbonyloxy)propyl, 1-(hexyloxycarbonyloxy)propyl, 1-(methoxycarbonyloxy)butyl, 1-(ethoxycarbonyloxy)butyl, 1-(propoxycarbonyloxy)butyl, 1-(isopropoxycarbonyloxy)butyl, 1-(butoxycarbonyloxy)butyl, 1-(isobutoxycarbonytoxy)butyl, 1-(methoxycarbonyloxy)pentyl, 1-(ethoxycarbonyloxy)pentyl, 1-(methoxycarbonyloxy)hexyl and 1-(ethoxycarbonyloxy)hexyl groups; and oxodioxolenylmethyl groups such as (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl, [5-(4-chlorophenyl)-2-oxo-1,3-dioxolen-4-yl]methyl, (2-oxo-1,3-dioxolen-4-yl)methyl, (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl and (5-butyl-2-oxo-1,3-dioxolen-4-yl)methyl groups: "phthalidyl groups" such as phthalidyl, dimethylphthalidyl and dimethoxyphthalidyl groups: the above-described "lower aliphatic acyl groups": the above-described "aromatic acyl groups": "half ester salt residue of succinic acid": "phosphate salt residues": "ester forming residues such as with amino acids": carbamoyl groups: carbamoyl groups substituted with 1 or 2 lower alkyl groups: and "1-(acyloxy)alkyloxycarbonyl groups" such as pivaloyloxymethyloxycarbonyl, of which the "carbonyloxyalkyl groups" are preferred.

Preferred examples of the "protecting group which can be cleaved in vivo by a biological method such as hydrolysis" for the "ester of a carboxy group" include "alkoxy lower alkyl groups", for example, (lower alkoxy)(lower alkyl) groups such as methoxyethyl, 1-ethoxyethyl, 1-methyl-1-methoxyethyl, 1-(isopropoxy)ethyl, 2-methoxyethyl, 2-ethoxyethyl, 1,1-dimethyl-1-methoxyethyl, ethoxymethyl, n-propoxymethyl, isopropoxymethyl, n-butoxymethyl and tert-butoxymethyl groups, (lower alkoxy)lower alkyl groups substituted with lower alkoxy such as 2-methoxyethoxymethyl, "aryl"oxy"lower alkyl groups" such as phenoxymethyl groups and (halogenated lower alkoxy)(lower alkyl) groups such as 2,2,2-trichloroethoxymethyl and bis(2-chloroethoxy)methyl groups; " "lower alkoxy"carbonyl"lower alkyl groups"" such as methoxycarbonylmethyl groups; "cyano"lower alkyl groups"" such as cyanomethyl and 2-cyanoethyl groups; ""lower alkyl"thiomethyl groups" such as methylthiomethyl and ethylthiomethyl groups; ""aryl"thiomethyl groups" such as phenylthiomethyl and naphthylthiomethyl groups; "lower alkyl"sulfonyl"lower alkyl groups" which may be substituted with halogen" such as 2-methanesulfonylethyl and 2-trifluoromethanesulfonylethyl groups; ""aryl"sulfonyl-"lower alkyl groups"" such as 2-benzenesulfonylethyl and 2-toluenesulfonylethyl groups; the above-described "1-(acyloxy)"lower alkyl groups""; the above-described "phthalidyl groups"; the above-described "aryl groups"; the above-described "lower alkyl groups"; "carboxyalkyl groups" such as carboxymethyl groups; and "amide forming residues of amino acids" such as phenylalanine groups.

When the compound (I) of the present invention contains an amino and/or carboxyl group, it can be converted into derivatives other than the above-described "pharmacologically acceptable salts" and "esters thereof". "Other derivatives" mean such derivatives. Examples of such derivatives include amide derivatives.

The compound (I) of the present invention contains an asymmetric carbon atom in the molecule thereof and stereoisomers whose asymmetric carbon atom has the R or S configurations are present. The stereoisomers and a mixture thereof at any ratio are also included in the present invention.

MODE FOR CARRYING OUT THE INVENTION

The spiropiperidine derivative of the present invention can be prepared by the below-described method.

[Method A]

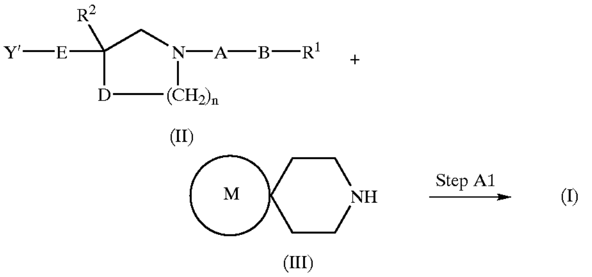

In the above reaction scheme, $R^1$, $R^2$, A, B, D, E, M and n have the same meanings as described above.

Y' may be any group which is capable of being eliminated as a nucleophilic residue and is not specifically limited. Preferred examples of such groups include halogen atoms such as chlorine, bromine and iodine atoms; trihalomethoxy groups such as trichloromethoxy groups; lower alkanesulfonyloxy groups such as methanesulfonyloxy and ethanesulfonyloxy groups; (halogeno lower alkane)sulfonyloxy groups such as trifluoromethanesulfonyloxy and pentafluoroethanesulfonyloxy groups; and arylsulfonyloxy groups such as benzenesulfonyloxy, p-toluenesulfonyloxy and p-nitrobenzenesulfonyloxy groups, of which the halogen atoms and the lower alkanesulfonyloxy groups are still more preferred.

Step A1 is a step of preparing the compound (I) of the present invention by reacting Compound (II) with Compound (III) in a solvent in the presence of a base.

There is no particular limitation on the nature of the solvent to be employed, provided that it has no adverse effects on the reaction and can dissolve the starting materials at least to some extent. Preferred examples include aliphatic hydrocarbons such as hexane, heptane, ligroin and petroleum ether; aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; ketones such as acetone, methyl ethyl ketone, methyl isobutyl ketone, isophorone and cyclohexanone; nitro compounds such as nitroethane and nitrobenzene; nitriles such as acetonitrile and isobutylonitrile; amides such as formamide, N,N-dimethylformamide, N,N-dimethylacetamide, N-methyl-2-pyrrolidone, N-methylpyrrolidinone and hexamethylphosphoric triamide; and sulfoxides such as dimethylsulfoxide and sulfolane, of which the amides, ethers and nitriles are more preferred and the amides are most preferred.

There is no particular limitation on the nature of the base to be employed provided that it is used in ordinary reactions. Preferred examples include combinations of a metal iodide (e.g. potassium iodide) and an inorganic base, such as an alkali metal carbonate (e.g. sodium carbonate, potassium carbonate or lithium carbonate), an alkali metal hydrogencarbonate (e.g. sodium hydrogencarbonate, potassium hydrogencarbonate or lithium hydrogencarbonate), an alkali metal hydride (e.g. lithium hydride, sodium hydride or potassium hydride), an alkali metal hydroxide (e.g. sodium hydroxide, potassium hydroxide, barium hydroxide or lithium hydroxide) or an alkali metal fluoride (e.g. sodium fluoride or potassium fluoride); or an organic base such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU), of which the combination of a metal iodide and an inorganic base is still more preferred and the combination of a metal iodide and an alkali metal hydrogencarbonate is most preferred.

The range of reaction temperature is from 0 to 150° C., from 20 to 120° C.

Although the reaction time depends mainly on the reaction temperature and the nature of the raw materials, reaction reagents and solvent to be employed, the range is usually from 30 minutes to 48 hours, from 1 to 12 hours.

A compound of the formula (I) wherein a carbon atom, which is a ring-atom of group G and which is not adjacent to the piperidine ring, has a hydroxyl group can be prepared by reduction of the corresponding ketone derivative, which is prepared in accordance with the above-described Method A.

There is no particular limitation on the nature of the solvent to be employed provided that it has no adverse effects on the reaction and can dissolve the starting materials at least to some extent. Preferred examples include alcohols such as methanol and ethanol; halogenated hydrocarbons such as methylene chloride, chloroform, carbon tetrachloride, dichloroethane, chlorobenzene and dichlorobenzene; and ethers such as diethyl ether, diisopropyl ether, tetrahydrofuran, dioxane, dimethoxyethane and diethylene glycol dimethyl ether, of which the alcohols are preferred and the ethanol is most preferred.

There is no particular limitation on the reducing agent to be employed provided that it is ordinarily used as a reducing agent. Preferred examples include hydride reagents such as alkali metal borohydrides (e.g. sodium borohydride or lithium borohydride), aluminum hydride compounds (e.g. lithium aluminum hydride or lithium triethoxyaluminum hydride), sodium tellurium hydride, and organic aluminum hydride reducing agents [e.g. diisobutylaluminum hydride or sodium di(methoxyethoxy)aluminum dihydride], of which the alkali metal borohydrides and organic aluminum hydride reducing agents are more preferred and the alkali metal borohydrides are most preferred.

The range of reaction temperature is from −78 to 50° C., −20 to 20° C.

The reaction time depends mainly on the reaction temperature, natures of the raw materials, reaction reagents and solvent to be employed. The range is usually from 5 minutes to 24 hours, 10 minutes to 2 hours.

After the completion of the respective reactions, the compounds produced by the respective reactions may be collected from the reaction mixture by a conventional process.

For example, the reaction mixture is appropriately neutralized and, after insoluble matter, if any, has been removed by filtration, a water immiscible organic solvent (e.g. ethyl acetate) is added. After washing with water and the like, the organic layer containing the desired compound is separated and dried over anhydrous magnesium sulfate and the like. Then, the solvent is distilled off to give the objective compound.

The resultant desired compound can, if desired, be isolated and purified by using conventional procedures such as recrystallization and reprecipitation, or by procedures which are conventionally used for isolation and purification of organic compounds, for example, an adsorption column chromatography process using a carrier such as silica gel, alumina or magnesium-silica gel, Florisil; a process using a synthetic adsorbent, for example, partition column chromatography using Sephadex LH-20 (manufactured by Pharmacia Co.), Amberlite XAD-11 (manufactured by Rohm & Haas Co.), Diaion HP-20 (manufactured by Mitsubishi Kasei Co., Ltd.); a process using ion-exchange chromatography; or a normal/reversed phase liquid chromatography process ( high performance liquid chromatography) using silica gel or alkylated silica gel; or in combination using a suitable eluent.

Incidentally, the raw materials are commercially available or can be prepared easily by a known method. For example, the compound of the formula (II) can be prepared by the method described in EP-776893 and the like, while the compound of the formula (III) can be prepared using methods well known in the art. See for example U.S. Pat. No. 5,578,593 and the like.

The novel spiropiperidine derivatives of the present invention exhibit excellent antagonism against tachykinin, excellent antagonistic activity against $NK_1$, $NK_2$ and $NK_3$ receptors, excellent oral absorption and less toxicity so that they are useful as a medicament. Examples of the diseases for which the medicament is useful as a preventive or remedy include diseases of the central nervous system such as anxiety, depression, psychosis and schizophrenia; sleep apnea syndrome; neurodegenerative diseases such as dementia of AIDS, Alzheimer's senile dementia, Alzheimer's disease, Down's syndrome, demyelinating disease, amyotrophic lateral sclerosis, neuropathy, peripheral neuropathy and neuralgia; respiratory diseases such as chronic obstructive lung diseases, bronchitis, pneumonia, bronchoconstriction, asthma and coughs; inflammatory diseases such as inflammatory bowel diseases (IBD), psoriasis, fibrositis, arthrosteitis, osteoarthritis and rheumatoid arthritis; allergic diseases such as rhinitis and eczema; hypersensitivity diseases such as hypersensitivity to vines; ophthalmological diseases such as conjunctivitis, vernal conjunctivitis, vernal catarrh, destruction of the blood-aqueous humor barrier caused by various inflammatory eye diseases, elevated in intraocular pressure and miosis; skin diseases such as contact dermatitis, atopic dermatitis, urticaria and other eczematoid dermatitis; addiction such as alcohol dependency; somatic diseases caused by stress; sympathetic reflex dystrophy such as hand and shoulder syndrome; dysthymia; undesirable immune reactions including rejection of grafts, disease relating to immunopotentiation including systemic lupus erythematosus or immunosuppression; digestive diseases including diseases caused by abnormalities in nerves regulating the organs, colitis, ulcerative colitis and Crohn's disease; emesis including emesis induced by adverse effects of X-ray irradiation and chemotherapy, poisons, toxins, pregnancy, vestibular disorders, postoperative illness, gastrointestinal occlusion, reduced gastrointestinal movement, visceral pain, migraines, increased intracranial pressure, reduced intracranial pressure or administration of various drugs; urinary bladder functional disease such as cystitis and urinary incontinence; eosinophilia caused by collagen diseases, scieriasis or Fasciola hepatica infection; diseases caused by the abnormal blood flow due to vasodilation or vasoconstriction such as angina pectoris, migraines and Reynauds's disease; and pain of pain nociceptive reception such as migraines, headaches and toothache.

The compound (I) of the present invention can be administered orally, for example, in the form of tablets, capsules granules, powders or syrups; administered parenterally, for example, in the form of injection preparations or suppositories; intravenously; in inhalation sprays; skin patches; etc. These preparations may be produced using pharmaceutically acceptable carriers, such as excipients [e.g. sugar derivatives, such as lactose, sucrose, glucose, mannitol, or sorbitol; starch derivatives, such as corn starch, potato starch, α-starch, dextrin or carboxymethyl starch; cellulose derivatives, such as crystalline cellulose, low-substituted hydroxypropylcellulose, hydroxypropylmethylcellulose, carboxymethyl-cellulose, carboxymethylcellulose calcium or internally cross-linked carboxy-methylcellulose sodium; gum arabic; dextran; organic excipients, such as pullulan; silicate derivatives, such as light anhydrous silicic acid, synthetic aluminum silicate or magnesium aluminate metasilicate; phosphates, such as calcium phosphate; carbonates, such as calcium carbonate; inorganic excipients, such as sulfates (e.g. calcium sulfate)]; lubricants [e.g. metal stearates, such as stearic acid, calcium stearate, and magnesium stearate; talc; colloidal silica; waxes, such as bee gum, and spermaceti; boric acid; adipic acid; sulfates, such as sodium sulfate; glycol; fumaric acid; sodium benzoate; DL leucine; fatty acid sodium salt; laurylsulfates, such as sodium laurylsulfate, and magnesium laurylsulfate; silicic acids, such as anhydrous silicic acid, and silicate hydrate; and the above starch derivatives]; binders [e.g. polyvinyl pyrrolidone, macrogol and the same compounds as those of the above excipients]; disintegrators [e.g. the same compounds as those of the above excipients and chemically modified starchcelluloses, such as croscarmellose sodium, carboxymethylstarch sodium and cross-linked polyvinylpyrrolidone]; stabilizers [e.g. paraoxybenzoates, such as methylparaben, and propylparaben; alcohols, such as chlorobutanol, benzyl alcohol, and phenylethyl alcohol; benzalkonium chloride; phenols, such as phenol, and cresol; thimerosal; dehydroacetic acid; and sorbic acid]; corrigents [e.g. normally used sweetening agents, sour agents, and perfumes]; and diluents according to a per se known process.

The dose varies depending on the severity of the diseases, the age of the patient (human or mammal), the administration route and the like. For example, in the case of oral administration, it is advantageous that the compound of the present invention is administered one to several times per day with a dose of from 0.01 mg/kg body weight (preferably 0.1 mg/kg body weight) lower limit to 100 mg/kg body weight (preferably 50 mg/kg body weight) upper limit according to the severity of the disease. In the case of intravenous administration, it is advantageous that the compound of the present invention is administered one to several times per day with a dose of 0.01 mg/kg body weight (preferably 0.05 mg/kg body weight) lower limit to 100 mg/kg body weight (preferably 50 mg/kg body weight) upper limit according to the severity of the disease.

The present invention provides pharmaceutical compositions comprising (i) an effective amount of the compound (I) and/or a pharmaceutically acceptable salt or ester or other derivative thereof and (ii) a pharmaceutical carrier. The present invention also provides methods to prevent or treat the diseases and conditions identified in this specification by administering an effective amount of the compound (I) or a pharmaceutically acceptable salt or ester or other derivative thereof.

The present invention will hereinafter be described in further detail with reference to examples, formulation examples and test examples. However, these are not intended to limit the scope of the present invention.

EXAMPLES

Example 1

1-{2-[(2R)-(3,4-Dichlorophenyl)-4-(3,4,5-trimethoxybenzoyl)morpholin-2-yl]ethyl}spiro[(2-hydroxy)indane-1,4'-piperidine]

(The below-described Compound No. 138)

In 4 ml of anhydrous dimethylformamide, 200 mg (0.37 mmol) of 2-[(2R)-(3,4-dichlorophenyl)-4-(3,4,5-trimethoxybenzoyl)morpholin-2-yl]ethanol methanesulfonate, 96 mg (0.40 mmol) of spiro[(2-hydroxy)indane-1,4'-piperidine]hydrochloride obtained in Referential Example 3, 92 mg (1.10 mmol) of sodium bicarbonate and 91 mg (0.55 mmol) of potassium iodide were suspended, followed by heating at 80° C. for 8 hours under a nitrogen atmosphere. Water was added to the reaction mixture and the resulting mixture was extracted with ethyl acetate. The organic layer was dried over anhydrous magnesium sulfate. The solvent was then distilled off under reduced pressure. The residue was purified by silica gel thin layer chromatography (developing agent; methylene chloride:methanol=10:1), whereby 175 mg (73%) of the title compound were obtained as white crystals.

$[\alpha]_D^{25}$+11.8° (c=0.56, chloroform)

Nuclear magnetic resonance spectrum (400 MHz, $CDCl_3$) δ ppm: 7.16–7.67 (7H,m), 6.52 (2H,s), 4.40 (1H,s), 3.85 (9H,s), 3.37–4.04 (6H,m), 3.27 (1H,dd,J=16.7,5.3 Hz), 2.82 (1H,d,J=16.7 Hz), 2.62–2.88 (2H,m), 1.49–2.40 (10H,m).

Infrared absorption spectrum $\nu_{max}$ $cm^{-1}$ (KBr): 3432, 2934, 1634, 1584

Mass spectrometric analysis (FAB) m/z: 655 ($(M+H)^+$)

Elemental analysis (% based on $C_{35}H_{40}N_2O_6Cl_2.0.5H_2O$)

Calculated: C; 63.25, H; 6.22, N; 4.21, Cl; 10.67 Found: C; 63.24, H; 6.37, N; 4.14, Cl; 10.41

Example 2

1-{2-[(2R)-(3,4-Dichlorophenyl)-4-(3,4,5-trimethoxybenzoyl)mopholin-2-yl]ethyl}spiro[(3-hydroxy)indane-1,4'-piperidine]

(The below-described Compound No. 106)

Example 2a

1-{2-[(2R)-(3,4-Dichlorophenyl)-4-(3,4,5-trimethoxybenzoyl)morpholin-2-yl]ethyl}spiro[(3-indanone)-1,4'-piperidine]

In 4 ml of anhydrous dimethylformamide, 200 mg (0.37 mmol) of 2-[(2R)-(3,4-dichlorophenyl)-4-(3,4,5-trimethoxybenzoyl)morpholin-2-yl]ethanol methanesulfonate, 95 mg (0.40 mmol) of spiro[(3-indanone)-1,4'-piperidine]hydrochloride obtained in Referential Example 5, 92 mg (1.10 mmol) of sodium bicarbonate and 91 mg (0.55 mmol) of potassium iodide were suspended, followed by heating at 80° C. for 8 hours under a nitrogen atmosphere. Water was added to the reaction mixture and the resulting mixture was extracted with ethyl acetate. The organic layer was dried over anhydrous magnesium sulfate. The solvent was then distilled off under reduced pressure. The residue was purified by silica gel thin layer chromatography (developing agent; methylene chloride:methanol=10:1), whereby 167 mg (70%) of the title compound were obtained as white crystals.

$[\alpha]_D^{25}$+4.3° (c 0.53, chloroform)

Nuclear magnetic resonance spectrum (400 MHz, $CDCl_3$) δ ppm: 7.29–7.78 (7H,m), 6.49 (2H,s), 3.85 (9H,s), 3.30–3.92 (6H,m), 2.74–2.96 (2H,m), 2.52 (2H,s), 1.93–2.30 (8H,m), 1.47–1.50 (2H,m).

Infrared absorption spectrum $\nu_{max}$ $cm^{-1}$ (KBr): 3416, 2933, 1714, 1637, 1603

Mass spectrometric analysis (FAB) m/z: 653 ($(M+H)^+$)

Elemental analysis (% based on $C_{35}H_{38}N_2O_6Cl_2.0.5H_2O$)

Calculated: C; 63.44, H; 5.93, N; 4.22, Cl; 10.70 Found: C; 63.63, H; 6.20, N; 4.11, Cl; 10.26

Example 2b

1-{2-[(2R)-(3,4-Dichlorophenyl)-4-(3,4,5-trimethoxybenzoyl)morpholin-2-yl]ethyl}spiro[(3-hydroxy)indane-1,4'-piperidine]

In 1 ml of ethanol, 24 mg (0.62 mmol) of sodium borohydride were dissolved. To the resulting solution, an ethanol (1ml) solution of 1-{2-[(2R)-(3,4-dichlorophenyl)-4-(3,4,5-trimethoxybenzoyl)morpholin-2-yl]ethyl}spiro[(3-indanone)-1,4'-piperidine] (100 mg (0.16 mmol)), which had been prepared in Example 2a, was added under ice cooling, followed by stirring for 2 hours under a nitrogen atmosphere. Water was added to the reaction mixture and the resulting mixture was extracted with ethyl acetate. The organic layer was dried over anhydrous magnesium sulfate. The solvent was then distilled off under reduced pressure. The residue was purified by silica gel thin layer chromatography (developing agent; methylene chloride:methanol=10:1), whereby 80 mg (78%) of the title compound were obtained as white crystals.

$[\alpha]_D^{25}$+8.3° (c 0.52, chloroform)

Nuclear magnetic resonance spectrum (400 MHz, $CDCl_3$) δ ppm: 7.19–7.69 (7H,m), 6.50 (2H,s), 5.23 (1H,t,J=5.9 Hz), 3.85 (9H,s), 3.41–4.02 (6H,m), 2.78–2.89 (2H,m), 1.37–2.45 (12H,m)

Infrared absorption spectrum $\nu_{max}$ $cm^{-1}$ (KBr): 3424, 2928, 1634, 1584

Mass spectrometric analysis (EI) m/z: 654 ($M^+$)

Elemental analysis (% based on $C_{35}H_{40}N_2O_6Cl_2.0.5H_2O$)

Calculated: C; 63.25, H; 6.22, N; 4.21, Cl; 10.67 Found: C; 63.62, H; 6.35, N; 4.05, Cl; 10.22

Example 3

1-{-2-[(2R)-(3,4-Dichlorophenyl-4-(3,4,5-trimethoxybenzoyl)morpholin-2-yl]ethyl}spiro[((2S)-hydroxy)indane-1,4'-piperidine]

(The below-described Compound No. 138)

In 6.0 ml of dimethylacetamide, 300 mg (0.547 mmol) of 2-[(2R)-(3,4-dichlorophenyl-4-(3,4,5-trimethoxybenzoyl)morpholin-2-yl]ethanol methanesulfonate, 144 mg (0.602 mmol) of spiro[((2S)-hydroxy)indane-1,4'-piperidine]hydrochloride obtained in Referential Example 7, 138 mg (1.64 mmol) of sodium bicarbonate and 136 mg (0.821 mmol) of sodium iodide were suspended, followed by heating at 80° C. for 8 hours. Water was added to the reaction mixture and the resulting mixture was extracted with ethyl acetate. The organic layer was washed with saturated NaCl aqueous solution and dried over anhydrous magnesium sulfate. The solvent was then distilled off under reduced pressure. The residue was purified by silica gel column chromatography (silica gel; 15 g, eluent; hexane:ethyl acetate=1:1→1:3, methylene chloride:methanol=50:1→20:1), whereby 297 mg (yield: 83%) of 1-{2-[(2R)-(3,4-dichlorophenyl)-4-(3,4,5-trimethoxybenzoyl)morpholin-2-yl]ethyl}spiro[((2S)-hydroxy)indane-1,4'-piperidine]were obtained as white crystals.

Melting point: 121° C.

$[\alpha]_D^{24}$+23.6° (c=0.96, chloroform)

Nuclear magnetic resonance spectrum (400 MHz, $CDCl_3$) δ ppm: 7.67–7.16 (7H,m), 6.52 (2H,br.s), 4.40 (1H,br.s), 3.85 (9H,s), 4.04–3.37 (6H,m), 3.27 (1H,dd,J=16.7 Hz,5.3 Hz), 2.82 (1H,d,J=16.7 Hz), 2.88–2.62 (2H,m), 2.40–1.49 (10H,m)

Infrared absorption spectrum $\nu_{max}$ $cm^{-1}$ (KBr): 3427, 2933, 1634, 1584, 1465, 1428, 1415, 1330, 1237, 1128

Mass spectrometric analysis (FAB) m/z: 655 ($[M+H]^+$)

Elemental analysis (% based on $C_{35}H_{40}Cl_2N_2O_6.H_2O$)

Calculated: C; 62.41, H; 6.29, N; 4.16, Cl; 10.53 Found: C; 62.33, H; 6.27, N; 3.90, Cl; 10.49

Example 4

1-{2-[(2R)-(3,4-Dichlorophenyl)-4-(3,4,5-trimethoxybenzoyl)morpholin-2-yl]ethyl}spiro[((2S)-hydroxy)indane-1,4'-piperidine]hydrochloride (the below-described Compound No. 138-hydrochloride)

In 3.0 ml of ethanol, 297 mg (0.453 mmol) of 1-{2-[(2R)-(3,4-dichlorophenyl)-4-(3,4,5-trimethoxybenzoyl)morpholin-2-yl]ethyl}spiro[((2S)-hydroxy)indane-1,4'-piperidine] obtained in Example 3 were dissolved. To the resulting solution, 0.57 ml of 4N hydrogen chloride-1,4-dioxane solution were added under ice cooling, followed by stirring for 30 minutes. After the solvent was distilled off under reduced pressure, the residue was washed with ether, whereby 304 mg (yield: 97%) of 1-{2-[(2R)-(3,4-dichlorophenyl)-4-(3,4,5-trimethoxybenzoyl)morpholin-2-yl]ethyl}spiro[((2S)-hydroxy)indane-1,4'-piperidine] hydrochloride were obtained as white crystals.

Melting point: 169° C.

$[\alpha]_D^{24}$+30.5° (c=1.0, methanol)

Nuclear magnetic resonance spectrum (400 MHz, DMSO-$d_6$) δ ppm: 10.78 (1H,m), 7.88–7.32 (3H,m), 7.27–7.06 (4H,m), 6.76–6.61 (2H,m), 4.93–4.92 (1H,m), 4.39–4.38 (1H,m), 3.81 (6H,s), 3.70 (3H,s), 4.22–2.58 (15H, m), 2.41–1.18 (4H,m), 1.69–1.48 (1H,m)

Infrared absorption spectrum $\nu_{max}$ $cm^{-1}$ (KBr): 3360, 2937, 2561, 1635, 1584, 1464, 1427, 1330, 1237, 1127

Mass spectrometric analysis (FAB) m/z: 655 ($[M+H]^+$ free form)

Elemental analysis (% based on $C_{35}H_{40}Cl_2N_2O_6.1/2H_2O$)

Calculated: C; 59.96, H; 5.89, N; 4.00, Cl; 15.17 Found: C; 59.94, H; 5.81, N; 3.94, Cl; 15.22

The compounds which will be described below are synthesized in a similar manner to that described in the above examples.

(Ia)

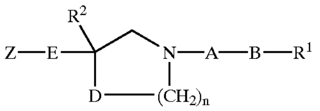

Incidentally, in the below-described table, "Ac" represents an acetyl group, "Me" represents a methyl group, "Ph" means a phenyl group, "iPr" means an isopropyl group and each substituent (in the table, described as "sub") represents the following group.

TABLE 1

| | |
|---|---|
| 1: | 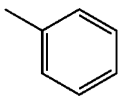 |
| 2: | 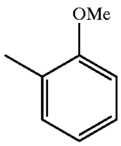 |

TABLE 1-continued

| | |
|---|---|
| 3: | 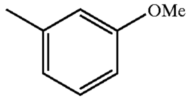 |
| 4: | 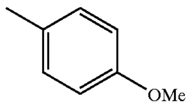 |
| 5: | 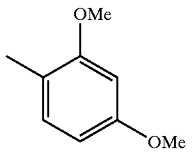 |
| 6: | 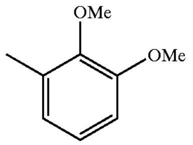 |
| 7: | 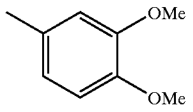 |
| 8: | 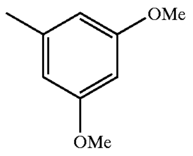 |
| 9: | 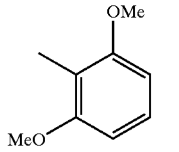 |
| 10: | 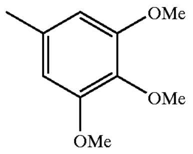 |
| 11: | 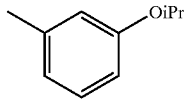 |
| 12: | 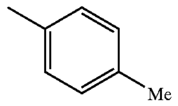 |
| 13: | 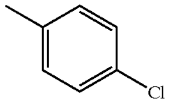 |

TABLE 1-continued
| | |
|---|---|
| 14: | 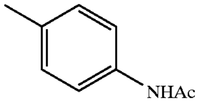 |
| 15: | 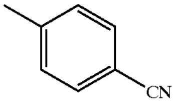 |
| 16: | 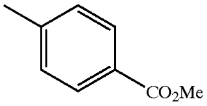 |
| 17: | 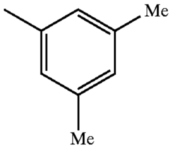 |
| 18: | 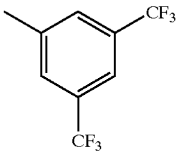 |
| 19: | 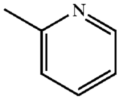 |
| 20: | 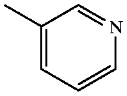 |
| 21: | 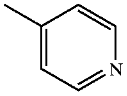 |
| 22: | 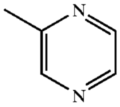 |
| 23: | 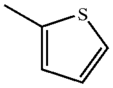 |
| 24: | 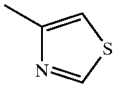 |
| 25: | 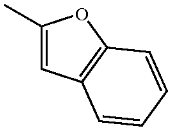 |
TABLE 1-continued
| | |
|---|---|
| 26: | 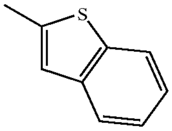 |
| 27: | 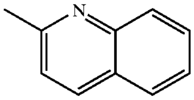 |
| 28: | 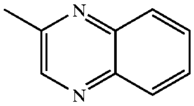 |
| 29: | 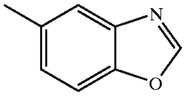 |
| 30: | 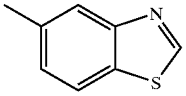 |
| 31: | 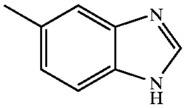 |
| 32: | 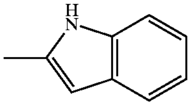 |
| 33: | 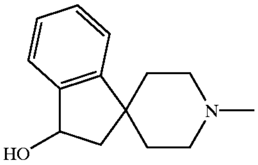 |
| 34: | 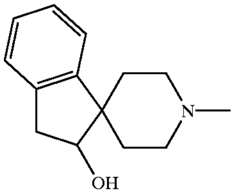 |
| 35: | 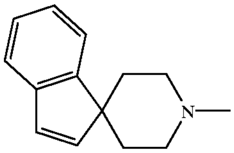 |
| 36: | 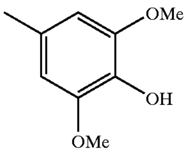 |

TABLE 1-continued

37: 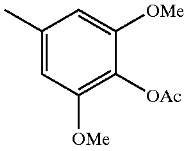

38: 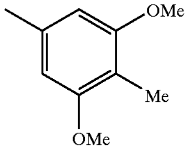

| Cpd No. | $R^1$ | $R^2$ | A | B | n | D | E | Z |
|---|---|---|---|---|---|---|---|---|
| 1 | sub. 1 | 3,4-diClPh | CO | bond | 1 | O | $CH_2CH_2$ | sub. 33 |
| 2 | sub. 2 | 3,4-diClPh | CO | bond | 1 | O | $CH_2CH_2$ | sub. 33 |
| 3 | sub. 3 | 3,4-diClPh | CO | bond | 1 | O | $CH_2CH_2$ | sub. 33 |
| 4 | sub. 4 | 3,4-diClPh | CO | bond | 1 | O | $CH_2CH_2$ | sub. 33 |
| 5 | sub. 5 | 3,4-diClPh | CO | bond | 1 | O | $CH_2CH_2$ | sub. 33 |
| 6 | sub. 6 | 3,4-diClPh | CO | bond | 1 | O | $CH_2CH_2$ | sub. 33 |
| 7 | sub. 7 | 3,4-diClPh | CO | bond | 1 | O | $CH_2CH_2$ | sub. 33 |
| 8 | sub. 8 | 3,4-diClPh | CO | bond | 1 | O | $CH_2CH_2$ | sub. 33 |
| 9 | sub. 9 | 3,4-diClPh | CO | bond | 1 | O | $CH_2CH_2$ | sub. 33 |
| 10 | sub. 10 | 3,4-diClPh | CO | bond | 1 | O | $CH_2CH_2$ | sub. 33 |
| 11 | sub. 11 | 3,4-diClPh | CO | bond | 1 | O | $CH_2CH_2$ | sub. 33 |
| 12 | sub. 12 | 3,4-diClPh | CO | bond | 1 | O | $CH_2CH_2$ | sub. 33 |
| 13 | sub. 13 | 3,4-diClPh | CO | bond | 1 | O | $CH_2CH_2$ | sub. 33 |
| 14 | sub. 14 | 3,4-diClPh | CO | bond | 1 | O | $CH_2CH_2$ | sub. 33 |
| 15 | sub. 15 | 3,4-diClPh | CO | bond | 1 | O | $CH_2CH_2$ | sub. 33 |
| 16 | sub. 16 | 3,4-diClPh | CO | bond | 1 | O | $CH_2CH_2$ | sub. 33 |
| 17 | sub. 17 | 3,4-diClPh | CO | bond | 1 | O | $CH_2CH_2$ | sub. 33 |
| 18 | sub. 18 | 3,4-diClPh | CO | bond | 1 | O | $CH_2CH_2$ | sub. 33 |
| 19 | sub. 19 | 3,4-diClPh | CO | bond | 1 | O | $CH_2CH_2$ | sub. 33 |
| 20 | sub. 20 | 3,4-diClPh | CO | bond | 1 | O | $CH_2CH_2$ | sub. 33 |
| 21 | sub. 21 | 3,4-diClPh | CO | bond | 1 | O | $CH_2CH_2$ | sub. 33 |
| 22 | sub. 22 | 3,4-diClPh | CO | bond | 1 | O | $CH_2CH_2$ | sub. 33 |
| 23 | sub. 23 | 3,4-diClPh | CO | bond | 1 | O | $CH_2CH_2$ | sub. 33 |
| 24 | sub. 24 | 3,4-diClPh | CO | bond | 1 | O | $CH_2CH_2$ | sub. 33 |
| 25 | sub. 25 | 3,4-diClPh | CO | bond | 1 | O | $CH_2CH_2$ | sub. 33 |
| 26 | sub. 26 | 3,4-diClPh | CO | bond | 1 | O | $CH_2CH_2$ | sub. 33 |
| 27 | sub. 27 | 3,4-diClPh | CO | bond | 1 | O | $CH_2CH_2$ | sub. 33 |
| 28 | sub. 28 | 3,4-diClPh | CO | bond | 1 | O | $CH_2CH_2$ | sub. 33 |
| 29 | sub. 29 | 3,4-diClPh | CO | bond | 1 | O | $CH_2CH_2$ | sub. 33 |
| 30 | sub. 30 | 3,4-diClPh | CO | bond | 1 | O | $CH_2CH_2$ | sub. 33 |
| 31 | sub. 31 | 3,4-diClPh | CO | bond | 1 | O | $CH_2CH_2$ | sub. 33 |
| 32 | sub. 32 | 3,4-diClPh | CO | bond | 1 | O | $CH_2CH_2$ | sub. 33 |
| 33 | sub. 1 | 3,4-diClPh | CO | bond | 1 | O | $CH_2CH_2$ | sub. 34 |
| 34 | sub. 2 | 3,4-diClPh | CO | bond | 1 | O | $CH_2CH_2$ | sub. 34 |
| 35 | sub. 3 | 3,4-diClPh | CO | bond | 1 | O | $CH_2CH_2$ | sub. 34 |
| 36 | sub. 4 | 3,4-diClPh | CO | bond | 1 | O | $CH_2CH_2$ | sub. 34 |
| 37 | sub. 5 | 3,4-diClPh | CO | bond | 1 | O | $CH_2CH_2$ | sub. 34 |
| 38 | sub. 6 | 3,4-diClPh | CO | bond | 1 | O | $CH_2CH_2$ | sub. 34 |
| 39 | sub. 7 | 3,4-diClPh | CO | bond | 1 | O | $CH_2CH_2$ | sub. 34 |
| 40 | sub. 8 | 3,4-diClPh | CO | bond | 1 | O | $CH_2CH_2$ | sub. 34 |
| 41 | sub. 9 | 3,4-diClPh | CO | bond | 1 | O | $CH_2CH_2$ | sub. 34 |
| 42 | sub. 10 | 3,4-diClPh | CO | bond | 1 | O | $CH_2CH_2$ | sub. 34 |
| 43 | sub. 11 | 3,4-diClPh | CO | bond | 1 | O | $CH_2CH_2$ | sub. 34 |
| 44 | sub. 12 | 3,4-diClPh | CO | bond | 1 | O | $CH_2CH_2$ | sub. 34 |
| 45 | sub. 13 | 3,4-diClPh | CO | bond | 1 | O | $CH_2CH_2$ | sub. 34 |
| 46 | sub. 14 | 3,4-diClPh | CO | bond | 1 | O | $CH_2CH_2$ | sub. 34 |
| 47 | sub. 15 | 3,4-diClPh | CO | bond | 1 | O | $CH_2CH_2$ | sub. 34 |
| 48 | sub. 16 | 3,4-diClPh | CO | bond | 1 | O | $CH_2CH_2$ | sub. 34 |
| 49 | sub. 17 | 3,4-diClPh | CO | bond | 1 | O | $CH_2CH_2$ | sub. 34 |
| 50 | sub. 18 | 3,4-diClPh | CO | bond | 1 | O | $CH_2CH_2$ | sub. 34 |
| 51 | sub. 19 | 3,4-diClPh | CO | bond | 1 | O | $CH_2CH_2$ | sub. 34 |
| 52 | sub. 20 | 3,4-diClPh | CO | bond | 1 | O | $CH_2CH_2$ | sub. 34 |
| 53 | sub. 21 | 3,4-diClPh | CO | bond | 1 | O | $CH_2CH_2$ | sub. 34 |
| 54 | sub. 22 | 3,4-diClPh | CO | bond | 1 | O | $CH_2CH_2$ | sub. 34 |
| 55 | sub. 23 | 3,4-diClPh | CO | bond | 1 | O | $CH_2CH_2$ | sub. 34 |
| 56 | sub. 24 | 3,4-diClPh | CO | bond | 1 | O | $CH_2CH_2$ | sub. 34 |
| 57 | sub. 25 | 3,4-diClPh | CO | bond | 1 | O | $CH_2CH_2$ | sub. 34 |
| 58 | sub. 26 | 3,4-diClPh | CO | bond | 1 | O | $CH_2CH_2$ | sub. 34 |
| 59 | sub. 27 | 3,4-diClPh | CO | bond | 1 | O | $CH_2CH_2$ | sub. 34 |
| 60 | sub. 28 | 3,4-diClPh | CO | bond | 1 | O | $CH_2CH_2$ | sub. 34 |
| 61 | sub. 29 | 3,4-diClPh | CO | bond | 1 | O | $CH_2CH_2$ | sub. 34 |
| 62 | sub. 30 | 3,4-diClPh | CO | bond | 1 | O | $CH_2CH_2$ | sub. 34 |
| 63 | sub. 31 | 3,4-diClPh | CO | bond | 1 | O | $CH_2CH_2$ | sub. 34 |
| 64 | sub. 32 | 3,4-diClPh | CO | bond | 1 | O | $CH_2CH_2$ | sub. 34 |
| 65 | sub. 1 | 3,4-diClPh | CO | bond | 1 | O | $CH_2CH_2$ | sub. 35 |
| 66 | sub. 2 | 3,4-diClPh | CO | bond | 1 | O | $CH_2CH_2$ | sub. 35 |
| 67 | sub. 3 | 3,4-diClPh | CO | bond | 1 | O | $CH_2CH_2$ | sub. 35 |
| 68 | sub. 4 | 3,4-diClPh | CO | bond | 1 | O | $CH_2CH_2$ | sub. 35 |
| 69 | sub. 5 | 3,4-diClPh | CO | bond | 1 | O | $CH_2CH_2$ | sub. 35 |
| 70 | sub. 6 | 3,4-diClPh | CO | bond | 1 | O | $CH_2CH_2$ | sub. 35 |
| 71 | sub. 7 | 3,4-diClPh | CO | bond | 1 | O | $CH_2CH_2$ | sub. 35 |
| 72 | sub. 8 | 3,4-diClPh | CO | bond | 1 | O | $CH_2CH_2$ | sub. 35 |
| 73 | sub. 9 | 3,4-diClPh | CO | bond | 1 | O | $CH_2CH_2$ | sub. 35 |
| 74 | sub. 10 | 3,4-diClPh | CO | bond | 1 | O | $CH_2CH_2$ | sub. 35 |
| 75 | sub. 11 | 3,4-diClPh | CO | bond | 1 | O | $CH_2CH_2$ | sub. 35 |
| 76 | sub. 12 | 3,4-diClPh | CO | bond | 1 | O | $CH_2CH_2$ | sub. 35 |
| 77 | sub. 13 | 3,4-diClPh | CO | bond | 1 | O | $CH_2CH_2$ | sub. 35 |
| 78 | sub. 14 | 3,4-diClPh | CO | bond | 1 | O | $CH_2CH_2$ | sub. 35 |
| 79 | sub. 15 | 3,4-diClPh | CO | bond | 1 | O | $CH_2CH_2$ | sub. 35 |
| 80 | sub. 16 | 3,4-diClPh | CO | bond | 1 | O | $CH_2CH_2$ | sub. 35 |
| 81 | sub. 17 | 3,4-diClPh | CO | bond | 1 | O | $CH_2CH_2$ | sub. 35 |
| 82 | sub. 18 | 3,4-diClPh | CO | bond | 1 | O | $CH_2CH_2$ | sub. 35 |
| 83 | sub. 19 | 3,4-diClPh | CO | bond | 1 | O | $CH_2CH_2$ | sub. 35 |
| 84 | sub. 20 | 3,4-diClPh | CO | bond | 1 | O | $CH_2CH_2$ | sub. 35 |
| 85 | sub. 21 | 3,4-diClPh | CO | bond | 1 | O | $CH_2CH_2$ | sub. 35 |
| 86 | sub. 22 | 3,4-diClPh | CO | bond | 1 | O | $CH_2CH_2$ | sub. 35 |
| 87 | sub. 23 | 3,4-diClPh | CO | bond | 1 | O | $CH_2CH_2$ | sub. 35 |
| 88 | sub. 24 | 3,4-diClPh | CO | bond | 1 | O | $CH_2CH_2$ | sub. 35 |
| 89 | sub. 25 | 3,4-diClPh | CO | bond | 1 | O | $CH_2CH_2$ | sub. 35 |
| 90 | sub. 26 | 3,4-diClPh | CO | bond | 1 | O | $CH_2CH_2$ | sub. 35 |
| 91 | sub. 27 | 3,4-diClPh | CO | bond | 1 | O | $CH_2CH_2$ | sub. 35 |
| 92 | sub. 28 | 3,4-diClPh | CO | bond | 1 | O | $CH_2CH_2$ | sub. 35 |
| 93 | sub. 29 | 3,4-diClPh | CO | bond | 1 | O | $CH_2CH_2$ | sub. 35 |
| 94 | sub. 30 | 3,4-diClPh | CO | bond | 1 | O | $CH_2CH_2$ | sub. 35 |
| 95 | sub. 31 | 3,4-diClPh | CO | bond | 1 | O | $CH_2CH_2$ | sub. 35 |
| 96 | sub. 32 | 3,4-diClPh | CO | bond | 1 | O | $CH_2CH_2$ | sub. 35 |
| 97 | sub. 1 | 3,4-diClPh | CO | bond | 2 | O | $CH_2CH_2$ | sub. 33 |
| 98 | sub. 2 | 3,4-diClPh | CO | bond | 2 | O | $CH_2CH_2$ | sub. 33 |
| 99 | sub. 3 | 3,4-diClPh | CO | bond | 2 | O | $CH_2CH_2$ | sub. 33 |
| 100 | sub. 4 | 3,4-diClPh | CO | bond | 2 | O | $CH_2CH_2$ | sub. 33 |
| 101 | sub. 5 | 3,4-diClPh | CO | bond | 2 | O | $CH_2CH_2$ | sub. 33 |
| 102 | sub. 6 | 3,4-diClPh | CO | bond | 2 | O | $CH_2CH_2$ | sub. 33 |
| 103 | sub. 7 | 3,4-diClPh | CO | bond | 2 | O | $CH_2CH_2$ | sub. 33 |
| 104 | sub. 8 | 3,4-diClPh | CO | bond | 2 | O | $CH_2CH_2$ | sub. 33 |
| 105 | sub. 9 | 3,4-diClPh | CO | bond | 2 | O | $CH_2CH_2$ | sub. 33 |
| 106 | sub. 10 | 3,4-diClPh | CO | bond | 2 | O | $CH_2CH_2$ | sub. 33 |
| 107 | sub. 11 | 3,4-diClPh | CO | bond | 2 | O | $CH_2CH_2$ | sub. 33 |
| 108 | sub. 12 | 3,4-diClPh | CO | bond | 2 | O | $CH_2CH_2$ | sub. 33 |
| 109 | sub. 13 | 3,4-diClPh | CO | bond | 2 | O | $CH_2CH_2$ | sub. 33 |
| 110 | sub. 14 | 3,4-diClPh | CO | bond | 2 | O | $CH_2CH_2$ | sub. 33 |
| 111 | sub. 15 | 3,4-diClPh | CO | bond | 2 | O | $CH_2CH_2$ | sub. 33 |
| 112 | sub. 16 | 3,4-diClPh | CO | bond | 2 | O | $CH_2CH_2$ | sub. 33 |
| 113 | sub. 17 | 3,4-diClPh | CO | bond | 2 | O | $CH_2CH_2$ | sub. 33 |
| 114 | sub. 18 | 3,4-diClPh | CO | bond | 2 | O | $CH_2CH_2$ | sub. 33 |
| 115 | sub. 19 | 3,4-diClPh | CO | bond | 2 | O | $CH_2CH_2$ | sub. 33 |
| 116 | sub. 20 | 3,4-diClPh | CO | bond | 2 | O | $CH_2CH_2$ | sub. 33 |
| 117 | sub. 21 | 3,4-diClPh | CO | bond | 2 | O | $CH_2CH_2$ | sub. 33 |
| 118 | sub. 22 | 3,4-diClPh | CO | bond | 2 | O | $CH_2CH_2$ | sub. 33 |
| 119 | sub. 23 | 3,4-diClPh | CO | bond | 2 | O | $CH_2CH_2$ | sub. 33 |
| 120 | sub. 24 | 3,4-diClPh | CO | bond | 2 | O | $CH_2CH_2$ | sub. 33 |
| 121 | sub. 25 | 3,4-diClPh | CO | bond | 2 | O | $CH_2CH_2$ | sub. 33 |
| 122 | sub. 26 | 3,4-diClPh | CO | bond | 2 | O | $CH_2CH_2$ | sub. 33 |
| 123 | sub. 27 | 3,4-diClPh | CO | bond | 2 | O | $CH_2CH_2$ | sub. 33 |
| 124 | sub. 28 | 3,4-diClPh | CO | bond | 2 | O | $CH_2CH_2$ | sub. 33 |
| 125 | sub. 29 | 3,4-diClPh | CO | bond | 2 | O | $CH_2CH_2$ | sub. 33 |
| 126 | sub. 30 | 3,4-diClPh | CO | bond | 2 | O | $CH_2CH_2$ | sub. 33 |
| 127 | sub. 31 | 3,4-diClPh | CO | bond | 2 | O | $CH_2CH_2$ | sub. 33 |
| 128 | sub. 32 | 3,4-diClPh | CO | bond | 2 | O | $CH_2CH_2$ | sub. 33 |
| 129 | sub. 1 | 3,4-diClPh | CO | bond | 2 | O | $CH_2CH_2$ | sub. 34 |
| 130 | sub. 2 | 3,4-diClPh | CO | bond | 2 | O | $CH_2CH_2$ | sub. 34 |
| 131 | sub. 3 | 3,4-diClPh | CO | bond | 2 | O | $CH_2CH_2$ | sub. 34 |
| 132 | sub. 4 | 3,4-diClPh | CO | bond | 2 | O | $CH_2CH_2$ | sub. 34 |
| 133 | sub. 5 | 3,4-diClPh | CO | bond | 2 | O | $CH_2CH_2$ | sub. 34 |
| 134 | sub. 6 | 3,4-diClPh | CO | bond | 2 | O | $CH_2CH_2$ | sub. 34 |
| 135 | sub. 7 | 3,4-diClPh | CO | bond | 2 | O | $CH_2CH_2$ | sub. 34 |
| 136 | sub. 8 | 3,4-diClPh | CO | bond | 2 | O | $CH_2CH_2$ | sub. 34 |
| 137 | sub. 9 | 3,4-diClPh | CO | bond | 2 | O | $CH_2CH_2$ | sub. 34 |
| 138 | sub. 10 | 3,4-diClPh | CO | bond | 2 | O | $CH_2CH_2$ | sub. 34 |

TABLE 1-continued

| | | | | | | | | |
|---|---|---|---|---|---|---|---|---|
| 139 | sub. 11 | 3,4-diClPh | CO | bond | 2 | O | $CH_2CH_2$ | sub. 34 |
| 140 | sub. 12 | 3,4-diClPh | CO | bond | 2 | O | $CH_2CH_2$ | sub. 34 |
| 141 | sub. 13 | 3,4-diClPh | CO | bond | 2 | O | $CH_2CH_2$ | sub. 34 |
| 142 | sub. 14 | 3,4-diClPh | CO | bond | 2 | O | $CH_2CH_2$ | sub. 34 |
| 143 | sub. 15 | 3,4-diClPh | CO | bond | 2 | O | $CH_2CH_2$ | sub. 34 |
| 144 | sub. 16 | 3,4-diClPh | CO | bond | 2 | O | $CH_2CH_2$ | sub. 34 |
| 145 | sub. 17 | 3,4-diClPh | CO | bond | 2 | O | $CH_2CH_2$ | sub. 34 |
| 146 | sub. 18 | 3,4-diClPh | CO | bond | 2 | O | $CH_2CH_2$ | sub. 34 |
| 147 | sub. 19 | 3,4-diClPh | CO | bond | 2 | O | $CH_2CH_2$ | sub. 34 |
| 148 | sub. 20 | 3,4-diClPh | CO | bond | 2 | O | $CH_2CH_2$ | sub. 34 |
| 149 | sub. 21 | 3,4-diClPh | CO | bond | 2 | O | $CH_2CH_2$ | sub. 34 |
| 150 | sub. 22 | 3,4-diClPh | CO | bond | 2 | O | $CH_2CH_2$ | sub. 34 |
| 151 | sub. 23 | 3,4-diClPh | CO | bond | 2 | O | $CH_2CH_2$ | sub. 34 |
| 152 | sub. 24 | 3,4-diClPh | CO | bond | 2 | O | $CH_2CH_2$ | sub. 34 |
| 153 | sub. 25 | 3,4-diClPh | CO | bond | 2 | O | $CH_2CH_2$ | sub. 34 |
| 154 | sub. 26 | 3,4-diClPh | CO | bond | 2 | O | $CH_2CH_2$ | sub. 34 |
| 155 | sub. 27 | 3,4-diClPh | CO | bond | 2 | O | $CH_2CH_2$ | sub. 34 |
| 156 | sub. 28 | 3,4-diClPh | CO | bond | 2 | O | $CH_2CH_2$ | sub. 34 |
| 157 | sub. 29 | 3,4-diClPh | CO | bond | 2 | O | $CH_2CH_2$ | sub. 34 |
| 158 | sub. 30 | 3,4-diClPh | CO | bond | 2 | O | $CH_2CH_2$ | sub. 34 |
| 159 | sub. 31 | 3,4-diClPh | CO | bond | 2 | O | $CH_2CH_2$ | sub. 34 |
| 160 | sub. 32 | 3,4-diClPh | CO | bond | 2 | O | $CH_2CH_2$ | sub. 34 |
| 161 | sub. 1 | 3,4-diClPh | CO | bond | 2 | O | $CH_2CH_2$ | sub. 35 |
| 162 | sub. 2 | 3,4-diClPh | CO | bond | 2 | O | $CH_2CH_2$ | sub. 35 |
| 163 | sub. 3 | 3,4-diClPh | CO | bond | 2 | O | $CH_2CH_2$ | sub. 35 |
| 164 | sub. 4 | 3,4-diClPh | CO | bond | 2 | O | $CH_2CH_2$ | sub. 35 |
| 165 | sub. 5 | 3,4-diClPh | CO | bond | 2 | O | $CH_2CH_2$ | sub. 35 |
| 166 | sub. 6 | 3,4-diClPh | CO | bond | 2 | O | $CH_2CH_2$ | sub. 35 |
| 167 | sub. 7 | 3,4-diClPh | CO | bond | 2 | O | $CH_2CH_2$ | sub. 35 |
| 168 | sub. 8 | 3,4-diClPh | CO | bond | 2 | O | $CH_2CH_2$ | sub. 35 |
| 169 | sub. 9 | 3,4-diClPh | CO | bond | 2 | O | $CH_2CH_2$ | sub. 35 |
| 170 | sub. 10 | 3,4-diClPh | CO | bond | 2 | O | $CH_2CH_2$ | sub. 35 |
| 171 | sub. 11 | 3,4-diClPh | CO | bond | 2 | O | $CH_2CH_2$ | sub. 35 |
| 172 | sub. 12 | 3,4-diClPh | CO | bond | 2 | O | $CH_2CH_2$ | sub. 35 |
| 173 | sub. 13 | 3,4-diClPh | CO | bond | 2 | O | $CH_2CH_2$ | sub. 35 |
| 174 | sub. 14 | 3,4-diClPh | CO | bond | 2 | O | $CH_2CH_2$ | sub. 35 |
| 175 | sub. 15 | 3,4-diClPh | CO | bond | 2 | O | $CH_2CH_2$ | sub. 35 |
| 176 | sub. 16 | 3,4-diClPh | CO | bond | 2 | O | $CH_2CH_2$ | sub. 35 |
| 177 | sub. 17 | 3,4-diClPh | CO | bond | 2 | O | $CH_2CH_2$ | sub. 35 |
| 178 | sub. 18 | 3,4-diClPh | CO | bond | 2 | O | $CH_2CH_2$ | sub. 35 |
| 179 | sub. 19 | 3,4-diClPh | CO | bond | 2 | O | $CH_2CH_2$ | sub. 35 |
| 180 | sub. 20 | 3,4-diClPh | CO | bond | 2 | O | $CH_2CH_2$ | sub. 35 |
| 181 | sub. 21 | 3,4-diClPh | CO | bond | 2 | O | $CH_2CH_2$ | sub. 35 |
| 182 | sub. 22 | 3,4-diClPh | CO | bond | 2 | O | $CH_2CH_2$ | sub. 35 |
| 183 | sub. 23 | 3,4-diClPh | CO | bond | 2 | O | $CH_2CH_2$ | sub. 35 |
| 184 | sub. 24 | 3,4-diClPh | CO | bond | 2 | O | $CH_2CH_2$ | sub. 35 |
| 185 | sub. 25 | 3,4-diClPh | CO | bond | 2 | O | $CH_2CH_2$ | sub. 35 |
| 186 | sub. 26 | 3,4-diClPh | CO | bond | 2 | O | $CH_2CH_2$ | sub. 35 |
| 187 | sub. 27 | 3,4-diClPh | CO | bond | 2 | O | $CH_2CH_2$ | sub. 35 |
| 188 | sub. 28 | 3,4-diClPh | CO | bond | 2 | O | $CH_2CH_2$ | sub. 35 |
| 189 | sub. 29 | 3,4-diClPh | CO | bond | 2 | O | $CH_2CH_2$ | sub. 35 |
| 190 | sub. 30 | 3,4-diClPh | CO | bond | 2 | O | $CH_2CH_2$ | sub. 35 |
| 191 | sub. 31 | 3,4-diClPh | CO | bond | 2 | O | $CH_2CH_2$ | sub. 35 |
| 192 | sub. 32 | 3,4-diClPh | CO | bond | 2 | O | $CH_2CH_2$ | sub. 35 |
| 193 | sub. 1 | 3,4-diFPh | CO | bond | 2 | O | $CH_2CH_2$ | sub. 33 |
| 194 | sub. 2 | 3,4-diFPh | CO | bond | 2 | O | $CH_2CH_2$ | sub. 33 |
| 195 | sub. 3 | 3,4-diFPh | CO | bond | 2 | O | $CH_2CH_2$ | sub. 33 |
| 196 | sub. 4 | 3,4-diFPh | CO | bond | 2 | O | $CH_2CH_2$ | sub. 33 |
| 197 | sub. 5 | 3,4-diFPh | CO | bond | 2 | O | $CH_2CH_2$ | sub. 33 |
| 198 | sub. 6 | 3,4-diFPh | CO | bond | 2 | O | $CH_2CH_2$ | sub. 33 |
| 199 | sub. 7 | 3,4-diFPh | CO | bond | 2 | O | $CH_2CH_2$ | sub. 33 |
| 200 | sub. 8 | 3,4-diFPh | CO | bond | 2 | O | $CH_2CH_2$ | sub. 33 |
| 201 | sub. 9 | 3,4-diFPh | CO | bond | 2 | O | $CH_2CH_2$ | sub. 33 |
| 202 | sub. 10 | 3,4-diFPh | CO | bond | 2 | O | $CH_2CH_2$ | sub. 33 |
| 203 | sub. 11 | 3,4-diFPh | CO | bond | 2 | O | $CH_2CH_2$ | sub. 33 |
| 204 | sub. 12 | 3,4-diFPh | CO | bond | 2 | O | $CH_2CH_2$ | sub. 33 |
| 205 | sub. 13 | 3,4-diFPh | CO | bond | 2 | O | $CH_2CH_2$ | sub. 33 |
| 206 | sub. 14 | 3,4-diFPh | CO | bond | 2 | O | $CH_2CH_2$ | sub. 33 |
| 207 | sub. 15 | 3,4-diFPh | CO | bond | 2 | O | $CH_2CH_2$ | sub. 33 |
| 208 | sub. 16 | 3,4-diFPh | CO | bond | 2 | O | $CH_2CH_2$ | sub. 33 |
| 209 | sub. 17 | 3,4-diFPh | CO | bond | 2 | O | $CH_2CH_2$ | sub. 33 |
| 210 | sub. 18 | 3,4-diFPh | CO | bond | 2 | O | $CH_2CH_2$ | sub. 33 |
| 211 | sub. 19 | 3,4-diFPh | CO | bond | 2 | O | $CH_2CH_2$ | sub. 33 |
| 212 | sub. 20 | 3,4-diFPh | CO | bond | 2 | O | $CH_2CH_2$ | sub. 33 |
| 213 | sub. 21 | 3,4-diFPh | CO | bond | 2 | O | $CH_2CH_2$ | sub. 33 |
| 214 | sub. 22 | 3,4-diFPh | CO | bond | 2 | O | $CH_2CH_2$ | sub. 33 |
| 215 | sub. 23 | 3,4-diFPh | CO | bond | 2 | O | $CH_2CH_2$ | sub. 33 |
| 216 | sub. 24 | 3,4-diFPh | CO | bond | 2 | O | $CH_2CH_2$ | sub. 33 |
| 217 | sub. 25 | 3,4-diFPh | CO | bond | 2 | O | $CH_2CH_2$ | sub. 33 |

TABLE 1-continued

| | | | | | | | | |
|---|---|---|---|---|---|---|---|---|
| 218 | sub. 26 | 3,4-diFPh | CO | bond | 2 | O | $CH_2CH_2$ | sub. 33 |
| 219 | sub. 27 | 3,4-diFPh | CO | bond | 2 | O | $CH_2CH_2$ | sub. 33 |
| 220 | sub. 28 | 3,4-diFPh | CO | bond | 2 | O | $CH_2CH_2$ | sub. 33 |
| 221 | sub. 29 | 3,4-diFPh | CO | bond | 2 | O | $CH_2CH_2$ | sub. 33 |
| 222 | sub. 30 | 3,4-diFPh | CO | bond | 2 | O | $CH_2CH_2$ | sub. 33 |
| 223 | sub. 31 | 3,4-diFPh | CO | bond | 2 | O | $CH_2CH_2$ | sub. 33 |
| 224 | sub. 32 | 3,4-diFPh | CO | bond | 2 | O | $CH_2CH_2$ | sub. 33 |
| 225 | sub. 1 | 3,4-diFPh | CO | bond | 2 | O | $CH_2CH_2$ | sub. 34 |
| 226 | sub. 2 | 3,4-diFPh | CO | bond | 2 | O | $CH_2CH_2$ | sub. 34 |
| 227 | sub. 3 | 3,4-diFPh | CO | bond | 2 | O | $CH_2CH_2$ | sub. 34 |
| 228 | sub. 4 | 3,4-diFPh | CO | bond | 2 | O | $CH_2CH_2$ | sub. 34 |
| 229 | sub. 5 | 3,4-diFPh | CO | bond | 2 | O | $CH_2CH_2$ | sub. 34 |
| 230 | sub. 6 | 3,4-diFPh | CO | bond | 2 | O | $CH_2CH_2$ | sub. 34 |
| 231 | sub. 7 | 3,4-diFPh | CO | bond | 2 | O | $CH_2CH_2$ | sub. 34 |
| 232 | sub. 8 | 3,4-diFPh | CO | bond | 2 | O | $CH_2CH_2$ | sub. 34 |
| 233 | sub. 9 | 3,4-diFPh | CO | bond | 2 | O | $CH_2CH_2$ | sub. 34 |
| 234 | sub. 10 | 3,4-diFPh | CO | bond | 2 | O | $CH_2CH_2$ | sub. 34 |
| 235 | sub. 11 | 3,4-diFPh | CO | bond | 2 | O | $CH_2CH_2$ | sub. 34 |
| 236 | sub. 12 | 3,4-diFPh | CO | bond | 2 | O | $CH_2CH_2$ | sub. 34 |
| 237 | sub. 13 | 3,4-diFPh | CO | bond | 2 | O | $CH_2CH_2$ | sub. 34 |
| 238 | sub. 14 | 3,4-diFPh | CO | bond | 2 | O | $CH_2CH_2$ | sub. 34 |
| 239 | sub. 15 | 3,4-diFPh | CO | bond | 2 | O | $CH_2CH_2$ | sub. 34 |
| 240 | sub. 16 | 3,4-diFPh | CO | bond | 2 | O | $CH_2CH_2$ | sub. 34 |
| 241 | sub. 17 | 3,4-diFPh | CO | bond | 2 | O | $CH_2CH_2$ | sub. 34 |
| 242 | sub. 18 | 3,4-diFPh | CO | bond | 2 | O | $CH_2CH_2$ | sub. 34 |
| 243 | sub. 19 | 3,4-diFPh | CO | bond | 2 | O | $CH_2CH_2$ | sub. 34 |
| 244 | sub. 20 | 3,4-diFPh | CO | bond | 2 | O | $CH_2CH_2$ | sub. 34 |
| 245 | sub. 21 | 3,4-diFPh | CO | bond | 2 | O | $CH_2CH_2$ | sub. 34 |
| 246 | sub. 22 | 3,4-diFPh | CO | bond | 2 | O | $CH_2CH_2$ | sub. 34 |
| 247 | sub. 23 | 3,4-diFPh | CO | bond | 2 | O | $CH_2CH_2$ | sub. 34 |
| 248 | sub. 24 | 3,4-diFPh | CO | bond | 2 | O | $CH_2CH_2$ | sub. 34 |
| 249 | sub. 25 | 3,4-diFPh | CO | bond | 2 | O | $CH_2CH_2$ | sub. 34 |
| 250 | sub. 26 | 3,4-diFPh | CO | bond | 2 | O | $CH_2CH_2$ | sub. 34 |
| 251 | sub. 27 | 3,4-diFPh | CO | bond | 2 | O | $CH_2CH_2$ | sub. 34 |
| 252 | sub. 28 | 3,4-diFPh | CO | bond | 2 | O | $CH_2CH_2$ | sub. 34 |
| 253 | sub. 29 | 3,4-diFPh | CO | bond | 2 | O | $CH_2CH_2$ | sub. 34 |
| 254 | sub. 30 | 3,4-diFPh | CO | bond | 2 | O | $CH_2CH_2$ | sub. 34 |
| 255 | sub. 31 | 3,4-diFPh | CO | bond | 2 | O | $CH_2CH_2$ | sub. 34 |
| 256 | sub. 32 | 3,4-diFPh | CO | bond | 2 | O | $CH_2CH_2$ | sub. 34 |
| 257 | sub. 1 | 3,4-diFPh | CO | bond | 2 | O | $CH_2CH_2$ | sub. 35 |
| 258 | sub. 2 | 3,4-diFPh | CO | bond | 2 | O | $CH_2CH_2$ | sub. 35 |
| 259 | sub. 3 | 3,4-diFPh | CO | bond | 2 | O | $CH_2CH_2$ | sub. 35 |
| 260 | sub. 4 | 3,4-diFPh | CO | bond | 2 | O | $CH_2CH_2$ | sub. 35 |
| 261 | sub. 5 | 3,4-diFPh | CO | bond | 2 | O | $CH_2CH_2$ | sub. 35 |
| 262 | sub. 6 | 3,4-diFPh | CO | bond | 2 | O | $CH_2CH_2$ | sub. 35 |
| 263 | sub. 7 | 3,4-diFPh | CO | bond | 2 | O | $CH_2CH_2$ | sub. 35 |
| 264 | sub. 8 | 3,4-diFPh | CO | bond | 2 | O | $CH_2CH_2$ | sub. 35 |
| 265 | sub. 9 | 3,4-diFPh | CO | bond | 2 | O | $CH_2CH_2$ | sub. 35 |
| 266 | sub. 10 | 3,4-diFPh | CO | bond | 2 | O | $CH_2CH_2$ | sub. 35 |
| 267 | sub. 11 | 3,4-diFPh | CO | bond | 2 | O | $CH_2CH_2$ | sub. 35 |
| 268 | sub. 12 | 3,4-diFPh | CO | bond | 2 | O | $CH_2CH_2$ | sub. 35 |
| 269 | sub. 13 | 3,4-diFPh | CO | bond | 2 | O | $CH_2CH_2$ | sub. 35 |
| 270 | sub. 14 | 3,4-diFPh | CO | bond | 2 | O | $CH_2CH_2$ | sub. 35 |
| 271 | sub. 15 | 3,4-diFPh | CO | bond | 2 | O | $CH_2CH_2$ | sub. 35 |
| 272 | sub. 16 | 3,4-diFPh | CO | bond | 2 | O | $CH_2CH_2$ | sub. 35 |
| 273 | sub. 17 | 3,4-diFPh | CO | bond | 2 | O | $CH_2CH_2$ | sub. 35 |
| 274 | sub. 18 | 3,4-diFPh | CO | bond | 2 | O | $CH_2CH_2$ | sub. 35 |
| 275 | sub. 19 | 3,4-diFPh | CO | bond | 2 | O | $CH_2CH_2$ | sub. 35 |
| 276 | sub. 20 | 3,4-diFPh | CO | bond | 2 | O | $CH_2CH_2$ | sub. 35 |
| 277 | sub. 21 | 3,4-diFPh | CO | bond | 2 | O | $CH_2CH_2$ | sub. 35 |
| 278 | sub. 22 | 3,4-diFPh | CO | bond | 2 | O | $CH_2CH_2$ | sub. 35 |
| 279 | sub. 23 | 3,4-diFPh | CO | bond | 2 | O | $CH_2CH_2$ | sub. 35 |
| 280 | sub. 24 | 3,4-diFPh | CO | bond | 2 | O | $CH_2CH_2$ | sub. 35 |
| 281 | sub. 25 | 3,4-diFPh | CO | bond | 2 | O | $CH_2CH_2$ | sub. 35 |
| 282 | sub. 26 | 3,4-diFPh | CO | bond | 2 | O | $CH_2CH_2$ | sub. 35 |
| 283 | sub. 27 | 3,4-diFPh | CO | bond | 2 | O | $CH_2CH_2$ | sub. 35 |
| 284 | sub. 28 | 3,4-diFPh | CO | bond | 2 | O | $CH_2CH_2$ | sub. 35 |
| 285 | sub. 29 | 3,4-diFPh | CO | bond | 2 | O | $CH_2CH_2$ | sub. 35 |
| 286 | sub. 30 | 3,4-diFPh | CO | bond | 2 | O | $CH_2CH_2$ | sub. 35 |
| 287 | sub. 31 | 3,4-diFPh | CO | bond | 2 | O | $CH_2CH_2$ | sub. 35 |
| 288 | sub. 32 | 3,4-diFPh | CO | bond | 2 | O | $CH_2CH_2$ | sub. 35 |
| 289 | sub. 1 | 4-ClPh | CO | bond | 2 | O | $CH_2CH_2$ | sub. 33 |
| 290 | sub. 2 | 4-ClPh | CO | bond | 2 | O | $CH_2CH_2$ | sub. 33 |
| 291 | sub. 3 | 4-ClPh | CO | bond | 2 | O | $CH_2CH_2$ | sub. 33 |
| 292 | sub. 4 | 4-ClPh | CO | bond | 2 | O | $CH_2CH_2$ | sub. 33 |
| 293 | sub. 5 | 4-ClPh | CO | bond | 2 | O | $CH_2CH_2$ | sub. 33 |
| 294 | sub. 6 | 4-ClPh | CO | bond | 2 | O | $CH_2CH_2$ | sub. 33 |
| 295 | sub. 7 | 4-ClPh | CO | bond | 2 | O | $CH_2CH_2$ | sub. 33 |
| 296 | sub. 8 | 4-ClPh | CO | bond | 2 | O | $CH_2CH_2$ | sub. 33 |

TABLE 1-continued

| | | | | | | | | |
|---|---|---|---|---|---|---|---|---|
| 297 | sub. 9 | 4-ClPh | CO | bond | 2 | O | $CH_2CH_2$ | sub. 33 |
| 298 | sub. 10 | 4-ClPh | CO | bond | 2 | O | $CH_2CH_2$ | sub. 33 |
| 299 | sub. 11 | 4-ClPh | CO | bond | 2 | O | $CH_2CH_2$ | sub. 33 |
| 300 | sub. 12 | 4-ClPh | CO | bond | 2 | O | $CH_2CH_2$ | sub. 33 |
| 301 | sub. 13 | 4-ClPh | CO | bond | 2 | O | $CH_2CH_2$ | sub. 33 |
| 302 | sub. 14 | 4-ClPh | CO | bond | 2 | O | $CH_2CH_2$ | sub. 33 |
| 303 | sub. 15 | 4-ClPh | CO | bond | 2 | O | $CH_2CH_2$ | sub. 33 |
| 304 | sub. 16 | 4-ClPh | CO | bond | 2 | O | $CH_2CH_2$ | sub. 33 |
| 305 | sub. 17 | 4-ClPh | CO | bond | 2 | O | $CH_2CH_2$ | sub. 33 |
| 306 | sub. 18 | 4-ClPh | CO | bond | 2 | O | $CH_2CH_2$ | sub. 33 |
| 307 | sub. 19 | 4-ClPh | CO | bond | 2 | O | $CH_2CH_2$ | sub. 33 |
| 308 | sub. 20 | 4-ClPh | CO | bond | 2 | O | $CH_2CH_2$ | sub. 33 |
| 309 | sub. 21 | 4-ClPh | CO | bond | 2 | O | $CH_2CH_2$ | sub. 33 |
| 310 | sub. 22 | 4-ClPh | CO | bond | 2 | O | $CH_2CH_2$ | sub. 33 |
| 311 | sub. 23 | 4-ClPh | CO | bond | 2 | O | $CH_2CH_2$ | sub. 33 |
| 312 | sub. 24 | 4-ClPh | CO | bond | 2 | O | $CH_2CH_2$ | sub. 33 |
| 313 | sub. 25 | 4-ClPh | CO | bond | 2 | O | $CH_2CH_2$ | sub. 33 |
| 314 | sub. 26 | 4-ClPh | CO | bond | 2 | O | $CH_2CH_2$ | sub. 33 |
| 315 | sub. 27 | 4-ClPh | CO | bond | 2 | O | $CH_2CH_2$ | sub. 33 |
| 316 | sub. 28 | 4-ClPh | CO | bond | 2 | O | $CH_2CH_2$ | sub. 33 |
| 317 | sub. 29 | 4-ClPh | CO | bond | 2 | O | $CH_2CH_2$ | sub. 33 |
| 318 | sub. 30 | 4-ClPh | CO | bond | 2 | O | $CH_2CH_2$ | sub. 33 |
| 319 | sub. 31 | 4-ClPh | CO | bond | 2 | O | $CH_2CH_2$ | sub. 33 |
| 320 | sub. 32 | 4-ClPh | CO | bond | 2 | O | $CH_2CH_2$ | sub. 33 |
| 321 | sub. 1 | 4-ClPh | CO | bond | 2 | O | $CH_2CH_2$ | sub. 34 |
| 322 | sub. 2 | 4-ClPh | CO | bond | 2 | O | $CH_2CH_2$ | sub. 34 |
| 323 | sub. 3 | 4-ClPh | CO | bond | 2 | O | $CH_2CH_2$ | sub. 34 |
| 324 | sub. 4 | 4-ClPh | CO | bond | 2 | O | $CH_2CH_2$ | sub. 34 |
| 325 | sub. 5 | 4-ClPh | CO | bond | 2 | O | $CH_2CH_2$ | sub. 34 |
| 326 | sub. 6 | 4-ClPh | CO | bond | 2 | O | $CH_2CH_2$ | sub. 34 |
| 327 | sub. 7 | 4-ClPh | CO | bond | 2 | O | $CH_2CH_2$ | sub. 34 |
| 328 | sub. 8 | 4-ClPh | CO | bond | 2 | O | $CH_2CH_2$ | sub. 34 |
| 329 | sub. 9 | 4-ClPh | CO | bond | 2 | O | $CH_2CH_2$ | sub. 34 |
| 330 | sub. 10 | 4-ClPh | CO | bond | 2 | O | $CH_2CH_2$ | sub. 34 |
| 331 | sub. 11 | 4-ClPh | CO | bond | 2 | O | $CH_2CH_2$ | sub. 34 |
| 332 | sub. 12 | 4-ClPh | CO | bond | 2 | O | $CH_2CH_2$ | sub. 34 |
| 333 | sub. 13 | 4-ClPh | CO | bond | 2 | O | $CH_2CH_2$ | sub. 34 |
| 334 | sub. 14 | 4-ClPh | CO | bond | 2 | O | $CH_2CH_2$ | sub. 34 |
| 335 | sub. 15 | 4-ClPh | CO | bond | 2 | O | $CH_2CH_2$ | sub. 34 |
| 336 | sub. 16 | 4-ClPh | CO | bond | 2 | O | $CH_2CH_2$ | sub. 34 |
| 337 | sub. 17 | 4-ClPh | CO | bond | 2 | O | $CH_2CH_2$ | sub. 34 |
| 338 | sub. 18 | 4-ClPh | CO | bond | 2 | O | $CH_2CH_2$ | sub. 34 |
| 339 | sub. 19 | 4-ClPh | CO | bond | 2 | O | $CH_2CH_2$ | sub. 34 |
| 340 | sub. 20 | 4-ClPh | CO | bond | 2 | O | $CH_2CH_2$ | sub. 34 |
| 341 | sub. 21 | 4-ClPh | CO | bond | 2 | O | $CH_2CH_2$ | sub. 34 |
| 342 | sub. 22 | 4-ClPh | CO | bond | 2 | O | $CH_2CH_2$ | sub. 34 |
| 343 | sub. 23 | 4-ClPh | CO | bond | 2 | O | $CH_2CH_2$ | sub. 34 |
| 344 | sub. 24 | 4-ClPh | CO | bond | 2 | O | $CH_2CH_2$ | sub. 34 |
| 345 | sub. 25 | 4-ClPh | CO | bond | 2 | O | $CH_2CH_2$ | sub. 34 |
| 346 | sub. 26 | 4-ClPh | CO | bond | 2 | O | $CH_2CH_2$ | sub. 34 |
| 347 | sub. 27 | 4-ClPh | CO | bond | 2 | O | $CH_2CH_2$ | sub. 34 |
| 348 | sub. 28 | 4-ClPh | CO | bond | 2 | O | $CH_2CH_2$ | sub. 34 |
| 349 | sub. 29 | 4-ClPh | CO | bond | 2 | O | $CH_2CH_2$ | sub. 34 |
| 350 | sub. 30 | 4-ClPh | CO | bond | 2 | O | $CH_2CH_2$ | sub. 34 |
| 351 | sub. 31 | 4-ClPh | CO | bond | 2 | O | $CH_2CH_2$ | sub. 34 |
| 352 | sub. 32 | 4-ClPh | CO | bond | 2 | O | $CH_2CH_2$ | sub. 34 |
| 353 | sub. 1 | 4-ClPh | CO | bond | 2 | O | $CH_2CH_2$ | sub. 35 |
| 354 | sub. 2 | 4-ClPh | CO | bond | 2 | O | $CH_2CH_2$ | sub. 35 |
| 355 | sub. 3 | 4-ClPh | CO | bond | 2 | O | $CH_2CH_2$ | sub. 35 |
| 356 | sub. 4 | 4-ClPh | CO | bond | 2 | O | $CH_2CH_2$ | sub. 35 |
| 357 | sub. 5 | 4-ClPh | CO | bond | 2 | O | $CH_2CH_2$ | sub. 35 |
| 358 | sub. 6 | 4-ClPh | CO | bond | 2 | O | $CH_2CH_2$ | sub. 35 |
| 359 | sub. 7 | 4-ClPh | CO | bond | 2 | O | $CH_2CH_2$ | sub. 35 |
| 360 | sub. 8 | 4-ClPh | CO | bond | 2 | O | $CH_2CH_2$ | sub. 35 |
| 361 | sub. 9 | 4-ClPh | CO | bond | 2 | O | $CH_2CH_2$ | sub. 35 |
| 362 | sub. 10 | 4-ClPh | CO | bond | 2 | O | $CH_2CH_2$ | sub. 35 |
| 363 | sub. 11 | 4-ClPh | CO | bond | 2 | O | $CH_2CH_2$ | sub. 35 |
| 364 | sub. 12 | 4-ClPh | CO | bond | 2 | O | $CH_2CH_2$ | sub. 35 |
| 365 | sub. 13 | 4-ClPh | CO | bond | 2 | O | $CH_2CH_2$ | sub. 35 |
| 366 | sub. 14 | 4-ClPh | CO | bond | 2 | O | $CH_2CH_2$ | sub. 35 |
| 367 | sub. 15 | 4-ClPh | CO | bond | 2 | O | $CH_2CH_2$ | sub. 35 |
| 368 | sub. 16 | 4-ClPh | CO | bond | 2 | O | $CH_2CH_2$ | sub. 35 |
| 369 | sub. 17 | 4-ClPh | CO | bond | 2 | O | $CH_2CH_2$ | sub. 35 |
| 370 | sub. 18 | 4-ClPh | CO | bond | 2 | O | $CH_2CH_2$ | sub. 35 |
| 371 | sub. 19 | 4-ClPh | CO | bond | 2 | O | $CH_2CH_2$ | sub. 35 |
| 372 | sub. 20 | 4-ClPh | CO | bond | 2 | O | $CH_2CH_2$ | sub. 35 |
| 373 | sub. 21 | 4-ClPh | CO | bond | 2 | O | $CH_2CH_2$ | sub. 35 |
| 374 | sub. 22 | 4-ClPh | CO | bond | 2 | O | $CH_2CH_2$ | sub. 35 |
| 375 | sub. 23 | 4-ClPh | CO | bond | 2 | O | $CH_2CH_2$ | sub. 35 |
| 376 | sub. 24 | 4-ClPh | CO | bond | 2 | O | $CH_2CH_2$ | sub. 35 |
| 377 | sub. 25 | 4-ClPh | CO | bond | 2 | O | $CH_2CH_2$ | sub. 35 |
| 378 | sub. 26 | 4-ClPh | CO | bond | 2 | O | $CH_2CH_2$ | sub. 35 |
| 379 | sub. 27 | 4-ClPh | CO | bond | 2 | O | $CH_2CH_2$ | sub. 35 |
| 380 | sub. 28 | 4-ClPh | CO | bond | 2 | O | $CH_2CH_2$ | sub. 35 |
| 381 | sub. 29 | 4-ClPh | CO | bond | 2 | O | $CH_2CH_2$ | sub. 35 |
| 382 | sub. 30 | 4-ClPh | CO | bond | 2 | O | $CH_2CH_2$ | sub. 35 |
| 383 | sub. 31 | 4-ClPh | CO | bond | 2 | O | $CH_2CH_2$ | sub. 35 |
| 384 | sub. 32 | 4-ClPh | CO | bond | 2 | O | $CH_2CH_2$ | sub. 35 |

TABLE 2

| Cpd No. | $R^1$ | $R^2$ | A | B | n | D | E | Z |
|---|---|---|---|---|---|---|---|---|
| 385 | sub. 1 | 4-FPh | CO | bond | 2 | O | $CH_2CH_2$ | sub. 33 |
| 386 | sub. 2 | 4-FPh | CO | bond | 2 | O | $CH_2CH_2$ | sub. 33 |
| 387 | sub. 3 | 4-FPh | CO | bond | 2 | O | $CH_2CH_2$ | sub. 33 |
| 388 | sub. 4 | 4-FPh | CO | bond | 2 | O | $CH_2CH_2$ | sub. 33 |
| 389 | sub. 5 | 4-FPh | CO | bond | 2 | O | $CH_2CH_2$ | sub. 33 |
| 390 | sub. 6 | 4-FPh | CO | bond | 2 | O | $CH_2CH_2$ | sub. 33 |
| 391 | sub. 7 | 4-FPh | CO | bond | 2 | O | $CH_2CH_2$ | sub. 33 |
| 392 | sub. 8 | 4-FPh | CO | bond | 2 | O | $CH_2CH_2$ | sub. 33 |
| 393 | sub. 9 | 4-FPh | CO | bond | 2 | O | $CH_2CH_2$ | sub. 33 |
| 394 | sub. 10 | 4-FPh | CO | bond | 2 | O | $CH_2CH_2$ | sub. 33 |
| 395 | sub. 11 | 4-FPh | CO | bond | 2 | O | $CH_2CH_2$ | sub. 33 |
| 396 | sub. 12 | 4-FPh | CO | bond | 2 | O | $CH_2CH_2$ | sub. 33 |
| 397 | sub. 13 | 4-FPh | CO | bond | 2 | O | $CH_2CH_2$ | sub. 33 |
| 398 | sub. 14 | 4-FPh | CO | bond | 2 | O | $CH_2CH_2$ | sub. 33 |
| 399 | sub. 15 | 4-FPh | CO | bond | 2 | O | $CH_2CH_2$ | sub. 33 |
| 400 | sub. 16 | 4-FPh | CO | bond | 2 | O | $CH_2CH_2$ | sub. 33 |
| 401 | sub. 17 | 4-FPh | CO | bond | 2 | O | $CH_2CH_2$ | sub. 33 |
| 402 | sub. 18 | 4-FPh | CO | bond | 2 | O | $CH_2CH_2$ | sub. 33 |
| 403 | sub. 19 | 4-FPh | CO | bond | 2 | O | $CH_2CH_2$ | sub. 33 |
| 404 | sub. 20 | 4-FPh | CO | bond | 2 | O | $CH_2CH_2$ | sub. 33 |
| 405 | sub. 21 | 4-FPh | CO | bond | 2 | O | $CH_2CH_2$ | sub. 33 |
| 406 | sub. 22 | 4-FPh | CO | bond | 2 | O | $CH_2CH_2$ | sub. 33 |
| 407 | sub. 23 | 4-FPh | CO | bond | 2 | O | $CH_2CH_2$ | sub. 33 |
| 408 | sub. 24 | 4-FPh | CO | bond | 2 | O | $CH_2CH_2$ | sub. 33 |
| 409 | sub. 25 | 4-FPh | CO | bond | 2 | O | $CH_2CH_2$ | sub. 33 |
| 410 | sub. 26 | 4-FPh | CO | bond | 2 | O | $CH_2CH_2$ | sub. 33 |
| 411 | sub. 27 | 4-FPh | CO | bond | 2 | O | $CH_2CH_2$ | sub. 33 |
| 412 | sub. 28 | 4-FPh | CO | bond | 2 | O | $CH_2CH_2$ | sub. 33 |
| 413 | sub. 29 | 4-FPh | CO | bond | 2 | O | $CH_2CH_2$ | sub. 33 |
| 414 | sub. 30 | 4-FPh | CO | bond | 2 | O | $CH_2CH_2$ | sub. 33 |
| 415 | sub. 31 | 4-FPh | CO | bond | 2 | O | $CH_2CH_2$ | sub. 33 |
| 416 | sub. 32 | 4-FPh | CO | bond | 2 | O | $CH_2CH_2$ | sub. 33 |
| 417 | sub. 1 | 4-FPh | CO | bond | 2 | O | $CH_2CH_2$ | sub. 34 |
| 418 | sub. 2 | 4-FPh | CO | bond | 2 | O | $CH_2CH_2$ | sub. 34 |
| 419 | sub. 3 | 4-FPh | CO | bond | 2 | O | $CH_2CH_2$ | sub. 34 |
| 420 | sub. 4 | 4-FPh | CO | bond | 2 | O | $CH_2CH_2$ | sub. 34 |
| 421 | sub. 5 | 4-FPh | CO | bond | 2 | O | $CH_2CH_2$ | sub. 34 |
| 422 | sub. 6 | 4-FPh | CO | bond | 2 | O | $CH_2CH_2$ | sub. 34 |
| 423 | sub. 7 | 4-FPh | CO | bond | 2 | O | $CH_2CH_2$ | sub. 34 |
| 424 | sub. 8 | 4-FPh | CO | bond | 2 | O | $CH_2CH_2$ | sub. 34 |
| 425 | sub. 9 | 4-FPh | CO | bond | 2 | O | $CH_2CH_2$ | sub. 34 |
| 426 | sub. 10 | 4-FPh | CO | bond | 2 | O | $CH_2CH_2$ | sub. 34 |
| 427 | sub. 11 | 4-FPh | CO | bond | 2 | O | $CH_2CH_2$ | sub. 34 |
| 428 | sub. 12 | 4-FPh | CO | bond | 2 | O | $CH_2CH_2$ | sub. 34 |
| 429 | sub. 13 | 4-FPh | CO | bond | 2 | O | $CH_2CH_2$ | sub. 34 |
| 430 | sub. 14 | 4-FPh | CO | bond | 2 | O | $CH_2CH_2$ | sub. 34 |
| 431 | sub. 15 | 4-FPh | CO | bond | 2 | O | $CH_2CH_2$ | sub. 34 |
| 432 | sub. 16 | 4-FPh | CO | bond | 2 | O | $CH_2CH_2$ | sub. 34 |
| 433 | sub. 17 | 4-FPh | CO | bond | 2 | O | $CH_2CH_2$ | sub. 34 |
| 434 | sub. 18 | 4-FPh | CO | bond | 2 | O | $CH_2CH_2$ | sub. 34 |
| 435 | sub. 19 | 4-FPh | CO | bond | 2 | O | $CH_2CH_2$ | sub. 34 |
| 436 | sub. 20 | 4-FPh | CO | bond | 2 | O | $CH_2CH_2$ | sub. 34 |
| 437 | sub. 21 | 4-FPh | CO | bond | 2 | O | $CH_2CH_2$ | sub. 34 |
| 438 | sub. 22 | 4-FPh | CO | bond | 2 | O | $CH_2CH_2$ | sub. 34 |
| 439 | sub. 23 | 4-FPh | CO | bond | 2 | O | $CH_2CH_2$ | sub. 34 |
| 440 | sub. 24 | 4-FPh | CO | bond | 2 | O | $CH_2CH_2$ | sub. 34 |
| 441 | sub. 25 | 4-FPh | CO | bond | 2 | O | $CH_2CH_2$ | sub. 34 |
| 442 | sub. 26 | 4-FPh | CO | bond | 2 | O | $CH_2CH_2$ | sub. 34 |
| 443 | sub. 27 | 4-FPh | CO | bond | 2 | O | $CH_2CH_2$ | sub. 34 |
| 444 | sub. 28 | 4-FPh | CO | bond | 2 | O | $CH_2CH_2$ | sub. 34 |
| 445 | sub. 29 | 4-FPh | CO | bond | 2 | O | $CH_2CH_2$ | sub. 34 |

TABLE 2-continued

| Cpd No. | $R^1$ | $R^2$ | A | B | n | D | E | Z |
|---|---|---|---|---|---|---|---|---|
| 446 | sub. 30 | 4-FPh | CO | bond | 2 | O | $CH_2CH_2$ | sub. 34 |
| 447 | sub. 31 | 4-FPh | CO | bond | 2 | O | $CH_2CH_2$ | sub. 34 |
| 448 | sub. 32 | 4-FPh | CO | bond | 2 | O | $CH_2CH_2$ | sub. 34 |
| 449 | sub. 1 | 4-FPh | CO | bond | 2 | O | $CH_2CH_2$ | sub. 35 |
| 450 | sub. 2 | 4-FPh | CO | bond | 2 | O | $CH_2CH_2$ | sub. 35 |
| 451 | sub. 3 | 4-FPh | CO | bond | 2 | O | $CH_2CH_2$ | sub. 35 |
| 452 | sub. 4 | 4-FPh | CO | bond | 2 | O | $CH_2CH_2$ | sub. 35 |
| 453 | sub. 5 | 4-FPh | CO | bond | 2 | O | $CH_2CH_2$ | sub. 35 |
| 454 | sub. 6 | 4-FPh | CO | bond | 2 | O | $CH_2CH_2$ | sub. 35 |
| 455 | sub. 7 | 4-FPh | CO | bond | 2 | O | $CH_2CH_2$ | sub. 35 |
| 456 | sub. 8 | 4-FPh | CO | bond | 2 | O | $CH_2CH_2$ | sub. 35 |
| 457 | sub. 9 | 4-FPh | CO | bond | 2 | O | $CH_2CH_2$ | sub. 35 |
| 458 | sub. 10 | 4-FPh | CO | bond | 2 | O | $CH_2CH_2$ | sub. 35 |
| 459 | sub. 11 | 4-FPh | CO | bond | 2 | O | $CH_2CH_2$ | sub. 35 |
| 460 | sub. 12 | 4-FPh | CO | bond | 2 | O | $CH_2CH_2$ | sub. 35 |
| 461 | sub. 13 | 4-FPh | CO | bond | 2 | O | $CH_2CH_2$ | sub. 35 |
| 462 | sub. 14 | 4-FPh | CO | bond | 2 | O | $CH_2CH_2$ | sub. 35 |
| 463 | sub. 15 | 4-FPh | CO | bond | 2 | O | $CH_2CH_2$ | sub. 35 |
| 464 | sub. 16 | 4-FPh | CO | bond | 2 | O | $CH_2CH_2$ | sub. 35 |
| 465 | sub. 17 | 4-FPh | CO | bond | 2 | O | $CH_2CH_2$ | sub. 35 |
| 466 | sub. 18 | 4-FPh | CO | bond | 2 | O | $CH_2CH_2$ | sub. 35 |
| 467 | sub. 19 | 4-FPh | CO | bond | 2 | O | $CH_2CH_2$ | sub. 35 |
| 468 | sub. 20 | 4-FPh | CO | bond | 2 | O | $CH_2CH_2$ | sub. 35 |
| 469 | sub. 21 | 4-FPh | CO | bond | 2 | O | $CH_2CH_2$ | sub. 35 |
| 470 | sub. 22 | 4-FPh | CO | bond | 2 | O | $CH_2CH_2$ | sub. 35 |
| 471 | sub. 23 | 4-FPh | CO | bond | 2 | O | $CH_2CH_2$ | sub. 35 |
| 472 | sub. 24 | 4-FPh | CO | bond | 2 | O | $CH_2CH_2$ | sub. 35 |
| 473 | sub. 25 | 4-FPh | CO | bond | 2 | O | $CH_2CH_2$ | sub. 35 |
| 474 | sub. 26 | 4-FPh | CO | bond | 2 | O | $CH_2CH_2$ | sub. 35 |
| 475 | sub. 27 | 4-FPh | CO | bond | 2 | O | $CH_2CH_2$ | sub. 35 |
| 476 | sub. 28 | 4-FPh | CO | bond | 2 | O | $CH_2CH_2$ | sub. 35 |
| 477 | sub. 29 | 4-FPh | CO | bond | 2 | O | $CH_2CH_2$ | sub. 35 |
| 478 | sub. 30 | 4-FPh | CO | bond | 2 | O | $CH_2CH_2$ | sub. 35 |
| 479 | sub. 31 | 4-FPh | CO | bond | 2 | O | $CH_2CH_2$ | sub. 35 |
| 480 | sub. 32 | 4-FPh | CO | bond | 2 | O | $CH_2CH_2$ | sub. 35 |
| 481 | sub. 1 | 3,4-diClPh | CO | bond | 1 | O | $(CH_2)_3$ | sub. 33 |
| 482 | sub. 2 | 3,4-diClPh | CO | bond | 1 | O | $(CH_2)_3$ | sub. 33 |
| 483 | sub. 3 | 3,4-diClPh | CO | bond | 1 | O | $(CH_2)_3$ | sub. 33 |
| 484 | sub. 4 | 3,4-diClPh | CO | bond | 1 | O | $(CH_2)_3$ | sub. 33 |
| 485 | sub. 5 | 3,4-diClPh | CO | bond | 1 | O | $(CH_2)_3$ | sub. 33 |
| 486 | sub. 6 | 3,4-diClPh | CO | bond | 1 | O | $(CH_2)_3$ | sub. 33 |
| 487 | sub. 7 | 3,4-diClPh | CO | bond | 1 | O | $(CH_2)_3$ | sub. 33 |
| 488 | sub. 8 | 3,4-diClPh | CO | bond | 1 | O | $(CH_2)_3$ | sub. 33 |
| 489 | sub. 9 | 3,4-diClPh | CO | bond | 1 | O | $(CH_2)_3$ | sub. 33 |
| 490 | sub. 10 | 3,4-diClPh | CO | bond | 1 | O | $(CH_2)_3$ | sub. 33 |
| 491 | sub. 11 | 3,4-diClPh | CO | bond | 1 | O | $(CH_2)_3$ | sub. 33 |
| 492 | sub. 12 | 3,4-diClPh | CO | bond | 1 | O | $(CH_2)_3$ | sub. 33 |
| 493 | sub. 13 | 3,4-diClPh | CO | bond | 1 | O | $(CH_2)_3$ | sub. 33 |
| 494 | sub. 14 | 3,4-diClPh | CO | bond | 1 | O | $(CH_2)_3$ | sub. 33 |
| 495 | sub. 15 | 3,4-diClPh | CO | bond | 1 | O | $(CH_2)_3$ | sub. 33 |
| 496 | sub. 16 | 3,4-diClPh | CO | bond | 1 | O | $(CH_2)_3$ | sub. 33 |
| 497 | sub. 17 | 3,4-diClPh | CO | bond | 1 | O | $(CH_2)_3$ | sub. 33 |
| 498 | sub. 18 | 3,4-diClPh | CO | bond | 1 | O | $(CH_2)_3$ | sub. 33 |
| 499 | sub. 19 | 3,4-diClPh | CO | bond | 1 | O | $(CH_2)_3$ | sub. 33 |
| 500 | sub. 20 | 3,4-diClPh | CO | bond | 1 | O | $(CH_2)_3$ | sub. 33 |
| 501 | sub. 21 | 3,4-diClPh | CO | bond | 1 | O | $(CH_2)_3$ | sub. 33 |
| 502 | sub. 22 | 3,4-diClPh | CO | bond | 1 | O | $(CH_2)_3$ | sub. 33 |
| 503 | sub. 23 | 3,4-diClPh | CO | bond | 1 | O | $(CH_2)_3$ | sub. 33 |
| 504 | sub. 24 | 3,4-diClPh | CO | bond | 1 | O | $(CH_2)_3$ | sub. 33 |
| 505 | sub. 25 | 3,4-diClPh | CO | bond | 1 | O | $(CH_2)_3$ | sub. 33 |
| 506 | sub. 26 | 3,4-diClPh | CO | bond | 1 | O | $(CH_2)_3$ | sub. 33 |
| 507 | sub. 27 | 3,4-diClPh | CO | bond | 1 | O | $(CH_2)_3$ | sub. 33 |
| 508 | sub. 28 | 3,4-diClPh | CO | bond | 1 | O | $(CH_2)_3$ | sub. 33 |
| 509 | sub. 29 | 3,4-diClPh | CO | bond | 1 | O | $(CH_2)_3$ | sub. 33 |
| 510 | sub. 30 | 3,4-diClPh | CO | bond | 1 | O | $(CH_2)_3$ | sub. 33 |
| 511 | sub. 31 | 3,4-diClPh | CO | bond | 1 | O | $(CH_2)_3$ | sub. 33 |
| 512 | sub. 32 | 3,4-diClPh | CO | bond | 1 | O | $(CH_2)_3$ | sub. 33 |
| 513 | sub. 1 | 3,4-diClPh | CO | bond | 1 | O | $(CH_2)_3$ | sub. 34 |
| 514 | sub. 2 | 3,4-diClPh | CO | bond | 1 | O | $(CH_2)_3$ | sub. 34 |
| 515 | sub. 3 | 3,4-diClPh | CO | bond | 1 | O | $(CH_2)_3$ | sub. 34 |
| 516 | sub. 4 | 3,4-diClPh | CO | bond | 1 | O | $(CH_2)_3$ | sub. 34 |
| 517 | sub. 5 | 3,4-diClPh | CO | bond | 1 | O | $(CH_2)_3$ | sub. 34 |
| 518 | sub. 6 | 3,4-diClPh | CO | bond | 1 | O | $(CH_2)_3$ | sub. 34 |
| 519 | sub. 7 | 3,4-diClPh | CO | bond | 1 | O | $(CH_2)_3$ | sub. 34 |
| 520 | sub. 8 | 3,4-diClPh | CO | bond | 1 | O | $(CH_2)_3$ | sub. 34 |
| 521 | sub. 9 | 3,4-diClPh | CO | bond | 1 | O | $(CH_2)_3$ | sub. 34 |
| 522 | sub. 10 | 3,4-diClPh | CO | bond | 1 | O | $(CH_2)_3$ | sub. 34 |
| 523 | sub. 11 | 3,4-diClPh | CO | bond | 1 | O | $(CH_2)_3$ | sub. 34 |
| 524 | sub. 12 | 3,4-diClPh | CO | bond | 1 | O | $(CH_2)_3$ | sub. 34 |
| 525 | sub. 13 | 3,4-diClPh | CO | bond | 1 | O | $(CH_2)_3$ | sub. 34 |
| 526 | sub. 14 | 3,4-diClPh | CO | bond | 1 | O | $(CH_2)_3$ | sub. 34 |
| 527 | sub. 15 | 3,4-diClPh | CO | bond | 1 | O | $(CH_2)_3$ | sub. 34 |
| 528 | sub. 16 | 3,4-diClPh | CO | bond | 1 | O | $(CH_2)_3$ | sub. 34 |
| 529 | sub. 17 | 3,4-diClPh | CO | bond | 1 | O | $(CH_2)_3$ | sub. 34 |
| 530 | sub. 18 | 3,4-diClPh | CO | bond | 1 | O | $(CH_2)_3$ | sub. 34 |
| 531 | sub. 19 | 3,4-diClPh | CO | bond | 1 | O | $(CH_2)_3$ | sub. 34 |
| 532 | sub. 20 | 3,4-diClPh | CO | bond | 1 | O | $(CH_2)_3$ | sub. 34 |
| 533 | sub. 21 | 3,4-diClPh | CO | bond | 1 | O | $(CH_2)_3$ | sub. 34 |
| 534 | sub. 22 | 3,4-diClPh | CO | bond | 1 | O | $(CH_2)_3$ | sub. 34 |
| 535 | sub. 23 | 3,4-diClPh | CO | bond | 1 | O | $(CH_2)_3$ | sub. 34 |
| 536 | sub. 24 | 3,4-diClPh | CO | bond | 1 | O | $(CH_2)_3$ | sub. 34 |
| 537 | sub. 25 | 3,4-diClPh | CO | bond | 1 | O | $(CH_2)_3$ | sub. 34 |
| 538 | sub. 26 | 3,4-diClPh | CO | bond | 1 | O | $(CH_2)_3$ | sub. 34 |
| 539 | sub. 27 | 3,4-diClPh | CO | bond | 1 | O | $(CH_2)_3$ | sub. 34 |
| 540 | sub. 28 | 3,4-diClPh | CO | bond | 1 | O | $(CH_2)_3$ | sub. 34 |
| 541 | sub. 29 | 3,4-diClPh | CO | bond | 1 | O | $(CH_2)_3$ | sub. 34 |
| 542 | sub. 30 | 3,4-diClPh | CO | bond | 1 | O | $(CH_2)_3$ | sub. 34 |
| 543 | sub. 31 | 3,4-diClPh | CO | bond | 1 | O | $(CH_2)_3$ | sub. 34 |
| 544 | sub. 32 | 3,4-diClPh | CO | bond | 1 | O | $(CH_2)_3$ | sub. 34 |
| 545 | sub. 1 | 3,4-diClPh | CO | bond | 1 | O | $(CH_2)_3$ | sub. 35 |
| 546 | sub. 2 | 3,4-diClPh | CO | bond | 1 | O | $(CH_2)_3$ | sub. 35 |
| 547 | sub. 3 | 3,4-diClPh | CO | bond | 1 | O | $(CH_2)_3$ | sub. 35 |
| 548 | sub. 4 | 3,4-diClPh | CO | bond | 1 | O | $(CH_2)_3$ | sub. 35 |
| 549 | sub. 5 | 3,4-diClPh | CO | bond | 1 | O | $(CH_2)_3$ | sub. 35 |
| 550 | sub. 6 | 3,4-diClPh | CO | bond | 1 | O | $(CH_2)_3$ | sub. 35 |
| 551 | sub. 7 | 3,4-diClPh | CO | bond | 1 | O | $(CH_2)_3$ | sub. 35 |
| 552 | sub. 8 | 3,4-diClPh | CO | bond | 1 | O | $(CH_2)_3$ | sub. 35 |
| 553 | sub. 9 | 3,4-diClPh | CO | bond | 1 | O | $(CH_2)_3$ | sub. 35 |
| 554 | sub. 10 | 3,4-diClPh | CO | bond | 1 | O | $(CH_2)_3$ | sub 35 |
| 555 | sub. 11 | 3,4-diClPh | CO | bond | 1 | O | $(CH_2)_3$ | sub 35 |
| 556 | sub. 12 | 3,4-diClPh | CO | bond | 1 | O | $(CH_2)_3$ | sub. 35 |
| 557 | sub. 13 | 3,4-diClPh | CO | bond | 1 | O | $(CH_2)_3$ | sub. 35 |
| 558 | sub. 14 | 3,4-diClPh | CO | bond | 1 | O | $(CH_2)_3$ | sub. 35 |
| 559 | sub. 15 | 3,4-diClPh | CO | bond | 1 | O | $(CH_2)_3$ | sub. 35 |
| 560 | sub. 16 | 3,4-diClPh | CO | bond | 1 | O | $(CH_2)_3$ | sub. 35 |
| 561 | sub. 17 | 3,4-diClPh | CO | bond | 1 | O | $(CH_2)_3$ | sub. 35 |
| 562 | sub. 18 | 3,4-diClPh | CO | bond | 1 | O | $(CH_2)_3$ | sub. 35 |
| 563 | sub. 19 | 3,4-diClPh | CO | bond | 1 | O | $(CH_2)_3$ | sub. 35 |
| 564 | sub. 20 | 3,4-diClPh | CO | bond | 1 | O | $(CH_2)_3$ | sub. 35 |
| 565 | sub. 21 | 3,4-diClPh | CO | bond | 1 | O | $(CH_2)_3$ | sub. 35 |
| 566 | sub. 22 | 3,4-diClPh | CO | bond | 1 | O | $(CH_2)_3$ | sub. 35 |
| 567 | sub. 23 | 3,4-diClPh | CO | bond | 1 | O | $(CH_2)_3$ | sub. 35 |
| 568 | sub. 24 | 3,4-diClPh | CO | bond | 1 | O | $(CH_2)_3$ | sub. 35 |
| 569 | sub. 25 | 3,4-diClPh | CO | bond | 1 | O | $(CH_2)_3$ | sub. 35 |
| 570 | sub. 26 | 3,4-diClPh | CO | bond | 1 | O | $(CH_2)_3$ | sub. 35 |
| 571 | sub. 27 | 3,4-diClPh | CO | bond | 1 | O | $(CH_2)_3$ | sub. 35 |
| 572 | sub. 28 | 3,4-diClPh | CO | bond | 1 | O | $(CH_2)_3$ | sub. 35 |
| 573 | sub. 29 | 3,4-diClPh | CO | bond | 1 | O | $(CH_2)_3$ | sub. 35 |
| 574 | sub. 30 | 3,4-diClPh | CO | bond | 1 | O | $(CH_2)_3$ | sub. 35 |
| 575 | sub. 31 | 3,4-diClPh | CO | bond | 1 | O | $(CH_2)_3$ | sub. 35 |
| 576 | sub. 32 | 3,4-diClPh | CO | bond | 1 | O | $(CH_2)_3$ | sub. 35 |
| 577 | sub. 1 | 3,4-diClPh | CO | bond | 2 | O | $(CH_2)_3$ | sub. 33 |
| 578 | sub. 2 | 3,4-diClPh | CO | bond | 2 | O | $(CH_2)_3$ | sub. 33 |
| 579 | sub. 3 | 3,4-diClPh | CO | bond | 2 | O | $(CH_2)_3$ | sub. 33 |
| 580 | sub. 4 | 3,4-diClPh | CO | bond | 2 | O | $(CH_2)_3$ | sub. 33 |
| 581 | sub. 5 | 3,4-diClPh | CO | bond | 2 | O | $(CH_2)_3$ | sub. 33 |
| 582 | sub. 6 | 3,4-diClPh | CO | bond | 2 | O | $(CH_2)_3$ | sub. 33 |
| 583 | sub. 7 | 3,4-diClPh | CO | bond | 2 | O | $(CH_2)_3$ | sub. 33 |
| 584 | sub. 8 | 3,4-diClPh | CO | bond | 2 | O | $(CH_2)_3$ | sub. 33 |
| 585 | sub. 9 | 3,4-diClPh | CO | bond | 2 | O | $(CH_2)_3$ | sub. 33 |
| 586 | sub. 10 | 3,4-diClPh | CO | bond | 2 | O | $(CH_2)_3$ | sub. 33 |
| 587 | sub. 11 | 3,4-diClPh | CO | bond | 2 | O | $(CH_2)_3$ | sub. 33 |
| 588 | sub. 12 | 3,4-diClPh | CO | bond | 2 | O | $(CH_2)_3$ | sub. 33 |
| 589 | sub. 13 | 3,4-diClPh | CO | bond | 2 | O | $(CH_2)_3$ | sub. 33 |
| 590 | sub. 14 | 3,4-diClPh | CO | bond | 2 | O | $(CH_2)_3$ | sub. 33 |
| 591 | sub. 15 | 3,4-diClPh | CO | bond | 2 | O | $(CH_2)_3$ | sub. 33 |
| 592 | sub. 16 | 3,4-diClPh | CO | bond | 2 | O | $(CH_2)_3$ | sub. 33 |
| 593 | sub. 17 | 3,4-diClPh | CO | bond | 2 | O | $(CH_2)_3$ | sub. 33 |
| 594 | sub. 18 | 3,4-diClPh | CO | bond | 2 | O | $(CH_2)_3$ | sub. 33 |
| 595 | sub. 19 | 3,4-diClPh | CO | bond | 2 | O | $(CH_2)_3$ | sub. 33 |
| 596 | sub. 20 | 3,4-diClPh | CO | bond | 2 | O | $(CH_2)_3$ | sub. 33 |
| 597 | sub. 21 | 3,4-diClPh | CO | bond | 2 | O | $(CH_2)_3$ | sub. 33 |

TABLE 2-continued

| Cpd No. | $R^1$ | $R^2$ | A | B | n | D | E | Z |
|---|---|---|---|---|---|---|---|---|
| 598 | sub. 22 | 3,4-diClPh | CO | bond | 2 | O | $(CH_2)_3$ | sub. 33 |
| 599 | sub. 23 | 3,4-diClPh | CO | bond | 2 | O | $(CH_2)_3$ | sub. 33 |
| 600 | sub. 24 | 3,4-diClPh | CO | bond | 2 | O | $(CH_2)_3$ | sub. 33 |
| 601 | sub. 25 | 3,4-diClPh | CO | bond | 2 | O | $(CH_2)_3$ | sub. 33 |
| 602 | sub. 26 | 3,4-diClPh | CO | bond | 2 | O | $(CH_2)_3$ | sub. 33 |
| 603 | sub. 27 | 3,4-diClPh | CO | bond | 2 | O | $(CH_2)_3$ | sub. 33 |
| 604 | sub. 28 | 3,4-diClPh | CO | bond | 2 | O | $(CH_2)_3$ | sub. 33 |
| 605 | sub. 29 | 3,4-diClPh | CO | bond | 2 | O | $(CH_2)_3$ | sub. 33 |
| 606 | sub. 30 | 3,4-diClPh | CO | bond | 2 | O | $(CH_2)_3$ | sub. 33 |
| 607 | sub. 31 | 3,4-diClPh | CO | bond | 2 | O | $(CH_2)_3$ | sub. 33 |
| 608 | sub. 32 | 3,4-diClPh | CO | bond | 2 | O | $(CH_2)_3$ | sub. 33 |
| 609 | sub. 1 | 3,4-diClPh | CO | bond | 2 | O | $(CH_2)_3$ | sub. 34 |
| 610 | sub. 2 | 3,4-diClPh | CO | bond | 2 | O | $(CH_2)_3$ | sub. 34 |
| 611 | sub. 3 | 3,4-diClPh | CO | bond | 2 | O | $(CH_2)_3$ | sub. 34 |
| 612 | sub. 4 | 3,4-diClPh | CO | bond | 2 | O | $(CH_2)_3$ | sub. 34 |
| 613 | sub. 5 | 3,4-diClPh | CO | bond | 2 | O | $(CH_2)_3$ | sub. 34 |
| 614 | sub. 6 | 3,4-diClPh | CO | bond | 2 | O | $(CH_2)_3$ | sub. 34 |
| 615 | sub. 7 | 3,4-diClPh | CO | bond | 2 | O | $(CH_2)_3$ | sub. 34 |
| 616 | sub. 8 | 3,4-diClPh | CO | bond | 2 | O | $(CH_2)_3$ | sub. 34 |
| 617 | sub. 9 | 3,4-diClPh | CO | bond | 2 | O | $(CH_2)_3$ | sub. 34 |
| 618 | sub. 10 | 3,4-diClPh | CO | bond | 2 | O | $(CH_2)_3$ | sub. 34 |
| 619 | sub. 11 | 3,4-diClPh | CO | bond | 2 | O | $(CH_2)_3$ | sub. 34 |
| 620 | sub. 12 | 3,4-diClPh | CO | bond | 2 | O | $(CH_2)_3$ | sub. 34 |
| 621 | sub. 13 | 3,4-diClPh | CO | bond | 2 | O | $(CH_2)_3$ | sub. 34 |
| 622 | sub. 14 | 3,4-diClPh | CO | bond | 2 | O | $(CH_2)_3$ | sub. 34 |
| 623 | sub. 15 | 3,4-diClPh | CO | bond | 2 | O | $(CH_2)_3$ | sub. 34 |
| 624 | sub. 16 | 3,4-diClPh | CO | bond | 2 | O | $(CH_2)_3$ | sub. 34 |
| 625 | sub. 17 | 3,4-diClPh | CO | bond | 2 | O | $(CH_2)_3$ | sub. 34 |
| 626 | sub. 18 | 3,4-diClPh | CO | bond | 2 | O | $(CH_2)_3$ | sub. 34 |
| 627 | sub. 19 | 3,4-diClPh | CO | bond | 2 | O | $(CH_2)_3$ | sub. 34 |
| 628 | sub. 20 | 3,4-diClPh | CO | bond | 2 | O | $(CH_2)_3$ | sub. 34 |
| 629 | sub. 21 | 3,4-diClPh | CO | bond | 2 | O | $(CH_2)_3$ | sub. 34 |
| 630 | sub. 22 | 3,4-diClPh | CO | bond | 2 | O | $(CH_2)_3$ | sub. 34 |
| 631 | sub. 23 | 3,4-diClPh | CO | bond | 2 | O | $(CH_2)_3$ | sub. 34 |
| 632 | sub. 24 | 3,4-diClPh | CO | bond | 2 | O | $(CH_2)_3$ | sub. 34 |
| 633 | sub. 25 | 3,4-diClPh | CO | bond | 2 | O | $(CH_2)_3$ | sub. 34 |
| 634 | sub. 26 | 3,4-diClPh | CO | bond | 2 | O | $(CH_2)_3$ | sub. 34 |
| 635 | sub. 27 | 3,4-diClPh | CO | bond | 2 | O | $(CH_2)_3$ | sub. 34 |
| 636 | sub. 28 | 3,4-diClPh | CO | bond | 2 | O | $(CH_2)_3$ | sub. 34 |
| 637 | sub. 29 | 3,4-diClPh | CO | bond | 2 | O | $(CH_2)_3$ | sub. 34 |
| 638 | sub. 30 | 3,4-diClPh | CO | bond | 2 | O | $(CH_2)_3$ | sub. 34 |
| 639 | sub. 31 | 3,4-diClPh | CO | bond | 2 | O | $(CH_2)_3$ | sub. 34 |
| 640 | sub. 32 | 3,4-diClPh | CO | bond | 2 | O | $(CH_2)_3$ | sub. 34 |
| 641 | sub. 1 | 3,4-diClPh | CO | bond | 2 | O | $(CH_2)_3$ | sub. 35 |
| 642 | sub. 2 | 3,4-diClPh | CO | bond | 2 | O | $(CH_2)_3$ | sub. 35 |
| 643 | sub. 3 | 3,4-diClPh | CO | bond | 2 | O | $(CH_2)_3$ | sub. 35 |
| 644 | sub. 4 | 3,4-diClPh | CO | bond | 2 | O | $(CH_2)_3$ | sub. 35 |
| 645 | sub. 5 | 3,4-diClPh | CO | bond | 2 | O | $(CH_2)_3$ | sub. 35 |
| 646 | sub. 6 | 3,4-diClPh | CO | bond | 2 | O | $(CH_2)_3$ | sub. 35 |
| 647 | sub. 7 | 3,4-diClPh | CO | bond | 2 | O | $(CH_2)_3$ | sub. 35 |
| 648 | sub. 8 | 3,4-diClPh | CO | bond | 2 | O | $(CH_2)_3$ | sub. 35 |
| 649 | sub. 9 | 3,4-diClPh | CO | bond | 2 | O | $(CH_2)_3$ | sub. 35 |
| 650 | sub. 10 | 3,4-diClPh | CO | bond | 2 | O | $(CH_2)_3$ | sub. 35 |
| 651 | sub. 11 | 3,4-diClPh | CO | bond | 2 | O | $(CH_2)_3$ | sub. 35 |
| 652 | sub. 12 | 3,4-diClPh | CO | bond | 2 | O | $(CH_2)_3$ | sub. 35 |
| 653 | sub. 13 | 3,4-diClPh | CO | bond | 2 | O | $(CH_2)_3$ | sub. 35 |
| 654 | sub. 14 | 3,4-diClPh | CO | bond | 2 | O | $(CH_2)_3$ | sub. 35 |
| 655 | sub. 15 | 3,4-diClPh | CO | bond | 2 | O | $(CH_2)_3$ | sub. 35 |
| 656 | sub. 16 | 3,4-diClPh | CO | bond | 2 | O | $(CH_2)_3$ | sub. 35 |
| 657 | sub. 17 | 3,4-diClPh | CO | bond | 2 | O | $(CH_2)_3$ | sub. 35 |
| 658 | sub. 18 | 3,4-diClPh | CO | bond | 2 | O | $(CH_2)_3$ | sub. 35 |
| 659 | sub. 19 | 3,4-diClPh | CO | bond | 2 | O | $(CH_2)_3$ | sub. 35 |
| 660 | sub. 20 | 3,4-diClPh | CO | bond | 2 | O | $(CH_2)_3$ | sub. 35 |
| 661 | sub. 21 | 3,4-diClPh | CO | bond | 2 | O | $(CH_2)_3$ | sub. 35 |
| 662 | sub. 22 | 3,4-diClPh | CO | bond | 2 | O | $(CH_2)_3$ | sub. 35 |
| 663 | sub. 23 | 3,4-diClPh | CO | bond | 2 | O | $(CH_2)_3$ | sub. 35 |
| 664 | sub. 24 | 3,4-diClPh | CO | bond | 2 | O | $(CH_2)_3$ | sub. 35 |
| 665 | sub. 25 | 3,4-diClPh | CO | bond | 2 | O | $(CH_2)_3$ | sub. 35 |
| 666 | sub. 26 | 3,4-diClPh | CO | bond | 2 | O | $(CH_2)_3$ | sub. 35 |
| 667 | sub. 27 | 3,4-diClPh | CO | bond | 2 | O | $(CH_2)_3$ | sub. 35 |
| 668 | sub. 28 | 3,4-diClPh | CO | bond | 2 | O | $(CH_2)_3$ | sub. 35 |
| 669 | sub. 29 | 3,4-diClPh | CO | bond | 2 | O | $(CH_2)_3$ | sub. 35 |
| 670 | sub. 30 | 3,4-diClPh | CO | bond | 2 | O | $(CH_2)_3$ | sub. 35 |
| 671 | sub. 31 | 3,4-diClPh | CO | bond | 2 | O | $(CH_2)_3$ | sub. 35 |
| 672 | sub. 32 | 3,4-diClPh | CO | bond | 2 | O | $(CH_2)_3$ | sub. 35 |
| 673 | sub. 1 | 3,4-diFPh | CO | bond | 2 | O | $(CH_2)_3$ | sub. 33 |

TABLE 2-continued

| Cpd No. | $R^1$ | $R^2$ | A | B | n | D | E | Z |
|---|---|---|---|---|---|---|---|---|
| 674 | sub. 2 | 3,4-diFPh | CO | bond | 2 | O | $(CH_2)_3$ | sub. 33 |
| 675 | sub. 3 | 3,4-diFPh | CO | bond | 2 | O | $(CH_2)_3$ | sub. 33 |
| 676 | sub. 4 | 3,4-diFPh | CO | bond | 2 | O | $(CH_2)_3$ | sub. 33 |
| 677 | sub. 5 | 3,4-diFPh | CO | bond | 2 | O | $(CH_2)_3$ | sub. 33 |
| 678 | sub. 6 | 3,4-diFPh | CO | bond | 2 | O | $(CH_2)_3$ | sub. 33 |
| 679 | sub. 7 | 3,4-diFPh | CO | bond | 2 | O | $(CH_2)_3$ | sub. 33 |
| 680 | sub. 8 | 3,4-diFPh | CO | bond | 2 | O | $(CH_2)_3$ | sub. 33 |
| 681 | sub. 9 | 3,4-diFPh | CO | bond | 2 | O | $(CH_2)_3$ | sub. 33 |
| 682 | sub. 10 | 3,4-diFPh | CO | bond | 2 | O | $(CH_2)_3$ | sub. 33 |
| 683 | sub. 11 | 3,4-diFPh | CO | bond | 2 | O | $(CH_2)_3$ | sub. 33 |
| 684 | sub. 12 | 3,4-diFPh | CO | bond | 2 | O | $(CH_2)_3$ | sub. 33 |
| 685 | sub. 13 | 3,4-diFPh | CO | bond | 2 | O | $(CH_2)_3$ | sub. 33 |
| 686 | sub. 14 | 3,4-diFPh | CO | bond | 2 | O | $(CH_2)_3$ | sub. 33 |
| 687 | sub. 15 | 3,4-diFPh | CO | bond | 2 | O | $(CH_2)_3$ | sub. 33 |
| 688 | sub. 16 | 3,4-diFPh | CO | bond | 2 | O | $(CH_2)_3$ | sub. 33 |
| 689 | sub. 17 | 3,4-diFPh | CO | bond | 2 | O | $(CH_2)_3$ | sub. 33 |
| 690 | sub. 18 | 3,4-diFPh | CO | bond | 2 | O | $(CH_2)_3$ | sub. 33 |
| 691 | sub. 19 | 3,4-diFPh | CO | bond | 2 | O | $(CH_2)_3$ | sub. 33 |
| 692 | sub. 20 | 3,4-diFPh | CO | bond | 2 | O | $(CH_2)_3$ | sub. 33 |
| 693 | sub. 21 | 3,4-diFPh | CO | bond | 2 | O | $(CH_2)_3$ | sub. 33 |
| 694 | sub. 22 | 3,4-diFPh | CO | bond | 2 | O | $(CH_2)_3$ | sub. 33 |
| 695 | sub. 23 | 3,4-diFPh | CO | bond | 2 | O | $(CH_2)_3$ | sub. 33 |
| 696 | sub. 24 | 3,4-diFPh | CO | bond | 2 | O | $(CH_2)_3$ | sub. 33 |
| 697 | sub. 25 | 3,4-diFPh | CO | bond | 2 | O | $(CH_2)_3$ | sub. 33 |
| 698 | sub. 26 | 3,4-diFPh | CO | bond | 2 | O | $(CH_2)_3$ | sub. 33 |
| 699 | sub. 27 | 3,4-diFPh | CO | bond | 2 | O | $(CH_2)_3$ | sub. 33 |
| 700 | sub. 28 | 3,4-diFPh | CO | bond | 2 | O | $(CH_2)_3$ | sub. 33 |
| 701 | sub. 29 | 3,4-diFPh | CO | bond | 2 | O | $(CH_2)_3$ | sub. 33 |
| 702 | sub. 30 | 3,4-diFPh | CO | bond | 2 | O | $(CH_2)_3$ | sub. 33 |
| 703 | sub. 31 | 3,4-diFPh | CO | bond | 2 | O | $(CH_2)_3$ | sub. 33 |
| 704 | sub. 32 | 3,4-diFPh | CO | bond | 2 | O | $(CH_2)_3$ | sub. 33 |
| 705 | sub. 1 | 3,4-diFPh | CO | bond | 2 | O | $(CH_2)_3$ | sub. 34 |
| 706 | sub. 2 | 3,4-diFPh | CO | bond | 2 | O | $(CH_2)_3$ | sub. 34 |
| 707 | sub. 3 | 3,4-diFPh | CO | bond | 2 | O | $(CH_2)_3$ | sub. 34 |
| 708 | sub. 4 | 3,4-diFPh | CO | bond | 2 | O | $(CH_2)_3$ | sub. 34 |
| 709 | sub. 5 | 3,4-diFPh | CO | bond | 2 | O | $(CH_2)_3$ | sub. 34 |
| 710 | sub. 6 | 3,4-diFPh | CO | bond | 2 | O | $(CH_2)_3$ | sub. 34 |
| 711 | sub. 7 | 3,4-diFPh | CO | bond | 2 | O | $(CH_2)_3$ | sub. 34 |
| 712 | sub. 8 | 3,4-diFPh | CO | bond | 2 | O | $(CH_2)_3$ | sub. 34 |
| 713 | sub. 9 | 3,4-diFPh | CO | bond | 2 | O | $(CH_2)_3$ | sub. 34 |
| 714 | sub. 10 | 3,4-diFPh | CO | bond | 2 | O | $(CH_2)_3$ | sub. 34 |
| 715 | sub. 11 | 3,4-diFPh | CO | bond | 2 | O | $(CH_2)_3$ | sub. 34 |
| 716 | sub. 12 | 3,4-diFPh | CO | bond | 2 | O | $(CH_2)_3$ | sub. 34 |
| 717 | sub. 13 | 3,4-diFPh | CO | bond | 2 | O | $(CH_2)_3$ | sub. 34 |
| 718 | sub. 14 | 3,4-diFPh | CO | bond | 2 | O | $(CH_2)_3$ | sub. 34 |
| 719 | sub. 15 | 3,4-diFPh | CO | bond | 2 | O | $(CH_2)_3$ | sub. 34 |
| 720 | sub. 16 | 3,4-diFPh | CO | bond | 2 | O | $(CH_2)_3$ | sub. 34 |
| 721 | sub. 17 | 3,4-diFPh | CO | bond | 2 | O | $(CH_2)_3$ | sub. 34 |
| 722 | sub. 18 | 3,4-diFPh | CO | bond | 2 | O | $(CH_2)_3$ | sub. 34 |
| 723 | sub. 19 | 3,4-diFPh | CO | bon& | 2 | O | $(CH_2)_3$ | sub. 34 |
| 724 | sub. 20 | 3,4-diFPh | CO | bond | 2 | O | $(CH_2)_3$ | sub. 34 |
| 725 | sub. 21 | 3,4-diFPh | CO | bond | 2 | O | $(CH_2)_3$ | sub. 34 |
| 726 | sub. 22 | 3,4-diFPh | CO | bond | 2 | O | $(CH_2)_3$ | sub. 34 |
| 727 | sub. 23 | 3,4-diFPh | CO | bond | 2 | O | $(CH_2)_3$ | sub. 34 |
| 728 | sub. 24 | 3,4-diFPh | CO | bond | 2 | O | $(CH_2)_3$ | sub. 34 |
| 729 | sub. 25 | 3,4-diFPh | CO | bond | 2 | O | $(CH_2)_3$ | sub. 34 |
| 730 | sub. 26 | 3,4-diFPh | CO | bond | 2 | O | $(CH_2)_3$ | sub. 34 |
| 731 | sub. 27 | 3,4-diFPh | CO | bond | 2 | O | $(CH_2)_3$ | sub. 34 |
| 732 | sub. 28 | 3,4-diFPh | CO | bond | 2 | O | $(CH_2)_3$ | sub. 34 |
| 733 | sub. 29 | 3,4-diFPh | CO | bond | 2 | O | $(CH_2)_3$ | sub. 34 |
| 734 | sub. 30 | 3,4-diFPh | CO | bond | 2 | O | $(CH_2)_3$ | sub. 34 |
| 735 | sub. 31 | 3,4-diFPh | CO | bond | 2 | O | $(CH_2)_3$ | sub. 34 |
| 736 | sub. 32 | 3,4-diFPh | CO | bond | 2 | O | $(CH_2)_3$ | sub. 34 |
| 737 | sub. 1 | 3,4-diFPh | CO | bond | 2 | O | $(CH_2)_3$ | sub. 35 |
| 738 | sub. 2 | 3,4-diFPh | CO | bond | 2 | O | $(CH_2)_3$ | sub. 35 |
| 739 | sub. 3 | 3,4-diFPh | CO | bond | 2 | O | $(CH_2)_3$ | sub. 35 |
| 740 | sub. 4 | 3,4-diFPh | CO | bond | 2 | O | $(CH_2)_3$ | sub. 35 |
| 741 | sub. 5 | 3,4-diFPh | CO | bond | 2 | O | $(CH_2)_3$ | sub. 35 |
| 742 | sub. 6 | 3,4-diFPh | CO | bond | 2 | O | $(CH_2)_3$ | sub. 35 |
| 743 | sub. 7 | 3,4-diFPh | CO | bond | 2 | O | $(CH_2)_3$ | sub. 35 |
| 744 | sub. 8 | 3,4-diFPh | CO | bond | 2 | O | $(CH_2)_3$ | sub. 35 |
| 745 | sub. 9 | 3,4-diFPh | CO | bond | 2 | O | $(CH_2)_3$ | sub. 35 |
| 746 | sub. 10 | 3,4-diFPh | CO | bond | 2 | O | $(CH_2)_3$ | sub. 35 |
| 747 | sub. 11 | 3,4-diFPh | CO | bond | 2 | O | $(CH_2)_3$ | sub. 35 |
| 748 | sub. 12 | 3,4-diFPh | CO | bond | 2 | O | $(CH_2)_3$ | sub. 35 |
| 749 | sub. 13 | 3,4-diFPh | CO | bond | 2 | O | $(CH_2)_3$ | sub. 35 |

TABLE 2-continued

| Cpd No. | $R^1$ | $R^2$ | A | B | n | D | E | Z |
|---|---|---|---|---|---|---|---|---|
| 750 | sub. 14 | 3,4-diFPh | CO | bond | 2 | O | $(CH_2)_3$ | sub. 35 |
| 751 | sub. 15 | 3,4-diFPh | CO | bond | 2 | O | $(CH_2)_3$ | sub. 35 |
| 752 | sub. 16 | 3,4-diFPh | CO | bond | 2 | O | $(CH_2)_3$ | sub. 35 |
| 753 | sub. 17 | 3,4-diFPh | CO | bond | 2 | O | $(CH_2)_3$ | sub. 35 |
| 754 | sub. 18 | 3,4-diFPh | CO | bond | 2 | O | $(CH_2)_3$ | sub. 35 |
| 755 | sub. 19 | 3,4-diFPh | CO | bond | 2 | O | $(CH_2)_3$ | sub. 35 |
| 756 | sub. 20 | 3,4-diFPh | CO | bond | 2 | O | $(CH_2)_3$ | sub. 35 |
| 757 | sub. 21 | 3,4-diFPh | CO | bond | 2 | O | $(CH_2)_3$ | sub. 35 |
| 758 | sub. 22 | 3,4-diFPh | CO | bond | 2 | O | $(CH_2)_3$ | sub. 35 |
| 759 | sub. 23 | 3,4-diFPh | CO | bond | 2 | O | $(CH_2)_3$ | sub. 35 |
| 760 | sub. 24 | 3,4-diFPh | CO | bond | 2 | O | $(CH_2)_3$ | sub. 35 |
| 761 | sub. 25 | 3,4-diFPh | CO | bond | 2 | O | $(CH_2)_3$ | sub. 35 |
| 762 | sub. 26 | 3,4-diFPh | CO | bond | 2 | O | $(CH_2)_3$ | sub. 35 |
| 763 | sub. 27 | 3,4-diFPh | CO | bond | 2 | O | $(CH_2)_3$ | sub. 35 |
| 764 | sub. 28 | 3,4-diFPh | CO | bond | 2 | O | $(CH_2)_3$ | sub. 35 |
| 765 | sub. 29 | 3,4-diFPh | CO | bond | 2 | O | $(CH_2)_3$ | sub. 35 |
| 766 | sub. 30 | 3,4-diFPh | CO | bond | 2 | O | $(CH_2)_3$ | sub. 35 |
| 767 | sub. 31 | 3,4-diFPh | CO | bond | 2 | O | $(CH_2)_3$ | sub. 35 |
| 768 | sub. 32 | 3,4-diFPh | CO | bond | 2 | O | $(CH_2)_3$ | sub. 35 |

TABLE 3

| Cpd No. | $R^1$ | $R^2$ | A | B | n | D | E | Z |
|---|---|---|---|---|---|---|---|---|
| 769 | sub. 1 | 4-ClPh | CO | bond | 2 | O | $(CH_2)_3$ | sub. 33 |
| 770 | sub. 2 | 4-ClPh | CO | bond | 2 | O | $(CH_2)_3$ | sub. 33 |
| 771 | sub. 3 | 4-ClPh | CO | bond | 2 | O | $(CH_2)_3$ | sub. 33 |
| 772 | sub. 4 | 4-ClPh | CO | bond | 2 | O | $(CH_2)_3$ | sub. 33 |
| 773 | sub. 5 | 4-ClPh | CO | bond | 2 | O | $(CH_2)_3$ | sub. 33 |
| 774 | sub. 6 | 4-ClPh | CO | bond | 2 | O | $(CH_2)_3$ | sub. 33 |
| 775 | sub. 7 | 4-ClPh | CO | bond | 2 | O | $(CH_2)_3$ | sub. 33 |
| 776 | sub. 8 | 4-ClPh | CO | bond | 2 | O | $(CH_2)_3$ | sub. 33 |
| 777 | sub. 9 | 4-ClPh | CO | bond | 2 | O | $(CH_2)_3$ | sub. 33 |
| 778 | sub. 10 | 4-ClPh | CO | bond | 2 | O | $(CH_2)_3$ | sub. 33 |
| 779 | sub. 11 | 4-ClPh | CO | bond | 2 | O | $(CH_2)_3$ | sub. 33 |
| 780 | sub. 12 | 4-ClPh | CO | bond | 2 | O | $(CH_2)_3$ | sub. 33 |
| 781 | sub. 13 | 4-ClPh | CO | bond | 2 | O | $(CH_2)_3$ | sub. 33 |
| 782 | sub. 14 | 4-ClPh | CO | bond | 2 | O | $(CH_2)_3$ | sub. 33 |
| 783 | sub. 15 | 4-ClPh | CO | bond | 2 | O | $(CH_2)_3$ | sub. 33 |
| 784 | sub. 16 | 4-ClPh | CO | bond | 2 | O | $(CH_2)_3$ | sub. 33 |
| 785 | sub. 17 | 4-ClPh | CO | bond | 2 | O | $(CH_2)_3$ | sub. 33 |
| 786 | sub. 18 | 4-ClPh | CO | bond | 2 | O | $(CH_2)_3$ | sub. 33 |
| 787 | sub. 19 | 4-ClPh | CO | bond | 2 | O | $(CH_2)_3$ | sub. 33 |
| 788 | sub. 20 | 4-ClPh | CO | bond | 2 | O | $(CH_2)_3$ | sub. 33 |
| 789 | sub. 21 | 4-ClPh | CO | bond | 2 | O | $(CH_2)_3$ | sub. 33 |
| 790 | sub. 22 | 4-ClPh | CO | bond | 2 | O | $(CH_2)_3$ | sub. 33 |
| 791 | sub. 23 | 4-ClPh | CO | bond | 2 | O | $(CH_2)_3$ | sub. 33 |
| 792 | sub. 24 | 4-ClPh | CO | bond | 2 | O | $(CH_2)_3$ | sub. 33 |
| 793 | sub. 25 | 4-ClPh | CO | bond | 2 | O | $(CH_2)_3$ | sub. 33 |
| 794 | sub. 26 | 4-ClPh | CO | bond | 2 | O | $(CH_2)_3$ | sub. 33 |
| 795 | sub. 27 | 4-ClPh | CO | bond | 2 | O | $(CH_2)_3$ | sub. 33 |
| 796 | sub. 28 | 4-ClPh | CO | bond | 2 | O | $(CH_2)_3$ | sub. 33 |
| 797 | sub. 29 | 4-ClPh | CO | bond | 2 | O | $(CH_2)_3$ | sub. 33 |
| 798 | sub. 30 | 4-ClPh | CO | bond | 2 | O | $(CH_2)_3$ | sub. 33 |
| 799 | sub. 31 | 4-ClPh | CO | bond | 2 | O | $(CH_2)_3$ | sub. 33 |
| 800 | sub. 32 | 4-ClPh | CO | bond | 2 | O | $(CH_2)_3$ | sub. 33 |
| 801 | sub. 1 | 4-ClPh | CO | bond | 2 | O | $(CH_2)_3$ | sub. 34 |
| 802 | sub. 2 | 4-ClPh | CO | bond | 2 | O | $(CH_2)_3$ | sub. 34 |
| 803 | sub. 3 | 4-ClPh | CO | bond | 2 | O | $(CH_2)_3$ | sub. 34 |
| 804 | sub. 4 | 4-ClPh | CO | bond | 2 | O | $(CH_2)_3$ | sub. 34 |
| 805 | sub. 5 | 4-ClPh | CO | bond | 2 | O | $(CH_2)_3$ | sub. 34 |
| 806 | sub. 6 | 4-ClPh | CO | bond | 2 | O | $(CH_2)_3$ | sub. 34 |
| 807 | sub. 7 | 4-ClPh | CO | bond | 2 | O | $(CH_2)_3$ | sub. 34 |
| 808 | sub. 8 | 4-ClPh | CO | bond | 2 | O | $(CH_2)_3$ | sub. 34 |
| 809 | sub. 9 | 4-ClPh | CO | bond | 2 | O | $(CH_2)_3$ | sub. 34 |
| 810 | sub. 10 | 4-ClPh | CO | bond | 2 | O | $(CH_2)_3$ | sub. 34 |
| 811 | sub. 11 | 4-ClPh | CO | bond | 2 | O | $(CH_2)_3$ | sub. 34 |
| 812 | sub. 12 | 4-ClPh | CO | bond | 2 | O | $(CH_2)_3$ | sub. 34 |
| 813 | sub. 13 | 4-ClPh | CO | bond | 2 | O | $(CH_2)_3$ | sub. 34 |
| 814 | sub. 14 | 4-ClPh | CO | bond | 2 | O | $(CH_2)_3$ | sub. 34 |
| 815 | sub. 15 | 4-ClPh | CO | bond | 2 | O | $(CH_2)_3$ | sub. 34 |
| 816 | sub. 16 | 4-ClPh | CO | bond | 2 | O | $(CH_2)_3$ | sub. 34 |

TABLE 3-continued

| Cpd No. | $R^1$ | $R^2$ | A | B | n | D | E | Z |
|---|---|---|---|---|---|---|---|---|
| 817 | sub. 17 | 4-ClPh | CO | bond | 2 | O | $(CH_2)_3$ | sub. 34 |
| 818 | sub. 18 | 4-ClPh | CO | bond | 2 | O | $(CH_2)_3$ | sub. 34 |
| 819 | sub. 19 | 4-ClPh | CO | bond | 2 | O | $(CH_2)_3$ | sub. 34 |
| 820 | sub. 20 | 4-ClPh | CO | bond | 2 | O | $(CH_2)_3$ | sub. 34 |
| 821 | sub. 21 | 4-ClPh | CO | bond | 2 | O | $(CH_2)_3$ | sub. 34 |
| 822 | sub. 22 | 4-ClPh | CO | bond | 2 | O | $(CH_2)_3$ | sub. 34 |
| 823 | sub. 23 | 4-ClPh | CO | bond | 2 | O | $(CH_2)_3$ | sub. 34 |
| 824 | sub. 24 | 4-ClPh | CO | bond | 2 | O | $(CH_2)_3$ | sub. 34 |
| 825 | sub. 25 | 4-ClPh | CO | bond | 2 | O | $(CH_2)_3$ | sub. 34 |
| 826 | sub. 26 | 4-ClPh | CO | bond | 2 | O | $(CH_2)_3$ | sub. 34 |
| 827 | sub. 27 | 4-ClPh | CO | bond | 2 | O | $(CH_2)_3$ | sub. 34 |
| 828 | sub. 28 | 4-ClPh | CO | bond | 2 | O | $(CH_2)_3$ | sub. 34 |
| 829 | sub. 29 | 4-ClPh | CO | bond | 2 | O | $(CH_2)_3$ | sub. 34 |
| 830 | sub. 30 | 4-ClPh | CO | bond | 2 | O | $(CH_2)_3$ | sub. 34 |
| 831 | sub. 31 | 4-ClPh | CO | bond | 2 | O | $(CH_2)_3$ | sub. 34 |
| 832 | sub. 32 | 4-ClPh | CO | bond | 2 | O | $(CH_2)_3$ | sub. 34 |
| 833 | sub. 1 | 4-ClPh | CO | bond | 2 | O | $(CH_2)_3$ | sub. 35 |
| 834 | sub. 2 | 4-ClPh | CO | bond | 2 | O | $(CH_2)_3$ | sub. 35 |
| 835 | sub. 3 | 4-ClPh | CO | bond | 2 | O | $(CH_2)_3$ | sub. 35 |
| 836 | sub. 4 | 4-ClPh | CO | bond | 2 | O | $(CH_2)_3$ | sub. 35 |
| 837 | sub. 5 | 4-ClPh | CO | bond | 2 | O | $(CH_2)_3$ | sub. 35 |
| 838 | sub. 6 | 4-ClPh | CO | bond | 2 | O | $(CH_2)_3$ | sub. 35 |
| 839 | sub. 7 | 4-ClPh | CO | bond | 2 | O | $(CH_2)_3$ | sub. 35 |
| 840 | sub. 8 | 4-ClPh | CO | bond | 2 | O | $(CH_2)_3$ | sub. 35 |
| 841 | sub. 9 | 4-ClPh | CO | bond | 2 | O | $(CH_2)_3$ | sub. 35 |
| 842 | sub. 10 | 4-ClPh | CO | bond | 2 | O | $(CH_2)_3$ | sub. 35 |
| 843 | sub. 11 | 4-ClPh | CO | bond | 2 | O | $(CH_2)_3$ | sub. 35 |
| 844 | sub. 12 | 4-ClPh | CO | bond | 2 | O | $(CH_2)_3$ | sub. 35 |
| 845 | sub. 13 | 4-ClPh | CO | bond | 2 | O | $(CH_2)_3$ | sub. 35 |
| 846 | sub. 14 | 4-ClPh | CO | bond | 2 | O | $(CH_2)_3$ | sub. 35 |
| 847 | sub. 15 | 4-ClPh | CO | bond | 2 | O | $(CH_2)_3$ | sub. 35 |
| 848 | sub. 16 | 4-ClPh | CO | bond | 2 | O | $(CH_2)_3$ | sub. 35 |
| 849 | sub. 17 | 4-ClPh | CO | bond | 2 | O | $(CH_2)_3$ | sub. 35 |
| 850 | sub. 18 | 4-ClPh | CO | bond | 2 | O | $(CH_2)_3$ | sub. 35 |
| 851 | sub. 19 | 4-ClPh | CO | bond | 2 | O | $(CH_2)_3$ | sub. 35 |
| 852 | sub. 20 | 4-ClPh | CO | bond | 2 | O | $(CH_2)_3$ | sub. 35 |
| 853 | sub. 21 | 4-ClPh | CO | bond | 2 | O | $(CH_2)_3$ | sub. 35 |
| 854 | sub. 22 | 4-ClPh | CO | bond | 2 | O | $(CH_2)_3$ | sub. 35 |
| 855 | sub. 23 | 4-ClPh | CO | bond | 2 | O | $(CH_2)_3$ | sub. 35 |
| 856 | sub. 24 | 4-ClPh | CO | bond | 2 | O | $(CH_2)_3$ | sub. 35 |
| 857 | sub. 25 | 4-ClPh | CO | bond | 2 | O | $(CH_2)_3$ | sub. 35 |
| 858 | sub. 26 | 4-ClPh | CO | bond | 2 | O | $(CH_2)_3$ | sub. 35 |
| 859 | sub. 27 | 4-ClPh | CO | bond | 2 | O | $(CH_2)_3$ | sub. 35 |
| 860 | sub. 28 | 4-ClPh | CO | bond | 2 | O | $(CH_2)_3$ | sub. 35 |
| 861 | sub. 29 | 4-ClPh | CO | bond | 2 | O | $(CH_2)_3$ | sub. 35 |
| 862 | sub. 30 | 4-ClPh | CO | bond | 2 | O | $(CH_2)_3$ | sub. 35 |
| 863 | sub. 31 | 4-ClPh | CO | bond | 2 | O | $(CH_2)_3$ | sub. 35 |
| 864 | sub. 32 | 4-ClPh | CO | bond | 2 | O | $(CH_2)_3$ | sub. 35 |
| 865 | sub. 1 | 4-FPh | CO | bond | 2 | O | $(CH_2)_3$ | sub. 33 |
| 866 | sub. 2 | 4-FPh | CO | bond | 2 | O | $(CH_2)_3$ | sub. 33 |
| 867 | sub. 3 | 4-FPh | CO | bond | 2 | O | $(CH_2)_3$ | sub. 33 |
| 868 | sub. 4 | 4-FPh | CO | bond | 2 | O | $(CH_2)_3$ | sub. 33 |
| 869 | sub. 5 | 4-FPh | CO | bond | 2 | O | $(CH_2)_3$ | sub. 33 |
| 870 | sub. 6 | 4-FPh | CO | bond | 2 | O | $(CH_2)_3$ | sub. 33 |
| 871 | sub. 7 | 4-FPh | CO | bond | 2 | O | $(CH_2)_3$ | sub. 33 |
| 872 | sub. 8 | 4-FPh | CO | bond | 2 | O | $(CH_2)_3$ | sub. 33 |
| 873 | sub. 9 | 4-FPh | CO | bond | 2 | O | $(CH_2)_3$ | sub. 33 |
| 874 | sub. 10 | 4-FPh | CO | bond | 2 | O | $(CH_2)_3$ | sub. 33 |
| 875 | sub. 11 | 4-FPh | CO | bond | 2 | O | $(CH_2)_3$ | sub. 33 |
| 876 | sub. 12 | 4-FPh | CO | bond | 2 | O | $(CH_2)_3$ | sub. 33 |
| 877 | sub. 13 | 4-FPh | CO | bond | 2 | O | $(CH_2)_3$ | sub. 33 |
| 878 | sub. 14 | 4-FPh | CO | bond | 2 | O | $(CH_2)_3$ | sub. 33 |
| 879 | sub. 15 | 4-FPh | CO | bond | 2 | O | $(CH_2)_3$ | sub. 33 |
| 880 | sub. 16 | 4-FPh | CO | bond | 2 | O | $(CH_2)_3$ | sub. 33 |
| 881 | sub. 17 | 4-FPh | CO | bond | 2 | O | $(CH_2)_3$ | sub. 33 |
| 882 | sub. 18 | 4-FPh | CO | bond | 2 | O | $(CH_2)_3$ | sub. 33 |
| 883 | sub. 19 | 4-FPh | CO | bond | 2 | O | $(CH_2)_3$ | sub. 33 |
| 884 | sub. 20 | 4-FPh | CO | bond | 2 | O | $(CH_2)_3$ | sub. 33 |
| 885 | sub. 21 | 4-FPh | CO | bond | 2 | O | $(CH_2)_3$ | sub. 33 |
| 886 | sub. 22 | 4-FPh | CO | bond | 2 | O | $(CH_2)_3$ | sub. 33 |
| 887 | sub. 23 | 4-FPh | CO | bond | 2 | O | $(CH_2)_3$ | sub. 33 |
| 888 | sub. 24 | 4-FPh | CO | bond | 2 | O | $(CH_2)_3$ | sub. 33 |
| 889 | sub. 25 | 4-FPh | CO | bond | 2 | O | $(CH_2)_3$ | sub. 33 |
| 890 | sub. 26 | 4-FPh | CO | bond | 2 | O | $(CH_2)_3$ | sub. 33 |
| 891 | sub. 27 | 4-FPh | CO | bond | 2 | O | $(CH_2)_3$ | sub. 33 |
| 892 | sub. 28 | 4-FPh | CO | bond | 2 | O | $(CH_2)_3$ | sub. 33 |

TABLE 3-continued

| Cpd No. | $R^1$ | $R^2$ | A | B | n | D | E | Z |
|---|---|---|---|---|---|---|---|---|
| 893 | sub. 29 | 4-FPh | CO | bond | 2 | O | $(CH_2)_3$ | sub. 33 |
| 894 | sub. 30 | 4-FPh | CO | bond | 2 | O | $(CH_2)_3$ | sub. 33 |
| 895 | sub. 31 | 4-FPh | CO | bond | 2 | O | $(CH_2)_3$ | sub. 33 |
| 896 | sub. 32 | 4-FPh | CO | bond | 2 | O | $(CH_2)_3$ | sub. 33 |
| 897 | sub. 1 | 4-FPh | CO | bond | 2 | O | $(CH_2)_3$ | sub. 34 |
| 898 | sub. 2 | 4-FPh | CO | bond | 2 | O | $(CH_2)_3$ | sub. 34 |
| 899 | sub. 3 | 4-FPh | CO | bond | 2 | O | $(CH_2)_3$ | sub. 34 |
| 900 | sub. 4 | 4-FPh | CO | bond | 2 | O | $(CH_2)_3$ | sub. 34 |
| 901 | sub. 5 | 4-FPh | CO | bond | 2 | O | $(CH_2)_3$ | sub. 34 |
| 902 | sub. 6 | 4-FPh | CO | bond | 2 | O | $(CH_2)_3$ | sub. 34 |
| 903 | sub. 7 | 4-FPh | CO | bond | 2 | O | $(CH_2)_3$ | sub. 34 |
| 904 | sub. 8 | 4-FPh | CO | bond | 2 | O | $(CH_2)_3$ | sub. 34 |
| 905 | sub. 9 | 4-FPh | CO | bond | 2 | O | $(CH_2)_3$ | sub. 34 |
| 906 | sub. 10 | 4-FPh | CO | bond | 2 | O | $(CH_2)_3$ | sub. 34 |
| 907 | sub. 11 | 4-FPh | CO | bond | 2 | O | $(CH_2)_3$ | sub. 34 |
| 908 | sub. 12 | 4-FPh | CO | bond | 2 | O | $(CH_2)_3$ | sub. 34 |
| 909 | sub. 13 | 4-FPh | CO | bond | 2 | O | $(CH_2)_3$ | sub. 34 |
| 910 | sub. 14 | 4-FPh | CO | bond | 2 | O | $(CH_2)_3$ | sub. 34 |
| 911 | sub. 15 | 4-FPh | CO | bond | 2 | O | $(CH_2)_3$ | sub. 34 |
| 912 | sub. 16 | 4-FPh | CO | bond | 2 | O | $(CH_2)_3$ | sub. 34 |
| 913 | sub. 17 | 4-FPh | CO | bond | 2 | O | $(CH_2)_3$ | sub. 34 |
| 914 | sub. 18 | 4-FPh | CO | bond | 2 | O | $(CH_2)_3$ | sub. 34 |
| 915 | sub. 19 | 4-FPh | CO | bond | 2 | O | $(CH_2)_3$ | sub. 34 |
| 916 | sub. 20 | 4-FPh | CO | bond | 2 | O | $(CH_2)_3$ | sub. 34 |
| 917 | sub. 21 | 4-FPh | CO | bond | 2 | O | $(CH_2)_3$ | sub. 34 |
| 918 | sub. 22 | 4-FPh | CO | bond | 2 | O | $(CH_2)_3$ | sub. 34 |
| 919 | sub. 23 | 4-FPh | CO | bond | 2 | O | $(CH_2)_3$ | sub. 34 |
| 920 | sub. 24 | 4-FPh | CO | bond | 2 | O | $(CH_2)_3$ | sub. 34 |
| 921 | sub. 25 | 4-FPh | CO | bond | 2 | O | $(CH_2)_3$ | sub. 34 |
| 922 | sub. 26 | 4-FPh | CO | bond | 2 | O | $(CH_2)_3$ | sub. 34 |
| 923 | sub. 27 | 4-FPh | CO | bond | 2 | O | $(CH_2)_3$ | sub. 34 |
| 924 | sub. 28 | 4-FPh | CO | bond | 2 | O | $(CH_2)_3$ | sub. 34 |
| 925 | sub. 29 | 4-FPh | CO | bond | 2 | O | $(CH_2)_3$ | sub. 34 |
| 926 | sub. 30 | 4-FPh | CO | bond | 2 | O | $(CH_2)_3$ | sub. 34 |
| 927 | sub. 31 | 4-FPh | CO | bond | 2 | O | $(CH_2)_3$ | sub. 34 |
| 928 | sub. 32 | 4-FPh | CO | bond | 2 | O | $(CH_2)_3$ | sub. 34 |
| 929 | sub. 1 | 4-FPh | CO | bond | 2 | O | $(CH_2)_3$ | sub. 35 |
| 930 | sub. 2 | 4-FPh | CO | bond | 2 | O | $(CH_2)_3$ | sub. 35 |
| 931 | sub. 3 | 4-FPh | CO | bond | 2 | O | $(CH_2)_3$ | sub. 35 |
| 932 | sub. 4 | 4-FPh | CO | bond | 2 | O | $(CH_2)_3$ | sub. 35 |
| 933 | sub. 5 | 4-FPh | CO | bond | 2 | O | $(CH_2)_3$ | sub. 35 |
| 934 | sub. 6 | 4-FPh | CO | bond | 2 | O | $(CH_2)_3$ | sub. 35 |
| 935 | sub. 7 | 4-FPh | CO | bond | 2 | O | $(CH_2)_3$ | sub. 35 |
| 936 | sub. 8 | 4-FPh | CO | bond | 2 | O | $(CH_2)_3$ | sub. 35 |
| 937 | sub. 9 | 4-FPh | CO | bond | 2 | O | $(CH_2)_3$ | sub. 35 |
| 938 | sub. 10 | 4-FPh | CO | bond | 2 | O | $(CH_2)_3$ | sub. 35 |
| 939 | sub. 11 | 4-FPh | CO | bond | 2 | O | $(CH_2)_3$ | sub. 35 |
| 940 | sub. 12 | 4-FPh | CO | bond | 2 | O | $(CH_2)_3$ | sub. 35 |
| 941 | sub. 13 | 4-FPh | CO | bond | 2 | O | $(CH_2)_3$ | sub. 35 |
| 942 | sub. 14 | 4-FPh | CO | bond | 2 | O | $(CH_2)_3$ | sub. 35 |
| 943 | sub. 15 | 4-FPh | CO | bond | 2 | O | $(CH_2)_3$ | sub. 35 |
| 944 | sub. 16 | 4-FPh | CO | bond | 2 | O | $(CH_2)_3$ | sub. 35 |
| 945 | sub. 17 | 4-FPh | CO | bond | 2 | O | $(CH_2)_3$ | sub. 35 |
| 946 | sub. 18 | 4-FPh | CO | bond | 2 | O | $(CH_2)_3$ | sub. 35 |
| 947 | sub. 19 | 4-FPh | CO | bond | 2 | O | $(CH_2)_3$ | sub. 35 |
| 948 | sub. 20 | 4-FPh | CO | bond | 2 | O | $(CH_2)_3$ | sub. 35 |
| 949 | sub. 21 | 4-FPh | CO | bond | 2 | O | $(CH_2)_3$ | sub. 35 |
| 950 | sub. 22 | 4-FPh | CO | bond | 2 | O | $(CH_2)_3$ | sub. 35 |
| 951 | sub. 23 | 4-FPh | CO | bond | 2 | O | $(CH_2)_3$ | sub. 35 |
| 952 | sub. 24 | 4-FPh | CO | bond | 2 | O | $(CH_2)_3$ | sub. 35 |
| 953 | sub. 25 | 4-FPh | CO | bond | 2 | O | $(CH_2)_3$ | sub. 35 |
| 954 | sub. 26 | 4-FPh | CO | bond | 2 | O | $(CH_2)_3$ | sub. 35 |
| 955 | sub. 27 | 4-FPh | CO | bond | 2 | O | $(CH_2)_3$ | sub. 35 |
| 956 | sub. 28 | 4-FPh | CO | bond | 2 | O | $(CH_2)_3$ | sub. 35 |
| 957 | sub. 29 | 4-FPh | CO | bond | 2 | O | $(CH_2)_3$ | sub. 35 |
| 958 | sub. 30 | 4-FPh | CO | bond | 2 | O | $(CH_2)_3$ | sub. 35 |
| 959 | sub. 31 | 4-FPh | CO | bond | 2 | O | $(CH_2)_3$ | sub. 35 |
| 960 | sub. 32 | 4-FPh | CO | bond | 2 | O | $(CH_2)_3$ | sub. 35 |
| 961 | sub. 36 | 3,4-diClPh | CO | bond | 1 | O | $CH_2CH_2$ | sub. 33 |
| 962 | sub. 37 | 3,4-diClPh | CO | bond | 1 | O | $CH_2CH_2$ | sub. 33 |
| 963 | sub. 38 | 3,4-diClPh | CO | bond | 1 | O | $CH_2CH_2$ | sub. 33 |
| 964 | sub. 36 | 3,4-diClPh | CO | bond | 1 | O | $CH_2CH_2$ | sub. 34 |
| 965 | sub. 37 | 3,4-diClPh | CO | bond | 1 | O | $CH_2CH_2$ | sub. 34 |
| 966 | sub. 38 | 3,4-diClPh | CO | bond | 1 | O | $CH_2CH_2$ | sub. 34 |
| 967 | sub. 36 | 3,4-diClPh | CO | bond | 1 | O | $CH_2CH_2$ | sub. 35 |
| 968 | sub. 37 | 3,4-diClPh | CO | bond | 1 | O | $CH_2CH_2$ | sub. 35 |

TABLE 3-continued

| Cpd No. | $R^1$ | $R^2$ | A | B | n | D | E | Z |
|---|---|---|---|---|---|---|---|---|
| 969 | sub. 38 | 3,4-diClPh | CO | bond | 1 | O | $CH_2CH_2$ | sub. 35 |
| 970 | sub. 36 | 3,4-diClPh | CO | bond | 2 | O | $CH_2CH_2$ | sub. 33 |
| 971 | sub. 37 | 3,4-diClPh | CO | bond | 2 | O | $CH_2CH_2$ | sub. 33 |
| 972 | sub. 38 | 3,4-diClPh | CO | bond | 2 | O | $CH_2CH_2$ | sub. 33 |
| 973 | sub. 36 | 3,4-diClPh | CO | bond | 2 | O | $CH_2CH_2$ | sub. 34 |
| 974 | sub. 37 | 3,4-diClPh | CO | bond | 2 | O | $CH_2CH_2$ | sub. 34 |
| 975 | sub. 38 | 3,4-diClPh | CO | bond | 2 | O | $CH_2CH_2$ | sub. 34 |
| 976 | sub. 36 | 3,4-diClPh | CO | bond | 2 | O | $CH_2CH_2$ | sub. 35 |
| 977 | sub. 37 | 3,4-diClPh | CO | bond | 2 | O | $CH_2CH_2$ | sub. 35 |
| 978 | sub. 38 | 3,4-diClPh | CO | bond | 2 | O | $CH_2CH_2$ | sub. 35 |
| 979 | sub. 36 | 3,4-diFPh | CO | bond | 2 | O | $CH_2CH_2$ | sub. 33 |
| 980 | sub. 37 | 3,4-diFPh | CO | bond | 2 | O | $CH_2CH_2$ | sub. 33 |
| 981 | sub. 38 | 3,4-diFPh | CO | bond | 2 | O | $CH_2CH_2$ | sub. 33 |
| 982 | sub. 36 | 3,4-diFPh | CO | bond | 2 | O | $CH_2CH_2$ | sub. 34 |
| 983 | sub. 37 | 3,4-diFPh | CO | bond | 2 | O | $CH_2CH_2$ | sub. 34 |
| 984 | sub. 38 | 3,4-diFPh | CO | bond | 2 | O | $CH_2CH_2$ | sub. 34 |
| 985 | sub. 36 | 3,4-diFPh | CO | bond | 2 | O | $CH_2CH_2$ | sub. 35 |
| 986 | sub. 37 | 3,4-diFPh | CO | bond | 2 | O | $CH_2CH_2$ | sub. 35 |
| 987 | sub. 38 | 3,4-diFPh | CO | bond | 2 | O | $CH_2CH_2$ | sub. 35 |
| 988 | sub. 36 | 4-ClPh | CO | bond | 2 | O | $CH_2CH_2$ | sub. 33 |
| 989 | sub. 37 | 4-ClPh | CO | bond | 2 | O | $CH_2CH_2$ | sub. 33 |
| 990 | sub. 38 | 4-ClPh | CO | bond | 2 | O | $CH_2CH_2$ | sub. 33 |
| 991 | sub. 36 | 4-ClPh | CO | bond | 2 | O | $CH_2CH_2$ | sub. 34 |
| 992 | sub. 37 | 4-ClPh | CO | bond | 2 | O | $CH_2CH_2$ | sub. 34 |
| 993 | sub. 38 | 4-ClPh | CO | bond | 2 | O | $CH_2CH_2$ | sub. 34 |
| 994 | sub. 36 | 4-ClPh | CO | bond | 2 | O | $CH_2CH_2$ | sub. 35 |
| 995 | sub. 37 | 4-ClPh | CO | bond | 2 | O | $CH_2CH_2$ | sub. 35 |
| 996 | sub. 38 | 4-ClPh | CO | bond | 2 | O | $CH_2CH_2$ | sub. 35 |
| 997 | sub. 36 | 4-FPh | CO | bond | 2 | O | $CH_2CH_2$ | sub. 33 |
| 998 | sub. 37 | 4-FPh | CO | bond | 2 | O | $CH_2CH_2$ | sub. 33 |
| 999 | sub. 38 | 4-FPh | CO | bond | 2 | O | $CH_2CH_2$ | sub. 33 |
| 1000 | sub. 36 | 4-FPh | CO | bond | 2 | O | $CH_2CH_2$ | sub. 34 |
| 1001 | sub. 37 | 4-FPh | CO | bond | 2 | O | $CH_2CH_2$ | sub. 34 |
| 1002 | sub. 38 | 4-FPh | CO | bond | 2 | O | $CH_2CH_2$ | sub. 34 |
| 1003 | sub. 36 | 4-FPh | CO | bond | 2 | O | $CH_2CH_2$ | sub. 35 |
| 1004 | sub. 37 | 4-FPh | CO | bond | 2 | O | $CH_2CH_2$ | sub. 35 |
| 1005 | sub. 38 | 4-FPh | CO | bond | 2 | O | $CH_2CH_2$ | sub. 35 |
| 1006 | sub. 36 | 3,4-diClPh | CO | bond | 1 | O | $(CH_2)_3$ | sub. 33 |
| 1007 | sub. 37 | 3,4-diClPh | CO | bond | 1 | O | $(CH_2)_3$ | sub. 33 |
| 1008 | sub. 38 | 3,4-diClPh | CO | bond | 1 | O | $(CH_2)_3$ | sub. 33 |
| 1009 | sub. 36 | 3,4-diClPh | CO | bond | 1 | O | $(CH_2)_3$ | sub. 34 |
| 1010 | sub. 37 | 3,4-diClPh | CO | bond | 1 | O | $(CH_2)_3$ | sub. 34 |
| 1011 | sub. 38 | 3,4-diClPh | CO | bond | 1 | O | $(CH_2)_3$ | sub. 34 |
| 1012 | sub. 36 | 3,4-diClPh | CO | bond | 1 | O | $(CH_2)_3$ | sub. 35 |
| 1013 | sub. 37 | 3,4-diClPh | CO | bond | 1 | O | $(CH_2)_3$ | sub. 35 |
| 1014 | sub. 38 | 3,4-diClPh | CO | bond | 1 | O | $(CH_2)_3$ | sub. 35 |
| 1015 | sub. 36 | 3,4-diClPh | CO | bond | 2 | O | $(CH_2)_3$ | sub. 33 |
| 1016 | sub. 37 | 3,4-diClPh | CO | bond | 2 | O | $(CH_2)_3$ | sub. 33 |
| 1017 | sub. 38 | 3,4-diClPh | CO | bond | 2 | O | $(CH_2)_3$ | sub. 33 |
| 1018 | sub. 36 | 3,4-diClPh | CO | bond | 2 | O | $(CH_2)_3$ | sub. 34 |
| 1019 | sub. 37 | 3,4-diClPh | CO | bond | 2 | O | $(CH_2)_3$ | sub. 34 |
| 1020 | sub. 38 | 3,4-diClPh | CO | bond | 2 | O | $(CH_2)_3$ | sub. 34 |
| 1021 | sub. 36 | 3,4-diClPh | CO | bond | 2 | O | $(CH_2)_3$ | sub. 35 |
| 1022 | sub. 37 | 3,4-diClPh | CO | bond | 2 | O | $(CH_2)_3$ | sub. 35 |
| 1023 | sub. 38 | 3,4-diClPh | CO | bond | 2 | O | $(CH_2)_3$ | sub. 35 |
| 1024 | sub. 36 | 3,4-diFPh | CO | bond | 2 | O | $(CH_2)_3$ | sub. 33 |
| 1025 | sub. 37 | 3,4-diFPh | CO | bond | 2 | O | $(CH_2)_3$ | sub. 33 |
| 1026 | sub. 38 | 3,4-diFPh | CO | bond | 2 | O | $(CH_2)_3$ | sub. 33 |
| 1027 | sub. 36 | 3,4-diFPh | CO | bond | 2 | O | $(CH_2)_3$ | sub. 34 |
| 1028 | sub. 37 | 3,4-diFPh | CO | bond | 2 | O | $(CH_2)_3$ | sub. 34 |
| 1029 | sub. 38 | 3,4-diFPh | CO | bond | 2 | O | $(CH_2)_3$ | sub. 34 |
| 1030 | sub. 36 | 3,4-diFPh | CO | bond | 2 | O | $(CH_2)_3$ | sub. 35 |
| 1031 | sub. 37 | 3,4-diFPh | CO | bond | 2 | O | $(CH_2)_3$ | sub. 35 |
| 1032 | sub. 38 | 3,4-diFPh | CO | bond | 2 | O | $(CH_2)_3$ | sub. 35 |
| 1033 | sub. 36 | 4-ClPh | CO | bond | 2 | O | $(CH_2)_3$ | sub. 33 |
| 1034 | sub. 37 | 4-ClPh | CO | bond | 2 | O | $(CH_2)_3$ | sub. 33 |
| 1035 | sub. 38 | 4-ClPh | CO | bond | 2 | O | $(CH_2)_3$ | sub. 33 |
| 1036 | sub. 36 | 4-ClPh | CO | bond | 2 | O | $(CH_2)_3$ | sub. 34 |
| 1037 | sub. 37 | 4-ClPh | CO | bond | 2 | O | $(CH_2)_3$ | sub. 34 |
| 1038 | sub. 38 | 4-ClPh | CO | bond | 2 | O | $(CH_2)_3$ | sub. 34 |
| 1039 | sub. 36 | 4-ClPh | CO | bond | 2 | O | $(CH_2)_3$ | sub. 35 |
| 1040 | sub. 37 | 4-ClPh | CO | bond | 2 | O | $(CH_2)_3$ | sub. 35 |
| 1041 | sub. 38 | 4-ClPh | CO | bond | 2 | O | $(CH_2)_3$ | sub. 35 |
| 1042 | sub. 36 | 4-FPh | CO | bond | 2 | O | $(CH_2)_3$ | sub. 33 |
| 1043 | sub. 37 | 4-FPh | CO | bond | 2 | O | $(CH_2)_3$ | sub. 33 |
| 1044 | sub. 38 | 4-FPh | CO | bond | 2 | O | $(CH_2)_3$ | sub. 33 |

TABLE 3-continued

| Cpd No. | $R^1$ | $R^2$ | A | B | n | D | E | Z |
|---|---|---|---|---|---|---|---|---|
| 1045 | sub. 36 | 4-FPh | CO | bond | 2 | O | $(CH_2)_3$ | sub. 34 |
| 1046 | sub. 37 | 4-FPh | CO | bond | 2 | O | $(CH_2)_3$ | sub. 34 |
| 1047 | sub. 38 | 4-FPh | CO | bond | 2 | O | $(CH_2)_3$ | sub. 34 |
| 1048 | sub. 36 | 4-FPh | CO | bond | 2 | O | $(CH_2)_3$ | sub. 35 |
| 1049 | sub. 37 | 4-FPh | CO | bond | 2 | O | $(CH_2)_3$ | sub. 35 |
| 1050 | sub. 38 | 4-FPh | CO | bond | 2 | O | $(CH_2)_3$ | sub. 35 |

In the above table, the compounds of Compound Nos. 1 to 192 and Compound Nos. 321 to 384 are preferred, of which the compounds of Compound Nos. 97 to 192 are still more preferred and the compounds of Compound Nos. 101 to 106, 133 to 138 and 165 to 170 are still more preferred.

The most preferred compounds are:

1-{2-[(2R)-(3,4-dichlorophenyl)-4-(3,4,5-trimethoxybenzoyl)morpholin-2-yl]ethyl}spiro[(2-hydroxy)indane-1,4'-piperidine], 1-{2-[(2R)-(3,4-dichlorophenyl)4-(3,4,5-trimethoxybenzoyl)morpholin-2-yl]ethyl}spiro[(3-hydroxy)indane-1,4'-piperidine], 1-{(2-[(2R)-(3,4-dichlorophenyl)-4-(3,4,5-trimethoxybenzoyl)morpholin-2-yl]ethyl}spiro[1H-indene-1,4'-piperidine], 1-{2-[(2R)-(3,4-dichlorophenyl)-4-(3,5-dimethoxybenzoyl) morpholin-2-yl]ethyl}spiro[(2-hydroxy)indane-1,4'-piperidine], 1-{2-[(2R)-(3,4-dichlorophenyl)-4-(3,5-dimethoxybenzoyl) morpholin-2-yl]ethyl}spiro[(3-hydroxy)indane-1,4'-piperidine], and 1-{2-[(2R)-(3,4-dichlorophenyl)-4-(3,5-dimethoxybenzoyl) morpholin-2-yl]ethyl}spiro[(1H-indene-1,4'-piperidine, particularly preferred compounds are 1-{2-[(2R)-(3,4-dichlorophenyl)-4-(3,4,5-trimethoxybenzoyl)morpholin-2-yl]ethyl}spiro[(2-hydroxy)indane-1,4'-piperidine] and 1-{2-[(2R)-(3,4-dichlorophenyl)-4-(3,4,5-trimethoxybenzoyl)morpholin-2-yl]ethyl}spiro[(3-hydroxy)indane-1,4'-piperidine].

REFERENTIAL EXAMPLES

The present invention will hereafter be described with reference to referential examples.

Referential Example 1

N-t-Butoxycarbonyl-spiro(1H-indene-1,4'-piperidine)

In 60 ml of anhydrous tetrahydrofuran, 11.6 g (0.10 mole) of indene were dissolved, followed by the gradual dropwise addition of 200 ml (0.20 mole) of lithium bistrimethylsilylamide (a 1.0M tetrahydrofuran solution) for one hour under ice cooling. After stirring the reaction mixture for 30 minutes, 50 ml of a tetrahydrofuran solution of 24.2 g (0.10 mole) of N-t-butoxycarbonyl-bis(2-chloroethyl)amine were added dropwise to the reaction mixture for 20 minutes. The resulting mixture was further stirred for 2 hours under ice cooling. The reaction mixture was distilled under reduced pressure. The residue was purified by silica gel column chromatography (eluent; n-hexane:ethyl acetate=97:3), whereby 21.3 g (89%) of the title compound were obtained as white crystals.

Nuclear magnetic resonance spectrum (400 MHz, $CDCl_3$) δ ppm: 7.21–7.41 (4H,m), 6.85 (1H,d,J=5.7 Hz), 6.79 (1H, d,J=5.7 Hz), 4.11–4.28 (2H,m), 3.07–3.23 (2H,m), 2.01 (2H,dt,J=12.8,4.5 Hz), 1.51 (9H,s), 1.47–1.50(2H,m)

Infrared absorption spectrum $\nu_{max}$ $cm^{-1}$ (KBr): 2965, 1680, 1425, 1365, 1245, 1165

Mass spectrometric analysis (EI) m/z: 285 ($M^+$)

Referential Example 2

N-t-Butoxycarbonyl-spiro[(2-hydroxy)indane-1,4'-piperidine] and N-t-Butoxycarbonyl-spiro[(3-hydroxy)indane-1,4'-piperidine]

In 100 ml of anhydrous tetrahydrofuran, 10.0 g (35.0 mmol) of N-t-butoxycarbonyl-spiro(1H-indene-1,4'-piperidine), prepared as described in Referential Example 1, were dissolved, followed by the dropwise addition of 52.5 ml (52.5 mmol) of borane.tetrahydrofuran complex (a 1.0M tetrahydrofuran solution) for 1.5 hours under ice cooling. The resulting mixture was stirred for 30 minutes under ice cooling and then for 4 hours at room temperature. Under ice cooling, 5 ml of ethanol were added to the reaction mixture. After stirring for a further 5 minutes, 13 ml of a 6N aqueous solution of sodium hydroxide were added dropwise to the reaction mixture for 20 minutes. Then, 13.0 ml of 30% aqueous hydrogen peroxide were added dropwise for 25 minutes, followed by stirring for 20 minutes under ice cooling and 3 hours at room temperature. The reaction mixture was poured into water, followed by extraction with ethyl acetate. The organic layer was washed with saturated NaCl solution and dried over anhydrous sodium sulfate. The solvent was then distilled off under reduced pressure. The resulting residue was purified by silica gel column chromatography (eluent; n-hexane:ethyl acetate=70:30–60:40), whereby 5.83 g (55%) of N-t-butoxycarbonyl-spiro[(2-hydroxy)indane-1,4'-piperidine] were obtained as a nonpolar substance and 4.20 g (40%) of N-t-butoxycarbonyl-spiro [(3-hydroxy)indane-1,4'-piperidine] as a polar substance, each as white crystals.

N-t-Butoxycarbonyl-spiro [(2-hydroxy)indane-1,4'-piperidine]

Nuclear magnetic resonance spectrum (400 MHz, $CDCl_3$) δ ppm: 7.20–7.29 (4H,m), 4.48–4.52 (1H,m), 3.96 (2H,brs), 3.32 (1H,dd,J=16.7,5.3 Hz), 3.24 (2H,m), 2.86 (1H,dd,J=16.7,1.0 Hz), 2.02–2.06 (1H,m), 1.84 (1H,m), 1.52–1.65 (3H,m), 1.49 (9H,s)

Infrared-absorption spectrum $\nu_{max}$ $cm^{-1}$ (KBr): 3620, 2980, 2935, 1680, 1430, 1365

Mass spectrometric analysis (EI) m/z: 303 ($M^+$).

N-t-Butoxycarbonyl-spiro[(3-hydroxy)indane-1,4'-piperidine]

Nuclear magnetic resonance spectrum (400 MHz, $CDCl_3$) δ ppm: 7.42 (1H,d,J=7.0 Hz), 7.26–7.36 (2H,m), 7.23 (1H, d,J=7.0 Hz), 5.29 (1H,d,J=6.2 Hz), 4.12 (2H,m), 2.95 (2H, m), 2.53 (1H,q,J=6.9 Hz), 1.91–1.98 (2H,m), 1.72–1.80 (2H,m), 1.61–1.67 (1H,m), 1.49 (9H,s), 1.38–1.42 (1H,m)

Infrared absorption spectrum $\nu_{max}$ $cm^{-1}$ (KBr): 3605, 2980, 2935, 1680, 1430, 1365

Mass spectrometric analysis (EI) m/z: 303 ($M^+$)

Referential Example 3

Spiro[(2-hydroxy)indane-1,4'-piperidine] hydrochloride

In 10 ml of ethanol, 2.51 g (8.27 mmol) of N-t-butoxycarbonyl-spiro[(2-hydroxy)indane-1,4'-piperidine], prepared as described in Referential Example 2, were dissolved, followed by the dropwise addition of 10.0 ml (40.0 mmol) of 4N hydrochloric acid/dioxane solution for 5 minutes under ice cooling. After stirring it for 30 minutes under ice cooling, the mixture was further stirred at room temperature for 4 hours. The solvent of the reaction mixture was distilled off under reduced pressure. The residue was recrystallized from methanol/diethyl ether, whereby 1.64 g (83%) of the title compound were obtained as white crystals.

Melting point: 250–251° C.

Nuclear magnetic resonance spectrum (400 MHz, DMSO-$d_6$) δ ppm: 8.99 (2H,m), 7.13–7.22 (4H,m), 5.19 (1H,s), 4.38 (1H,s), 3.13–3.26 (5H,m), 2.77 (1H,dd,J=16.5, 3.2 Hz), 2.07 (1H,d,J=14.0 Hz), 1.82–1.99 (2H,m), 1.60 (d,J=14.0 Hz)

Infrared absorption spectrum $\nu_{max}$ $cm^{-1}$ (KBr): 3390, 2973, 2826, 1598.

Mass spectrometric analysis (EI) m/z: 203 ($M^+$)(free form)

Referential Example 4

N-t-Butoxycarbonyl-spiro[(3-indanone)-1,4'-piperidine]

In 40 ml of methylene chloride, 2.00 g (6.59 mmol) of N-t-butoxycarbonyl-spiro[(3-hydroxy)indane)-1,4'-piperidine], prepared as described in Referential Example 2, were dissolved. To the resulting solution, 12.0 g of powdered molecular sieves 4A and 2.84 g (13.2 mmol) of pyridinium chlorochromate were added under ice cooling, followed by stirring for 30 minutes. The mixture was further stirred for 2 hours at room temperature. After the addition of 80 ml of diethyl ether to the reaction mixture, the resulting mixture was filtered through Celite. The filtrate was concentrated under reduced pressure. The residue was purified by silica gel column chromatography (eluent; n-hexane:ethyl acetate=75:25), whereby 1.98 g (99%) of the title compound were obtained as white crystals.

Nuclear magnetic resonance spectrum (400 MHz, $CDCl_3$) δ ppm: 7.75 (1H,d,J=8.0 Hz), 7.65 (1H,dd,J=8.0,8.0 Hz), 7.49 (1H,d, J=8.0 Hz), 7.42 (1H,dd,J=8.0,8.0 Hz), 4.23 (2H,brs), 2.86 (2H,m), 2.64 (2H,s), 1.99 (2H,dt,J=13.2,4.4 Hz), 1.50–1.53 (11H,m)

Infrared absorption spectrum $\nu_{max}$ $cm^{-1}$ ($CHCl_3$): 2980, 2940, 1710, 1685, 1430

Mass spectrometric analysis (FAB) m/z: 301 ($M^+$)

Referential Example 5

Spiro[(3-indanone)-1,4'-piperidine]hydrochloride

In 20 ml of ethanol , 1.94 g (6.50 mmol) of N-t-butoxycarbonyl- spiro[(3-indanone)-1,4'-piperidine], prepared as described in Referential Example 4, were dissolved, followed by the dropwise addition of 17.0 ml (65.0 mmol) of 4N hydrogen chloride/dioxane for 5 minutes under ice cooling. After stirring for 30 minutes, the mixture was further stirred for 2 hours at room temperature. The solvent of the reaction mixture was distilled off under reduced pressure and the residue was recrystallized from methanol/diethyl ether, whereby 1.46 g (94%) of the title compound were obtained as white crystals.

Melting point: 227–228° C.

Nuclear magnetic resonance spectrum (400 MHz, DMSO-$d_6$) δ ppm: 9.07 (2H,brs), 7.78 (1H,dd,J=7.8,7.8 Hz), 7.65 (1H,d,J=7.8 Hz), 7.59 (1H,d,J=7.8 Hz), 7.50 (1H,dd, J=7.8,7.8 Hz), 3.34–3.37 (2H,m), 2.99–3.05 (2H,m), 2.76 (2H,s), 2.27 (2H,dt,J=13.8,4.1 Hz), 1.64–1.68 (2H,m)

Infrared absorption spectrum $\nu_{max}$ $cm^{-1}$ (KBr): 3030, 2703, 2500, 1690, 1610, 1470

Mass spectrometric analysis (EI) m/z: 201 ($M^+$)(free form)

Referential Example 6

N-t-Butoxycarbonyl-spiro[((2S)-hydroxy)indane-1,4'-piperidine]

To 0.42 ml (0.42 mmol) of a 1.0M toluene solution of (R)-2-methyl-CBS-oxazaborolidine, a tetrahydrofuran (8.3 ml) solution of 2.5 g (8.30 mmol) of N-t-butoxycarbonyl-spiro[(2-indanone)-1,4'-piperidine] and 4.2 ml of a 1M tetrahydrofuran solution of borane-tetrahydrofuran complex were added, each at a rate of 1.0 ml/min. The resulting mixture was stirred at room temperature for 1 hour, followed by the addition of water under ice cooling. After extraction of the reaction mixture with ethyl acetate, the organic layer was washed with saturated NaCl solution and dried over anhydrous sodium sulfate. The solvent was then distilled off under reduced pressure. The residue was purified by silica gel column chromatography (eluent; hexane:ethyl acetate=1:1), whereby 2.51 g (yield: 100%, optical purity: 89% ee) of N-t-butoxycarbonyl-spiro[((2S)-hydroxy)indane-1,4'-piperidine] were obtained as white crystals.

The resulting crystals were dissolved in 5.0 ml of ethyl acetate under heating in a water bath. After the addition of 150 ml of hexane, the resulting mixture was allowed to stand, whereby 1.9 g of white crystals were obtained. The same procedure was repeated again, whereby 1.52 g (yield: 61%, optical purity: 100% ee) of N-t-butoxycarbonyl-spiro[((2S)-hydroxy)indane-1,4'-piperidine] were obtained as white crystals. (Incidentally, the optical purity of the title compound was determined by subjecting the nitrobenzoyl derivative of the title compound, which is prepared as described in Referential Example 8, to high-performance liquid chromatography (HPLC).)

Melting point: 106° C.

$[\alpha]_D^{24}$+50.0° (c=1.0, methanol)

Nuclear magnetic resonance spectrum (400 MHz, $CDCl_3$) δ ppm: 7.28–7.18 (4H,m), 4.50 (1H,dd,J=4.9,1.9 Hz), 4.07–3.83 (2H,m), 3.32 (1H,dd,J=16.7 Hz,4.9 Hz), 3.30–3.12 (2H,m), 2.86 (1H,dd,J=16.7 Hz,1.9 Hz), 2.08–1.99 (1H,m), 1.89–1.78 (1H,m), 1.49(9H,s), 1.64–1.42 (2H,m)

Infrared absorption spectrum $\nu_{max}$ $cm^{-1}$ (KBr): 3349, 2934, 1698,1425,1367, 1168,1162

Mass spectrometric analysis (FAB) m/z: 304 ($[M+H]^+$)

Elemental analysis (% based on $C_{18}H_{25}NO_3$)

Calculated: C; 71.26, H; 8.31, N; 4.62 Found: C; 70.99, H; 8.24, N; 4.68

Referential Example 7

Spiro[((2S)-hydroxy)indane-1,4'-piperidine] hydrochloride

In 12.4 ml of ethanol, 1.5 g (4.95 mmol) of N-t-butoxycarbonyl-spiro[((2S)-hydroxy)indane-1,4'-piperidine], prepared as described in Referential Example 6, were dissolved. To the resulting solution, 6.2 ml of 4N hydrogen chloride-1,4-dioxane were added under ice cooling, followed by stirring at room temperature for 5 hours. The solvent was then distilled off under reduced pressure. The residue was washed with ether, whereby 1.1 g (yield: 93%) of spiro[((2S)-hydroxy)indane-1,4'-piperidine] hydrochloride were obtained as white crystals.

Melting point: 247° C.

$[\alpha]_D^{24}$+46.2° (c=0.50, methanol)

Nuclear magnetic resonance spectrum (400 MHz, DMSO-$d_6$) δ ppm: 8.98 (2H,m), 7.22–7.17 (4H,m), 5.20 (1H,d,J=5.0 Hz), 4.40–4.37 (1H,m), 3.26–3.13 (5H,m), 2.77 (1H,dd,J=16.5 Hz,3.2 Hz), 2.07 (1H,d,J=14.0 Hz), 1.99–1.82 (2H,m), 1.60 (1H,d,J=14.0 Hz)

Infrared absorption spectrum $\nu_{max}$ $cm^{-1}$ (KBr): 3413, 3269, 2937, 1607, 1431, 1074, 765

Mass spectrometric analysis (EI) m/z: 203 ($M^+$ free form)

Elemental analysis (% based on $C_{13}H_{17}NO.HCl$)

Calculated: C; 65.13, H; 7.57, N; 5.84, Cl; 14.79 Found: C; 64.89, H; 7.48, N; 5.82, Cl; 15.01

Referential Example 8

N-t-Butoxycarbonyl-spiro[(2S)-(4-nitrobenzoyloxy) indane-1,4'-piperidine]

In 2.0 ml of methylene chloride, 30.3 mg (0.1 mmol) of N-t-butoxycarbonyl-spiro[((2S)-hydroxy)indane-1,4'-piperidine], prepared as described in Referential Example 6, were dissolved. To the resulting solution, 0.042 ml (0.3 mmol) of triethylamine, 1.2 mg (0.01 mmol) of 4-dimethylaminopyridine and 28 mg (0.15 mmol) of 4-nitrobenzoyl chloride were added, followed by stirring at room temperature for 3 hours. The solvent of the reaction mixture was distilled off under reduced pressure. The residue was purified by silica gel column chromatography (eluent; n-hexane:ethyl acetate=2:1), whereby 42 mg (yield: 93%, optical purity: 100% ee) of N-t-butoxycarbonyl-spiro [(2S)-(4-nitrobenzoyloxy)indane-1,4'-piperidine] were obtained as white crystals. The optical purity of the compound was determined by HPLC analysis.

Melting point: 75.6° C.

$[\alpha]_D^{24}$+141.5° (c=1.18, chloroform)

Nuclear magnetic resonance spectrum (400 MHz, $CDCl_3$) δ ppm: 8.25 (2H,d,J=8.9 Hz), 8.11 (2H,d,J=8.9 Hz), 7.34–7.17 (4H,m), 5.83 (1H,d,J=5.3 Hz), 4.11–3.84 (2H,m), 3.52 (1H,dd,J=17.4 Hz,5.3 Hz), 3.32–3.13 (1H,m), 3.04 (1H,d,J=17.4 Hz), 3.02–2.92 (1H,m), 2.16–1.97 (2H,m), 1.73–1.58 (2H, m), 1.47 (9H, s)

Infrared absorption spectrum $\nu_{max}$ $cm^{-1}$ (KBr): 2975, 1723, 1695, 1530, 1279, 1167

Mass spectrometric analysis (FAB) m/z: 452 ($[M+H]^+$)

Elemental analysis (% based on $C_{25}H_{28}N_2O_6$)

Calculated: C; 66.36, H; 6.24, N; 6.19, O; 21.21 Found: C; 66.33, H; 6.37, N; 5.95

HPLC analysis:

Column; Chiral Cel AD (product of Daicel Chemical Industries, Ltd., inner diameter: 4.6 mm, length: 250 mm)

Eluent; hexane: 2-propanol=50:50

Flow rate; 0.5 ml/min.

Temperature; 40° C.

Detection; 254 nm

Retention time; 17.1 min.

Referential Example 9

N-t-Butoxycarbonyl-spiro[((2R)-hydroxy)indane-1, 4'-piperidine]

Using 0.083 ml (0.083 mmol) of a 1.0M toluene solution of (S)-2-methyl-CBS-oxazaborazine and 0.5 g (1.66 mmol) of N-t-butoxycarbonyl-spiro[(2-indanone)-1,4'-piperidine], 215 mg (yield: 43%, optical purity: 100% ee) of N-t-butoxycarbonyl-spiro[((2R)-hydroxy)-indane-1,4'-piperidine] were obtained as white crystals in a similar manner to that described in Referential example 6. (The optical purity of the title compound was determined by subjecting the nitrobenzoyl derivative of the title compound, which is prepared as described in Referential Example 10, to HPLC.)

The melting point, Nuclear Magnetic Resonance spectrum, Infrared absorption spectrum and Mass spectrometric analysis of the resulting compound coincided with those of the (S)-form prepared in Referential Example 6.

$[\alpha]_D^{24}$−51.7° (c=1.0, methanol)

Elemental analysis (% based on $C_{18}H_{25}NO_3$)

Calculated: C; 71.26, H; 8.31, N; 4.62 Found: C; 71.09, H; 8.25, N; 4.68

Referential Example 10

N-t-Butoxycarbonyl-spiro[(2R)-(4-nitrobenzoyloxy) indane-1,4'-piperidine]

Using 30.3 mg (0.1 mmol) of N-t-butoxycarbonyl-spiro [((2R)-hydroxy)indane-1,4'-piperidine], prepared as described in Referential Example 9, 43 mg (yield: 95%, optical purity: 100% ee) of N-t-butoxycarbonyl-spiro[(2R)-(4-nitrobenzoyloxy)indane-1,4'-piperidine] were obtained as white crystals in a similar manner to that described in Referential Example 8. The optical purity of the compound was determined by HPLC analysis.

The melting point, Nuclear Magnetic Resonance spectrum, Infrared absorption spectrum and Mass spectrometric analysis of the resulting compound coincided with those of the (S)-form prepared in Referential Example 8.

$[\alpha]_D^{24}$−139.9° (c=0.76, chloroform)

Elemental analysis (% based on $C_{25}H_{28}N_2O_6.1/4H_2O$)

Calculated: C; 65.70, H; 6.29, N; 6.13 Found: C; 65.97, H; 6.38, N; 6.01

HPLC analysis:

Column; Chiral Cel AD (product of Daicel Chemical Industries, Ltd. inner diameter: 4.6 mm, length: 250 mm)

Eluent; hexane : 2-propanol=50:50

Flow rate; 0.5 ml/min.

Temperature; 40° C.

Detection; 254 mm

Retention time; 10.1 min.

Referential Example 11

N-t-Butoxycarbonyl-spiro[((2R,3S)-epoxy)indane-1, 4'-piperidine]

In 2.0 ml of methylene chloride, 100 mg (0.35 mmol) of N-t-butoxycarbonyl-spiro[1H-indene-1,4'-piperidine] were dissolved. To the resulting solution, 11.4 mg (0.018 mmol) of (S,S)-(+)-N,N'-bis(3,5-di-t-butylsalicylidene)-1,2-cyclohexanediaminomanganese (III) chloride were added, followed by the addition of 19 mg (0.11 mmol) of 4-phenylpyridine-N-oxide. The resulting mixture was stirred for 10 minutes. After the addition of 1.1 ml (0.7 mmol) of a 1.0M aqueous solution of sodium hypochlorite to the mixture, the resulting mixture was stirred for 2 hours. Water was added to the reaction mixture and the resulting mixture was extracted with ethyl acetate. The organic layer was washed with saturated NaCl aqueous solution and then dried over anhydrous sodium sulfate. The solvent of the extract was distilled off under reduced pressure. The residue was subjected to preparative thin layer chromatography (developing agent; hexane:ethyl acetate=2:1), whereby 53.6 mg (yield: 51%, optical purity: 91% ee) of N-t-butoxycarbonyl-spiro[((2R,3 S)-epoxy)indane-1,4'-piperidine] were obtained as white crystals.

The optical purity of the compound was determined by HPLC analysis.

Melting point: 149° C.

$[\alpha]_D^{25}$+62.2° (c=1.0, methanol, 99% ee)

Nuclear magnetic resonance spectrum (400 MHz, $CDCl_3$) δ ppm: 7.49 (1H,d,J=7.3 Hz), 7.32–7.15 (3H,m), 4.28 (1H, d,J=2.9 Hz), 4.11 (1H,d,J=2.9 Hz), 4.30–4.03 (2H,m), 3.15 (2H,br.t,J=12.0 Hz), 1.95–1.74 (3H,m), 1.51 (9H,s), 1.58–1.50 (1H,m)

Infrared absorption spectrum $\lambda_{max}$ $cm^{-1}$ (KBr): 2949, 1679, 1424, 1365, 1244, 1168,765

Mass spectrometric analysis (EI) m/z: 301 ($M^+$ free form)

Elemental analysis (% based on $C_{18}H_{23}NO_3$)

Calculated: C: 71.74, H; 7.69, N; 4.65 Found: C; 71.62, H; 7.67, N: 4.59

HPLC analysis:

Column; Chiral Cel AD (product of Daicel Chemical Industries, Ltd., inner diameter: 4.6 mm, length: 250 mm)

Eluent; hexane : 2-propanol 80:20

Flow rate: 0.5 ml/min.

Temperature: 40° C.

Detection: 210 nm

Retention time: 13.2 min.

Referential Example 12

N-t-Butoxycarbonyl-spiro[((2S)-hydroxy)indane-1, 4'-piperidine]

In 5.0 ml of 1,4-dioxane, 125 mg (0.415 mmol) of N-t-butoxycarbonyl-spiro[((2R,3S)-epoxy)indane-1,4'-piperidine] were dissolved. To the resulting solution, 151 mg (2.49 mmol) of ammonium formate and 10 mg of 5% palladium-carbon were added, followed by stirring at 80° C. for 1 hour. To the reaction mixture, 120 mg of ammonium formate and 10 mg of 5% palladium-carbon were further added and the resulting mixture was stirred for one hour. After the reaction mixture was allowed to stand at room temperature, it was filtered. The solvent of the filtrate was distilled off under reduced pressure. The residue was purified by silica gel column chromatography (eluent; hexane-:ethyl acetate=3:1), whereby 118 mg (yield: 94%) of N-t-butoxycarbonylspiro[((2S)-hydroxy)indane-1,4'-piperidine] were obtained as white crystals.

The physical data of the title compound all coincided with those of the compound of Referential Example 6.

Referential Example 13

N-t-Butoxycarbonyl-spiro[((2S,3R)-epoxy)indane-1, 4'-piperidine]

Using 100 mg (0.35 mmol) of N-t-butoxycarbonyl-spiro [1H-indene-1,4'-piperidine] and 11.4 mg (0.018 mmol) of (R,R)-(−)-N,N'-bis(3,5-di-t-butylsalicylidene)-1,2-cyclohexane-diaminomanganese (III) chloride, 52.4 mg (yield: 50%, optical purity: 87% ee) of N-t-butoxycarbonylspiro[((2S,3R)-epoxy)indane-1,4'-piperidine] were obtained as white crystals in a similar manner to that described in Referential Example 11. The optical purity of the compound was determined by HPLC analysis.

The melting point, Nuclear Magnetic Resonance spectrum, Infrared absorption spectrum and Mass spectrometric analysis coincided with those of the (2R,3S) form prepared in Referential Example 11.

$[\alpha]_D^{25}$−63.50° (c=0.50, methanol, 99% ee)

Elemental analysis (% based on $C_{18}H_{23}NO_3$.1/3 $H_2O$)

Calculated: C; 70.33, H; 7.76, N; 4.56 Found: C; 70.22, H; 7.79, N; 4.53

HPLC analysis:

Column; Chiral Cel AD (product of Daicel Chemical Industries, Ltd., inner diameter: 4.6 mm, length:250 mm)

Eluent; hexane: 2-propanol=80:20

Flow rate; 0.5 ml/min.

Temperature; 40° C.

Detection; 210 nm

Retention time; 10.9 min.

FORMULATION EXAMPLE

Pharmaceutical formulations containing the compound (I) of the present invention, or a pharmaceutically acceptable salt or ester or another derivative thereof as an active ingredient are prepared as follows:

Formulation Example 1

Powder

Powders can be obtained by mixing the compound of Example 1 (5 g), lactose (895 g) and corn starch (100 g) in a blender.

Formulation Example 2

Granules

Granules can be prepared by mixing the compound of Example 2 (5 g), lactose (865 g) and low-substituted hydroxylpropylcellulose (100 g), adding 300 g of a 10% aqueous solution of hydroxypropylcellulose to the mixture, kneading the mixture. granulating the kneaded mass using an extrusion granulator and then drying the granulated product.

Formulation Example 3

Capsules

Capsules can be obtained by mixing the compound of Example 3 (5 g), lactose (115 g), corn starch (58 g) and magnesium stearate (2 g) in a V-shaped mixer and then filling the resulting mixture, in 180 mg portions, into No. 3 capsules.

Formulation Example 4

Tablets

Tablets can be obtained by mixing the compound of Example 4 (5 g), lactose (90 g), corn starch (34 g), crystalline cellulose (20 g) and magnesium stearate (1 g) in a blender and then tableting the resulting mixture using a tableting machine.

TEST EXAMPLE

Test example 1

$NK_1$ Receptor Binding Test (a) Preparation of Crude Pulmonary Membrane Specimens Crude pulmonary membrane specimens were prepared from the lungs of male Hartley guinea pigs. Namely, the animals were sacrificed by exsanguination from the abdominal aorta under chloroform anesthesia followed promptly by excision of lung and respiratory tract tissue.

After perfusing the excised lungs in buffer (1) (50 mM Tris-HCl, pH 7.4), the lungs were sliced into thin sections and then homogenized in a buffer (2) (buffer (1) containing 120 mM sodium chloride and 5 mM potassium chloride) using a Polytron.

The tissue mass was removed from the homogenate by passing through a Nylon mesh (50 μm) and separating by centrifugation (30,000×g, 30 minutes, 4° C.).

The pellet was re-suspended in an ice-cooled Buffer (3) (Buffer (1) containing 10 mM EDTA and 300 mM potassium chloride) and after allowing to stand undisturbed for 60 minutes at 4° C., the resulting suspension was centrifuged and washed twice (30,000×g, 15 minutes, 4° C.).

The crude membrane specimens were stored at −80° C. until the time of use.

(b) Receptor Binding Test

250 μl of crude pulmonary membrane specimen solution were added to 250 μl of a mixed solution of test drug and $[^3H]$-substance P (final concentration: 1 nM) (50 mM Tris-HCl, pH 7.4, 6 mM manganese chloride, 800 μg/ml BSA, 8 μg/ml chemostatin, 8 μg/ml leupeptin, 80 μg/ml bacitracin and 20 μg/ml phosphoramidone) followed by incubation for 30 minutes at room temperature.

After the reaction, the membrane component was recovered on a GF/B glass fiber filter (Whatman) using an automatic filtration system (Brandel).

Incidentally, the glass filter was pretreated for about 4 hours with 0.1% polyethyleneimine solution to minimize non-specific binding.

The filter containing the membrane component was transferred to a mini plastic vial containing 4 ml of Picoflow and radioactivity was measured with a liquid scintillation counter (Beckman, LCS3500).

Experiment 2

$NK_2$ Receptor Binding Test (a) Preparation of Crude Ileal Membrane Specimens

Crude membrane specimens were prepared from the ileum of male Hartley guinea pigs. Namely, the animals were sacrificed by exsanguination from the abdominal aorta under chloroform anesthesia followed promptly by excision of the ileum.

The excised ileum was separated into its contents, secretions and epithelium by scraping with a slide glass. After slicing into thin sections in buffer (1) (50 mM Tris-HCl, pH 7.4), it was homogenized in buffer (2) (buffer (1) containing 120 mM sodium chloride and 5 mM potassium chloride) using a Polytron.

The tissue mass was removed from the homogenate by passing through a Nylon mesh (50 μm) and separating by centrifugation (30,000×g, 30 minutes, 4° C.).

The pellet was re-suspended in an ice-cooled Buffer (3) (Buffer (1) containing 10 mM EDTA and 300 mM potassium chloride) and after allowing to stand undisturbed for 60 minutes at 4° C., the resulting suspension was centrifuged and washed twice (30,000×g, 15 minutes, 4° C.).

The crude membrane specimens were stored at −80° C. until the time of use.

(b) Receptor Binding Test 250 ml of crude ileal membrane specimen solution was added to 250 ml of a mixed solution of test drug and $[^3H]$-SR-48968 (Amersham, final concentration: 1 nM) (50 mM Tris-HCl pH 7.4, 6 mM manganese chloride, 800 μg/ml BSA, 8 μg/ml chemostatin, 8 μg/ml leupeptin, 80 μg/ml bacitracin and 20 μg/ml phosphoramidone) followed by incubation for 30 minutes at room temperature.

After the reaction, the membrane component was recovered on a GF/B glass fiber filter (Whatman) using an automatic filtration system (Brandel).

Incidentally, the glass filter was pretreated for about 4 hours with 0.1% polyethyleneimine solution to minimize non-specific binding.

The filter containing the membrane component was transferred to a mini plastic vial containing 4 ml of Picoflow and radioactivity was measured with a liquid scintillation counter (Beckman. LSC3500).

Experiment 3

Inhibitory Effect on Increased Vascular Permeability

The inhibitory effect on increased vascular permeability induced by $NK_1$ receptor antagonist substance P (SP) was assessed based on the amount of leaked pigment obtained using normal guinea pigs (male Hartley guinea pigs, body weights: approx. 400 g). Increased vascular permeability was induced by sequential administration of pigment (Evans blue: 20 mg/kg) to guinea pigs anesthetized with pentobarbital (25 mg/kg, i.p.) followed immediately by intravenous injection of SP (1 μg/kg). After 15 minutes, the guinea pigs were sacrificed under chloroform anesthesia and the amount of pigment that had leaked into the major areas of the respiratory tract was measured according to the method of Harada (J. Pharm. Pharmacol. 23, 218 (1971)). A test compound was suspended in a 0.5% tragacanth suspension and the resulting suspension was orally administered one hour before induction by SP.

The inhibitory effect was based on the amounts of the leaked pigment in the guinea pigs to which a test compound was administered.

Experiment 4

Inhibitory Effect on Respiratory Tract Contraction

The inhibitory effect of a test drug on respiratory tract contraction induced by neurokinin A (NKA), which is an $NK_2$ receptor agonist, was assessed based on respiratory tract internal pressure in accordance with a variation of the method of Konzett-Roessler (Naunyn-Schmiedebergs Arch. Exp. Pathol. Pharmakol. 195, 71 (1940)) using normal guinea pigs (male Hartley guinea pigs, body weights: approx. 500 g).

Namely, after implanting a respiratory tract cannula in the guinea pigs anesthetized with pentobarbital (30 mg/kg, i.p.) and administering gallamine (20 mg/kg, i.v.), the animals were immediately subjected to positive pressure breathing at 8 ml/kg and 60 cycles/minute (Ugo-Basile. 7025). Respiratory tract internal pressure during artificial respiration was amplified by means of a pressure transducer (Nippon Denko. TP-200T) installed in the side branch of the respiratory tract cannula received (Nippon Denko, AP-601G) and recorded with a recorder (Nippon Denko, WT-685G). Five minutes after pre-treatment with atropine (1 mg/kg, i.v.) and propranolol (1 mg/kg. i.v.), 4 μg/kg of NKA were intravenously administered to induce respiratory tract contraction. Respiratory tract internal pressure was then measured for 10 minutes. A test compound was prepared in a similar manner to that described in Experiment 3 and orally administered one hour before the induction by NKA.

The inhibitory activity was determined by a comparison in the area of respiratory tract internal pressure between the group to which a test compound was administered and the non-administered group.

Experiment 5

$NK_3$ Receptor Binding Test (a) Preparation of Crude Cerebral Membrane Specimens Crude membrane specimens were prepared from the brain of male Hartley guinea pigs. Namely, the animals were sacrificed by exsanguination from the abdominal aorta under chloroform anesthesia After perfusing with Buffer (1) (50 mM Tris-HCl, pH 7.4) from the right ventricle, the brain was enucleated immediately. The excised brain was homogenized in buffer (2) (buffer (1) containing 120 mM sodium chloride and 5 mM potassium chloride) using a Polytron. Tissue mass was removed from the homogenate by passing through a Nylon mesh (50 μm) and separating by centrifugation (30,000×g, 30 minutes, 4° C.). The pellet (membrane component) was suspended in an ice-cooled Buffer (3) (Buffer (1) containing 10 mM EDTA and 300 mM potassium chloride) and after allowing to stand undisturbed for 60 minutes at 4° C., the resulting suspension was centrifuged and washed twice (30,000×g, 15 minutes, 4° C.). This was suspended in Buffer (1) to prepare the crude membrane specimens. It was stored at −80° C. until the time of use in the receptor binding test.

(b) Receptor Binding Test

A test tube to be used for the reaction was treated in advance with Buffer (1) containing 5 mg/ml of bovine serum albumin (BSA). To 100 μl of Buffer (1) containing [$^3$H]-senktide, 6 mM of manganese chloride, 800 μg/ml of BSA, 8 μg/ml of chimostatin, 8 μg of leupeptin, 80 μg/ml of bacitracin and 20 μg/ml of phosphoramidone, 150 μl of Buffer (1) containing 400 μg/ml of BSA and a test compound were added. To the resulting mixture. 250 μl of the crude brain membrane specimen (adjusted to 1 mg/ml of a protein concentration) were added to start the reaction (at that time, the final concentration of the [$^3$H]-senktide in the reaction phase was 2.5 nM).

After incubation at room temperature for 60 minutes. the membrane component was recovered on a GF/B glass fiber filter (Whatman) using an automatic filtration system (Brandel), which had been pre-treated with 0.1% polyethyleneimine for more than 4 hours, followed by washing three times with 5 ml of ice-cooled Buffer (4) (5 mM tris-hydrochloric acid containing 400 μg/ml of BSA and 0.01% of sodium dodecylsulfate. pH 7.4).

The filter containing the membrane component was transferred to a mini plastic vial containing 4 ml of Picoflow and radioactivity was measured with a liquid scintillation counter (Aloka, LSC 3500).

In order to determine the radioactivity due to non-specific binding of [$^3$H]-senktide (binding to sites other than the receptor, for example, the filter), the Experiment was carried out by adding an excess amount of senktide (final concentration: 10 μM), and the radioactivity was measured.

The inhibitory ratio of senktide-receptor binding due to a test compound was calculated by the following equation.

$$\text{Inhibitory ratio } (\%) = [1-(C-A)/(B-A)]\times 100$$

A: radioactivity due to nonspecific binding

B: radioactivity in the test without the addition of a test compound

C: radioactivity in the test with the addition of a test compound

The compounds of Examples 1 and 2 exhibited, against all of $NK_1$, $NK_2$ and $NK_3$ receptors, antagonistic activities superior to those of Compound A.

Since the spiropiperidine derivatives of the present invention exhibit excellent antagonistic activity against $NK_1$, $NK_2$ and $NK_3$ receptors, have less toxicity and superior pharmacokinetics, they are useful as a medicament, particularly as a preventive or remedy for asthma and/or bronchitis, rhinitis, allergies, urinary incontinence, respiratory diseases and inflammatory bowel disease.

What is claimed is:

1. A compound represented by formula (IA)

(IA)

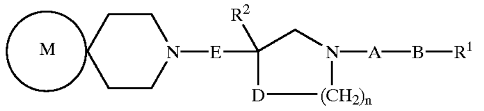

or a salt of a quaternary amine thereof of the formula (IB)

(IB)

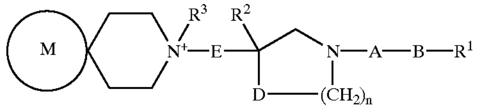

and a halogen ion, wherein:

$R^1$ and $R^2$ are the same or different and each is selected from the group consisting of
  an aryl group which is unsubstituted or substituted with 1 to 3 substituents selected from Substituent group A defined below, said aryl group being a $C_5$–$C_{14}$ aromatic hydrocarbon group which is unfused or fused with a $C_3$—$C_{10}$ cycloalkyl group and
  a 5- to 7-membered heteroaryl group containing 1 to 3 heteroatoms selected from the group consisting of an oxygen atom, a sulfur atom and a nitrogen atom, said heteroaryl group being unfused or fused with another cyclic group, said heteroaryl group being unsubstituted or substituted with 1 to 3 substituents selected from Substituent group A defined below;

A is selected from the group consisting of a methylene group, a carbonyl group and a sulfonyl group;

B is selected from the group consisting of a single bond, a $C_{1-4}$ alkylene group and a $C_{2-4}$ alkenylene group;

D is an oxygen atom;

E is selected from the group consisting of a $C_{1-4}$ alkylene group and a $C_{2-4}$ alkenylene group;

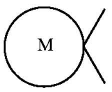 is selected from the group consisting of

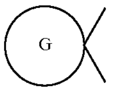 and 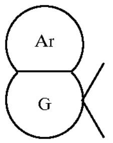

wherein

G is a $C_{5-8}$ cycloalkane ring which is substituted with 1 or 2 hydroxy groups;

Ar is selected from the group consisting of an aryl ring which is a $C_{6-14}$ aromatic hydrocarbon ring and which is unsubstituted or substituted with 1 to 3 groups selected from Substituent Group A defined below, and a 5- to 7-membered heteroaryl ring containing 1 to 3 heteroatoms selected from the group consisting of an oxygen atom, a sulfur atom and a nitrogen atom, said heteroaryl ring being unsubstituted or substituted with 1 to 3 groups selected from Substituent Group A defined below;

$R^3$ represents a straight or branched $C_1$–$C_6$ alkyl group; and n is 2;

Substituent Group A is selected from the group consisting of a halogen atom, a straight or branched $C_1$–$C_6$ alkyl group, a halogeno-lower alkyl group which is a straight or branched $C_1$–$C_6$ alkyl group substituted with 1 or more halogen atoms, a lower alkoxy group which is a straight or branched $C_1$–$C_6$ alkyl group attached to an oxygen atom, a lower alkoxycarbonyl group comprising a carbonyl group substituted with said lower alkoxy group, a carboxyl group, a hydroxyl group, a lower aliphatic acyl group which is a $C_2$–$C_7$, aliphatic acyl group, a lower aliphatic acylamino group comprising an amino group substituted with said lower aliphatic acyl group, an amino group and a cyano group;

or a pharmacologically acceptable salt or ester thereof.

2. A compound according to claim 1, wherein $R^1$ is selected from the group consisting of the unsubstituted aryl group, the unsubstituted heteroaryl group and the aryl group substituted with 1 to 3 groups Selected from Substituent Group A, or a pharmacologically acceptable salt or eater thereof.

3. A compound according to claim 1, wherein $R^1$ is selected from the group consisting of the unsubstituted aryl group and the aryl group substituted with 1 to 3 groups selected from the group consisting of a straight or branched $C_1$–$C_6$ alkyl group, the halogeno-lower alkyl group and the lower alkoxy group; or a pharmacologically acceptable salt or ester thereof.

4. A compound according to claim 1, wherein $R^2$ is selected from the group consisting of the unsubstituted aryl group and the aryl group substituted with 1 to 3 groups selected from Substituent Group A, or a pharmacologically acceptable salt or ester thereof.

5. A compound according to claim 1, wherein $R^2$ is the aryl group substituted with at least one group selected from Substituent Group A, or a pharmacologically acceptable salt or ester thereof.

6. A compound according to claim 1, wherein A represents the carbonyl group, or a pharmacologically acceptable salt or ester thereof.

7. A compound according to claim 1, wherein B represents the single bond, or a pharmacologically acceptable salt or ester thereof.

8. A compound according to claim 1, wherein E represents the $C_{1-4}$ alkylene group, or a pharmacologically acceptable salt or ester thereof.

9. A compound according to claim 1, wherein E represents a $C_{2-3}$ alkylene group, or a pharmacologically acceptable salt or ester thereof.

10. A compound according to claim 1, wherein

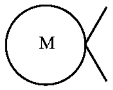 represents 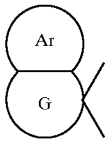, or a pharmacologically acceptable salt or ester thereof.

11. A compound according to claim 1, wherein

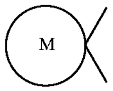 represents 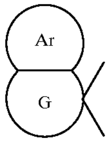, in which G is a cyclopentane ring which is substituted with a hydroxy group, or a pharmacologically acceptable salt or ester thereof.

12. A compound according to claim 1, wherein:

$R^1$ is selected from the group consisting of the unsubstituted aryl group, the unsubstituted heteroaryl group and the aryl group substituted with 1 to 3 groups selected from Substituent Group A;

$R^2$ is selected from the group consisting of the unsubstituted aryl group and the aryl group substituted with 1 to 3 groups selected from Substituent Group A;

A represents the carbonyl group;

B represents the single bond; and

E represents the $C_{1-4}$ alkylene group;

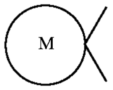 represents 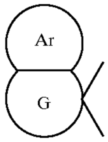;

or a pharmacologically acceptable salt or ester thereof.

13. A compound according to claim 1, wherein:

$R^1$ is selected from the group consisting of the unsubstituted aryl group and the aryl group substituted with 1 to 3 groups selected from the group consisting of a straight or branched $C_1$–$C_6$ alkyl group, the halogeno-lower alkyl group and the lower alkoxy group;

$R^2$ is the aryl group substituted with at least one group selected from Substituent-Group A;

A represents the carbonyl group;

B represents the single bond;

E represents a $C_{2-3}$ alkylene group; and

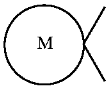 represents 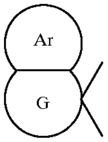

in which G is a cyclopentane ring which is substituted with a hydroxy group; or a pharmacologically acceptable salt or ester thereof.

14. A compound according to claim 13, wherein:

$R^1$ is a phenyl group substituted with 1 to 3 groups selected from the group consisting of a straight or branched $C_1$–$C_6$ alkyl group, the halogeno-lower alkyl group and the lower alkoxy group;

$R^2$ is a phenyl group substituted with at least one group selected from Substituent Group A;

Ar is a benzene ring which is unsubstituted or substituted with 1 to 3 groups selected from Substituent Group A; and said compound is a compound of the formula (IA);

or a pharmacologically acceptable salt or ester thereof.

15. A compound according to claim 14, wherein:

$R^1$ is selected from the group consisting of phenyl, 2-methoxyphenyl, 3-methoxyphenyl, 4-methoxyphenyl, 2,4-methoxyphenyl, 2,3-methoxyphenyl, 3,4-methoxyphenyl, 3,5-methoxyphenyl, 2,6-methoxyphenyl, 3,4,5-methoxyphenyl, 3-isopropylphenyl, 4-methylphenyl, 3,5-methylphenyl, 3,5-trifluoromethylphenyl and 3,5-methoxy-4-methylphenyl;

$R^2$ is selected from the group consisting of 3,4-dichlorophenyl, 4-chlorophenyl, 4-fluorophenyl and 3,4-difluorophenyl;

wherein G is selected from the group consisting of 1-hydroxycyclopentane and 2-hydroxycyclopentane; and Ar is a benzene ring;

or a pharmacologically acceptable salt or ester thereof.

16. A compound according to claim 1, which is selected from the group consisting of 1-{2-[(2R)-(3,4-dichlorophenyl)-4-(3,4,5-trimethoxybenzoyl)morpholin-2-yl]ethyl}spiro[(2-hydroxy)indane-1,4'-piperidine], 1-{2-[(2R)-(3,4-dichlorophenyl)-4-(3,4,5-trimethoxybenzoyl)morpholin-2-yl]ethyl}spiro[(3-hydroxy)indane-1,4'-piperidine], 1-{2-[(2R)-(3,4-dichlorophenyl)-4-(3,5-dimethoxybenzoyl)morpholin-2-yl]ethyl}spiro[(2-hydroxy)indane-1,4'-piperidine], and 1-{2-[(2R)-(3,4-dichlorophenyl)-4-(3,5-dimethoxybenzoyl)morpholin-2-yl]ethyl}spiro[(3-hydroxy)indane-1,4'-piperidine], or a pharmacologically acceptable salt or ester thereof.

17. A compound according to claim 1, which is

1-{2-(2R)-(3,4-dichlorophenyl)-4-(3,4,5-trimethoxybenzoyl)morpholin-2-yl]ethyl}spiro[(2-hydroxy)indane-1,4'-piperidine], or a pharmacologically acceptable salt or ester thereof.

18. A compound according to claim 1, wherein the heteroaryl ring and the heteroaryl group are selected from the group consisting of furan, thiophene, pyrrole, azepine, pyrazole, imidazole, oxazole, isoxazole, thiazole, isothiazole, 1,2,3-oxadiazole, triazole, tetrazole, thiadiazole, pyran, pyridine, pyridazine, pyrimidine and pyrazine, or a pharmacologically acceptable salt or ester thereof.

19. A compound according to claim 1, wherein the heteroaryl group is fused with another cyclic group to form a fused ring selected from the group consisting of indolyl, benzofuryl, benzothienyl, benzoazolyl, benzoimidazolyl, isoquinolyl, quinolyl and quinoxalyl, or a pharmacologically acceptable salt or ester thereof.

20. A compound according to claim 1, wherein the compound is 1-{2-[(2R)-(3,4-dichlorophenyl)-4-(3,4,5-trimethoxybenzoyl)morpholin-2-yl]ethyl}spiro[((2S)-hydroxy)indane-1,4'-piperidine]hydrochloride or a pharmacologically acceptable salt or ester thereof.

21. A compound according to claim 1, wherein the compound is a compound of the formula (IA), or a pharmacologically acceptable salt or ester thereof.

22. A compound according to claim 1, wherein the compound is the salt of the quaternary amine of the formula (IB) and the halogen ion is a chloride ion.

23. A compound according to claim 1, wherein the compound is the salt of the quaternary amine of the formula (IB) and the halogen ion is an iodine ion.

24. A pharmaceutical composition for the treatment of asthma or bronchitis comprising a pharmaceutically effective amount of a pharmacologically active compound together with a pharmaceutically acceptable carrier, wherein said pharmacologically active compound is a compound according to claim 1, or a pharmacologically acceptable salt or ester thereof.

25. A pharmaceutical composition for the treatment of asthma or bronchitis comprising a pharmaceutically effective amount of a pharmacologically active compound together with a pharmaceutically acceptable carrier, wherein said pharmacologically active compound is a compound according to claim 14, or a pharmacologically acceptable salt or ester thereof.

26. A pharmaceutical composition for the treatment of asthma or bronchitis comprising a pharmaceutically effective amount of a pharmacologically active compound together with a pharmaceutically acceptable carrier, wherein said pharmacologically active compound is a compound according to claim 16, or a pharmacologically acceptable salt or ester thereof.

27. A method for the treatment of asthma and/or bronchitis in a human, which comprises administering to said human an effective amount of a pharmacologically active compound effective in the treatment of asthma and/or bronchitis, wherein said pharmacologically active compound is a compound according to claim 1, or a pharmacologically acceptable salt or ester thereof.

28. A method for the treatment of asthma and/or bronchitis in a human, which comprises administering to said human an effective amount of a pharmacologically active compound effective in the treatment of asthma and/or bronchitis, wherein said pharmacologically active compound is a compound according to claim 14, or a pharmacologically acceptable salt or ester thereof.

29. A method for the treatment of asthma and/or bronchitis in a human, which comprises administering to said human an effective amount of a pharmacologically active compound effective in the treatment of asthma and/or bronchitis, wherein said pharmacologically active compound is a compound according, to claim 16, or a pharmacologically acceptable salt or ester thereof.

30. A method for the treatment of respiratory diseases in a human, which comprises administering to said human an effective amount of a pharmacologically active compound effective in the treatment of a respiratory disease selected from the group consisting of a chronic obstructive lung disease, pneumonia, bronchoconstriction and a cough, wherein said pharmacologically active compound is a compound according to claim 1, or a pharmacologically acceptable salt or ester thereof.

31. A method for the treatment of respiratory diseases in a human, which comprises administering to said human an effective amount of a pharmacologically active compound effective in the treatment of a respiratory disease selected from the group consisting of a chronic obstructive lung disease, pneumonia, bronchoconstriction and a cough, wherein said pharmacologically active compound is a compound according to claim 14, a pharmacologically acceptable salt or ester thereof.

32. A method for the treatment of respiratory diseases in a human, which comprises administering to said human an effective amount of a pharmacologically active compound effective in the treatment of a respiratory disease selected from the group consisting of a chronic obstructive lung disease, pneumonia, bronchoconstriction and a cough, wherein said pharmacologically active compound is a compound according to claim 16, or a pharmacologically acceptable salt or ester thereof.

33. A compound according to claim 1, wherein

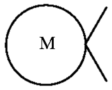

represents

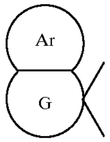

, in which G is a cyclopentane ring which is substituted with one or two hydroxy groups, or a pharmaceutically acceptable salt or ester thereof.

* * * * *